(12) United States Patent
Chowdhury et al.

(10) Patent No.: US 9,862,762 B2
(45) Date of Patent: Jan. 9, 2018

(54) MONOCLONAL ANTIBODIES WHICH BIND HUMAN PERIOSTIN

(71) Applicant: MEDIMMUNE, LLC, Gaithersburg, MD (US)

(72) Inventors: Partha Chowdhury, Gaithersburg, MD (US); Reena Varkey, Gaithersburg, MD (US); Meina Liang, Gaithersburg, MD (US); Yen-Wah Lee, Gaithersburg, MD (US); Katie Streicher, Gaithersburg, MD (US); Koustubh Ranade, Gaithersburg, MD (US); Ethan Grant, Gaithersburg, MD (US); Lydia Greenlees, Gaithersburg, MD (US); Yihong Yao, Gaithersburg, MD (US); Melissa Parker, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

(21) Appl. No.: 15/104,502

(22) PCT Filed: Feb. 5, 2015

(86) PCT No.: PCT/US2015/014652
§ 371 (c)(1),
(2) Date: Jun. 14, 2016

(87) PCT Pub. No.: WO2015/120171
PCT Pub. Date: Aug. 13, 2015

(65) Prior Publication Data
US 2016/0311894 A1 Oct. 27, 2016

Related U.S. Application Data

(60) Provisional application No. 61/936,967, filed on Feb. 7, 2014.

(51) Int. Cl.
*C07K 16/18* (2006.01)
*G01N 33/68* (2006.01)

(52) U.S. Cl.
CPC ............ *C07K 16/18* (2013.01); *G01N 33/68* (2013.01); *G01N 33/6869* (2013.01); *G01N 33/6884* (2013.01); *C07K 2317/33* (2013.01); *C07K 2317/54* (2013.01); *C07K 2317/55* (2013.01); *C07K 2317/622* (2013.01); *C07K 2317/76* (2013.01); *C07K 2319/00* (2013.01); *G01N 2800/12* (2013.01); *G01N 2800/122* (2013.01); *G01N 2800/52* (2013.01)

(58) Field of Classification Search
CPC C07K 16/18; C07K 2319/00; C07K 2317/33; C07K 2317/54; C07K 2317/55; C07K 2317/622; C07K 2317/76; G01N 33/68; G01N 33/6884; G01N 33/6869; G01N 2800/12; G01N 2800/122; G01N 2800/52
See application file for complete search history.

(56) References Cited

U.S. PATENT DOCUMENTS

| 5,892,019 | A | 4/1999 | Schlom et al. |
|---|---|---|---|
| 2009/0074788 | A1 | 3/2009 | Taniyama et al. |
| 2012/0052060 | A1 | 3/2012 | Monk et al. |
| 2012/0156194 | A1 | 6/2012 | Arron et al. |
| 2012/0219977 | A1 | 8/2012 | Garnero et al. |
| 2014/0308685 | A1* | 10/2014 | Izuhara .................. C07K 16/18 435/7.92 |
| 2017/0067053 | A1* | 3/2017 | Chatziantoniou ...... C07K 16/18 |

FOREIGN PATENT DOCUMENTS

| EP | 2754672 | 7/2014 |
|---|---|---|
| WO | 2009/124090 | 10/2009 |
| WO | 2012/083132 | 6/2012 |
| WO | 2013/035799 | 3/2013 |
| WO | 2013/126834 | 8/2013 |

OTHER PUBLICATIONS

American Thoratic Society, "Idiopathic pulmonary fibrosis: diagnosis and treatment. International consensus statement. American Thoracic Society (ATS), and the European Respiratory Society (ERS)," Am. J. Respir. Crit. Care Med., 2000, 161:646-664.
Antoniu SA., "Pitrakinra, a dual IL-4/IL-13 antagonist for the potential treatment of asthma and eczema," Curr Opin Investig Drugs, 2010, 11:1286-94.
Bender, B. G., "Overcoming barriers to nonadherence in asthma treatment," J Allergy Clin Immunol, 2002, 109:S554-9.
British Thoracic Society, Thorax, 2003, 58 Suppl I:1-94.
Chothia et al., "Canonical structures for the hypervariable regions of immunoglobulins," J. Mol. Biol., 1987, 196:901-917.
Corren et al., "Lebrikizumab treatment in adults with asthma," N Engl J Med., 2011, 365(12):1088-98.
Danese, et al., "Ulcerative Colitis," N Engl J Med., 2011, 365(18):1713-25.
Fish, L. and C. L. Lung, "Adherence to asthma therapy," Ann Allergy Asthma Immunol, 2001, 86:24-30.
Gina, "Global Strategy for Asthma Management and Prevention," 2002, National Institute of Health.
Jia, et al., "Periostin is a systemic biomarker of eosinophilic airway inflammation in asthmatic patients," J Allergy Clin. Immunol, 2012, 130:647-654.
Jovani, M., et al., "Anti-IL-13 in inflammatory bowel disease: from the bench to the bedside," Current Drug Targets, 2013,12:1444-52.

(Continued)

*Primary Examiner* — Robert Landsman
(74) *Attorney, Agent, or Firm* — Lisa V. Mueller; Michael Best & Friedrich LLP

(57) ABSTRACT

This disclosure provides a robust, sensitive, and specific assay for the detection and measurement of periostin levels in samples obtained from human patients having, or suspected of having an IL-13-mediated disease or disorder. The disclosure further provides novel antiperiostin monoclonal antibodies that recognize at least isoforms 1, 2, 3, 4, 7, and 8 of human periostin, and assay kits comprising one or more of these antibodies.

18 Claims, 21 Drawing Sheets

(56) References Cited

OTHER PUBLICATIONS

Figure 2A:
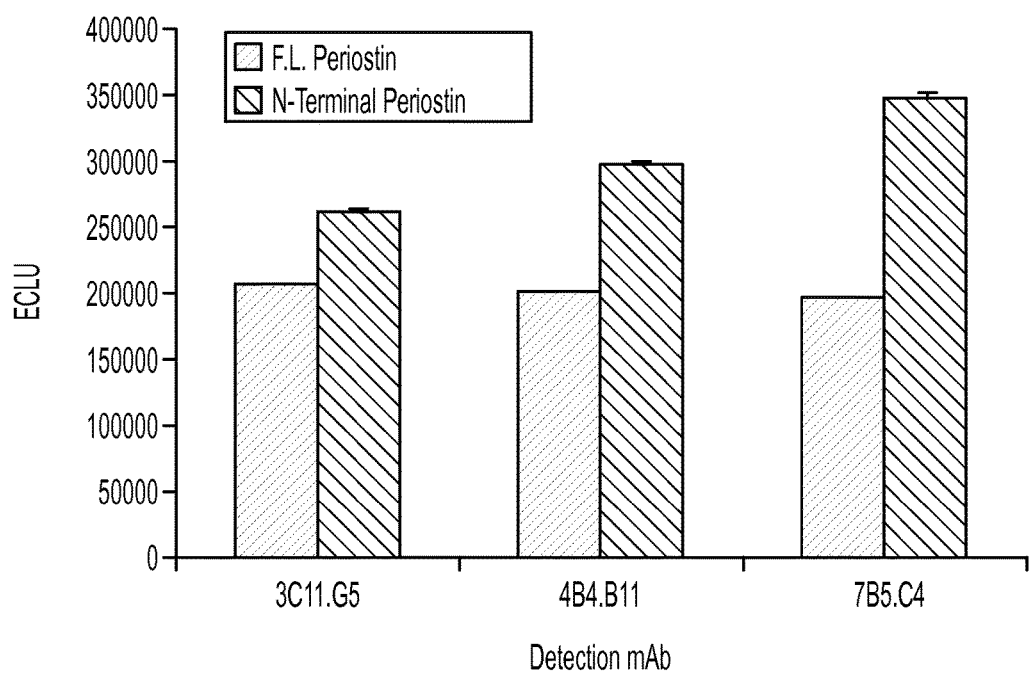

Kabat, E., et al., "Sequences of Proteins of Immunological Interest," U.S. Department of Health and Human Services, 1983.

Kioi M, et al., "Mechanism of action of interleukin-13 antagonist (IL-13E13K) in cells expressing various types of IL-4R," Cell Immunol, 2004, 229:41-51.

Masuoka, M., et al., "Periostin promotes chronic allergic inflammation in response to Th2 cytokines," J Clin Invest, 2012, 122:2590-2600.

McKenzie, A. N., et al., "Structural comparison and chromosomal localization of the human and mouse IL-13 genes," J Immunol, 1993, 150:5436-44.

Milgrom, H. et al., "Assessing adherence with asthma medication: making the counts count," Annals of Allergy, Asthma & Immunology, 2002, 88(5):429-31.

Minty, A. et al., "Interleukin-13 is a new human lymphokine regulating inflammatory and immune responses," Nature, 1993, 362:248-50.

Morra et al., "Characterization of periostin isoform pattern in non-small cell lung cancer," Lung Cancer, vol. 76, No. 2, 2012, pp. 183-190.

Rafii, R., et al., "A review of current and novel therapies for idiopathic pulmonary fibrosis," Journal of Thorasic Disease, 2013, 5(1):48-73.

Takayama, et al., "Periostin: a novel component of subepithelial fibrosis of bronchial asthma downstream of IL-4 and IL-13 signals," J Allergy Clin Immunol, 2006, 118(1):98-104.

Thomson et al., "Lebrikizumab in the personalized management of asthma," Biologics: Targets & Therapy 2012, vol. 6, 2012, pp. 329-335.

Zheng et al., "Inducible targeting of IL-13 to the adult lung causes matrix metalloproteinase- and cathepsin-dependent emphysema," J Clin Invest, 2000, 106(9):1081-93.

International Search Report and Written Opinion for Application No. PCT/US2015/014671 dated May 22, 2015 (14 pages).

International Search Report and Written Opinion for Application No. PCT/US2015/014652 dated May 11, 2015 (12 pages).

* cited by examiner

```
Periostin1   MIPFLPMFSLLLLLIVNPINANNHYDKILAHSRIRGRDQGPNVCALQQILGTKKKYFSTC 60
Periostin2   MIPFLPMFSLLLLLIVNPINANNHYDKILAHSRIRGRDQGPNVCALQQILGTKKKYFSTC 60
Periostin3   MIPFLPMFSLLLLLIVNPINANNHYDKILAHSRIRGRDQGPNVCALQQILGTKKKYFSTC 60
Periostin4   MIPFLPMFSLLLLLIVNPINANNHYDKILAHSRIRGRDQGPNVCALQQILGTKKKYFSTC 60
Nterm        --------------------NNHYDKILAHSRIRGRDQGPNVCALQQILGTKKKYFSTC 39
                                 ****************************************

Periostin1   KNWYKKSICGQKTTVLYECCPGYMRMEGMKGCPAVLPIDHVYGTLGIVGATTTQRYSDAS 120
Periostin2   KNWYKKSICGQKTTVLYECCPGYMRMEGMKGCPAVLPIDHVYGTLGIVGATTTQRYSDAS 120
Periostin3   KNWYKKSICGQKTTVLYECCPGYMRMEGMKGCPAVLPIDHVYGTLGIVGATTTQRYSDAS 120
Periostin4   KNWYKKSICGQKTTVLYECCPGYMRMEGMKGCPAVLPIDHVYGTLGIVGATTTQRYSDAS 120
Nterm        KNWYKKSICGQKTTVLYECCPGYMRMEGMKGCPAVLPIDHVYGTLGIVGATTTQRYSDAS 99
             ************************************************************

Periostin1   KLREEIEGKGSFTYFAPSNEAWDNLDSDIRRGLESNVNVELLNALHSHMINKRMLTKDLK 180
Periostin2   KLREEIEGKGSFTYFAPSNEAWDNLDSDIRRGLESNVNVELLNALHSHMINKRMLTKDLK 180
Periostin3   KLREEIEGKGSFTYFAPSNEAWDNLDSDIRRGLESNVNVELLNALHSHMINKRMLTKDLK 180
Periostin4   KLREEIEGKGSFTYFAPSNEAWDNLDSDIRRGLESNVNVELLNALHSHMINKRMLTKDLK 180
Nterm        KLREEIEGKGSFTYFAPSNEAWDNLDSDIRRGLESNVNVELLNALHSHMINKRMLTKDLK 159
             ************************************************************

Periostin1   NGMIIPSMYNNLGLFINHYPNGVVTVNCARIIHGNQIATNGVVHVIDRVLTQIGTSIQDF 240
Periostin2   NGMIIPSMYNNLGLFINHYPNGVVTVNCARIIHGNQIATNGVVHVIDRVLTQIGTSIQDF 240
Periostin3   NGMIIPSMYNNLGLFINHYPNGVVTVNCARIIHGNQIATNGVVHVIDRVLTQIGTSIQDF 240
Periostin4   NGMIIPSMYNNLGLFINHYPNGVVTVNCARIIHGNQIATNGVVHVIDRVLTQIGTSIQDF 240
Nterm        NGMIIPSMYNNLGLFINHYPNGVVTVNCARIIHGNQIATNGVVHVIDRVLTQIGTSIQDF 219
             ************************************************************

Periostin1   IEAEDDLSSFRAAAITSDILEALGRDGHFTLFAPTNEAFEKLPRGVLERIMGDKVASEAL 300
Periostin2   IEAEDDLSSFRAAAITSDILEALGRDGHFTLFAPTNEAFEKLPRGVLERIMGDKVASEAL 300
Periostin3   IEAEDDLSSFRAAAITSDILEALGRDGHFTLFAPTNEAFEKLPRGVLERIMGDKVASEAL 300
Periostin4   IEAEDDLSSFRAAAITSDILEALGRDGHFTLFAPTNEAFEKLPRGVLERIMGDKVASEAL 300
Nterm        IEAEDDLSSFRAAAITSDILEALGRDGHFTLFAPTNEAFEKLPRGVLERIMGDKVASEAL 279
             ************************************************************

Periostin1   MKYHILNTLQCSESIMGGAVFETLEGNTIEIGCDGDSITVNGIKMVNKKDIVTNNGVIHL 360
Periostin2   MKYHILNTLQCSESIMGGAVFETLEGNTIEIGCDGDSITVNGIKMVNKKDIVTNNGVIHL 360
Periostin3   MKYHILNTLQCSESIMGGAVFETLEGNTIEIGCDGDSITVNGIKMVNKKDIVTNNGVIHL 360
Periostin4   MKYHILNTLQCSESIMGGAVFETLEGNTIEIGCDGDSITVNGIKMVNKKDIVTNNGVIHL 360
Nterm        MKYHILNTLQCSESIMGGAVFETLEGNTIEIGCDGDSITVNGIKMVNKKDIVTNNGVIHL 339
             ************************************************************

Periostin1   IDQVLIPDSAKQVIELAGKQQTTFTDLVAQLGLASALRPDGEYTLLAPVNNAFSDDTLSM 420
Periostin2   IDQVLIPDSAKQVIELAGKQQTTFTDLVAQLGLASALRPDGEYTLLAPVNNAFSDDTLSM 420
Periostin3   IDQVLIPDSAKQVIELAGKQQTTFTDLVAQLGLASALRPDGEYTLLAPVNNAFSDDTLSM 420
Periostin4   IDQVLIPDSAKQVIELAGKQQTTFTDLVAQLGLASALRPDGEYTLLAPVNNAFSDDTLSM 420
Nterm        IDQVLIPDSAKQVIELAGKQQTTFTDLVAQLGLASALRPDGEYTLLAPVNNAFSDDTLSM 399
             ************************************************************
```

FIG. 1A

```
Periostin1  DQRLLKLILQNHILKVKVGLNELYNGQILETIGGKQLRVFVYRTAVCIENSCMEKGSKQG 480
Periostin2  DQRLLKLILQNHILKVKVGLNELYNGQILETIGGKQLRVFVYRTAVCIENSCMEKGSKQG 480
Periostin3  DQRLLKLILQNHILKVKVGLNELYNGQILETIGGKQLRVFVYRTAVCIENSCMEKGSKQG 480
Periostin4  DQRLLKLILQNHILKVKVGLNELYNGQILETIGGKQLRVFVYRTAVCIENSCMEKGSKQG 480
Nterm       DQRLLKLILQNHILKVKVGLNELYNGQILETIGGKQLRVFVYRTAVCIENSCMEKGSKQG 459
            ************************************************************

Periostin1  RNGAIHIFREIIKPAEKSLHEKLKQDKRFSTFLSLLEAADLKELLTQPGDWTLFVPTNDA 540
Periostin2  RNGAIHIFREIIKPAEKSLHEKLKQDKRFSTFLSLLEAADLKELLTQPGDWTLFVPTNDA 540
Periostin3  RNGAIHIFREIIKPAEKSLHEKLKQDKRFSTFLSLLEAADLKELLTQPGDWTLFVPTNDA 540
Periostin4  RNGAIHIFREIIKPAEKSLHEKLKQDKRFSTFLSLLEAADLKELLTQPGDWTLFVPTNDA 540
Nterm       RNGAIHIFREIIKPAEKSLHEKLKQDKRFSTFLSLLEAADLKELLTQPGDWTLFVPTNDA 519
            ************************************************************

Periostin1  FKGMTSEEKEILIRDKNALQNIILYHLTPGVFIGKGFEPGVTNILKTTQGSKIFLKEVND 600
Periostin2  FKGMTSEEKEILIRDKNALQNIILYHLTPGVFIGKGFEPGVTNILKTTQGSKIFLKEVND 600
Periostin3  FKGMTSEEKEILIRDKNALQNIILYHLTPGVFIGKGFEPGVTNILKTTQGSKIFLKEVND 600
Periostin4  FKGMTSEEKEILIRDKNALQNIILYHLTPGVFIGKGFEPGVTNILKTTQGSKIFLKEVND 600
Nterm       FKGMTSEEKEILIRDKNALQNIILYHLTPGVFIGKGFEPGVTNILKTTQGSKIFLKEVND 579
            ************************************************************

Periostin1  TLLVNELKSKESDIMTTNGVIHVVDKLLYPADTPVGNDQLLEILNKLIKYIQIKFVRGST 660
Periostin2  TLLVNELKSKESDIMTTNGVIHVVDKLLYPADTPVGNDQLLEILNKLIKYIQIKFVRGST 660
Periostin3  TLLVNELKSKESDIMTTNGVIHVVDKLLYPADTPVGNDQLLEILNKLIKYIQIKFVRGST 660
Periostin4  TLLVNELKSKESDIMTTNGVIHVVDKLLYPADTPVGNDQLLEILNKLIKYIQIKFVRGST 660
Nterm       TLLVNELKSKESDIMTTNGVIHVVDKLLYPADTPVGNDQLLEILNKLIKYIQIKFVRGST 639
            ************************************************************

Periostin1  FKEIPVTVYTTKIITKVVEPKIKVIEGSLQPIIKTEGPTLTKVKIEGEPEFRLIKEGETI 720
Periostin2  FKEIPVTVYK-------------------------------------------------  670
Periostin3  FKEIPVTVYR--------------------------PTLTKVKIEGEPEFRLIKEGETI 693
Periostin4  FKEIPVTVYK-------------------------------------------------  670
Nterm       FKEIPVTVYG-------------------------------------------------  649
            *********

Periostin1  TEVIHGEPIIKKYTKIIDGVPVEITEKETREERIITGPEIKYTRISTGGGETEETLKKLL 780
Periostin2  -------PIIKKYTKIIDGVPVEITEKETREERIITGPEIKYTRISTGGGETEETLKKLL 723
Periostin3  TEVIHGEPIIKKYTKIIDGVPVEITEKETREERIITGPEIKYTRISTGGGETEETLKKLL 753
Periostin4  -------PIIKKYTKIIDGVPVEITEKETREERIITGPEIKYTRISTGGGETEETLKKLL 723
Nterm       ---------------------------------------------GSGGHHHHHH-----  659
                                                              .:**   . ..

Periostin1  QEEVTKVTKFIEGGDGHLFEDEEIKRLLQGDTPVRKLQANKKVQGSRRRLREGRSQ 836
Periostin2  QEEVTKVTKFIEGGDGHLFEDEEIKRLLQGDTPVRKLQANKKVQGSRRRLREGRSQ 779
Periostin3  QED-----------------------------TPVRKLQANKKVQGSRRRLREGRSQ 781
Periostin4  QED-----------------------------TPVRKLQANKKVQGSRRRLREGRSQ 751
Nterm       --------------------------------------------------------
```

FIG. 1B

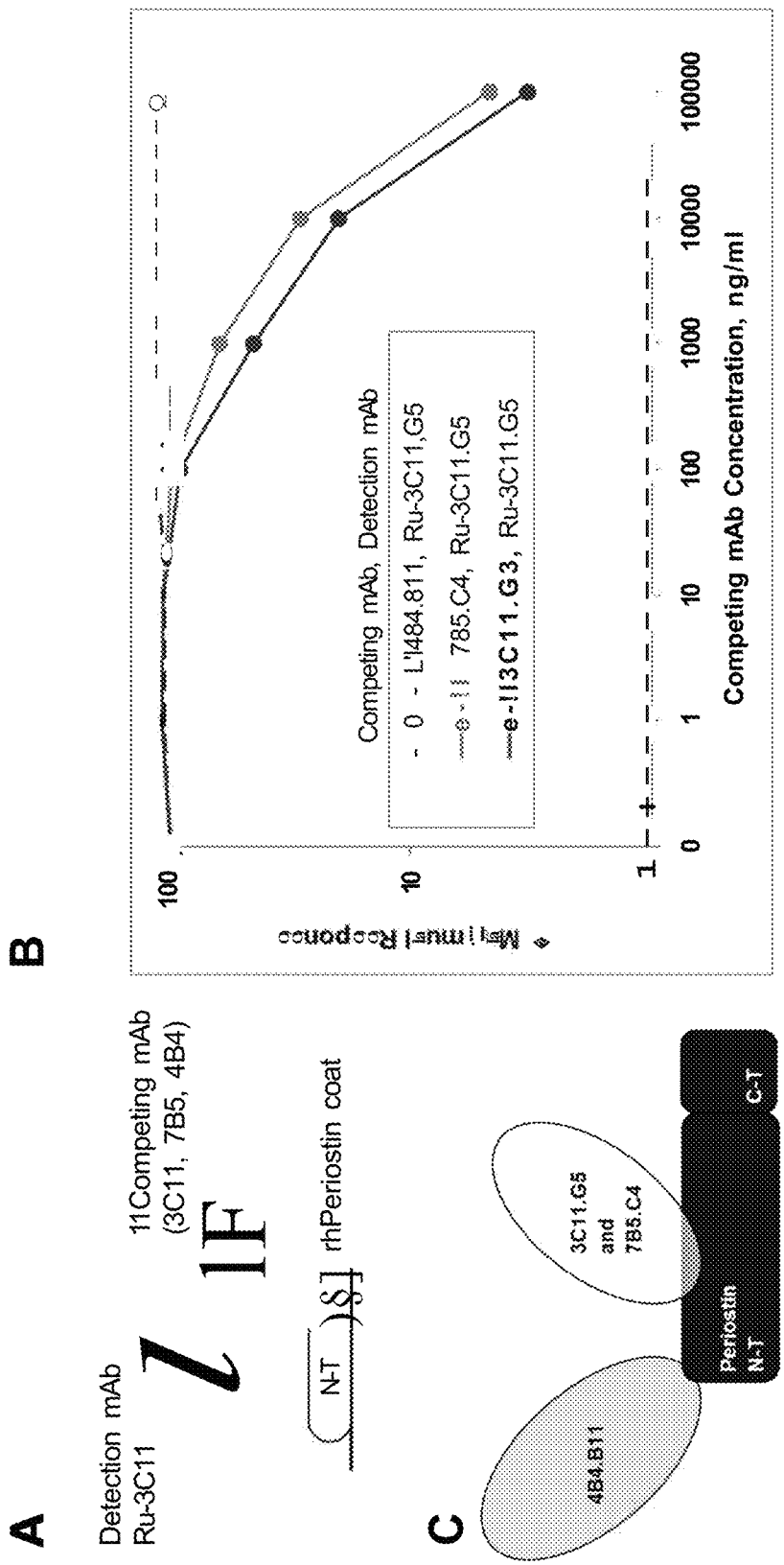
FIG. 3A, FIG. 3B, and FIG. 3C
7B5.C4 and 3C11.G5 antibodies are competitive inhibitors.

| | | | | | | | | |
|---|---|---|---|---|---|---|---|---|
| Isoform 1 | 1-13 | 14-16 | 17 | 18 | 19 | 20 | 21 | 22-23 |
| Isoform 2 | 1-13 | 14-16 | | 18 | 19 | 20 | 21 | 22-23 |
| Isoform 3 | 1-13 | 14-16 | | | 19 | 20 | | 22-23 |
| Isoform 4 | 1-13 | 14-16 | | | 19 | 20 | | 22-23 |
| Isoform 7 | 1-13 | 14-16 | | | | 20 | 21 | 22-23 |
| Isoform 8 | 1-13 | 14-16 | | | | 20 | | 22-23 |

FIG. 12

SEQUENCE LISTING

```
<160> NUMBER OF SEQ ID NOS: 17

<210> SEQ ID NO 1
<211> LENGTH: 836
<212> TYPE: PRT
<213> ORGANISM: Homo sapiens

<400> SEQUENCE: 1

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
        210                 215                 220

Val Ile Asp Arg Val Leu Thr Gln Ile Gly Thr Ser Ile Gln Asp Phe
```

-continued

```
           225                 230                 235                 240

Ile Glu Ala Glu Asp Asp Leu Ser Ser Phe Arg Ala Ala Ile Thr
               245                 250                 255

Ser Asp Ile Leu Glu Ala Leu Gly Arg Asp Gly His Phe Thr Leu Phe
               260                 265                 270

Ala Pro Thr Asn Glu Ala Phe Glu Lys Leu Pro Arg Gly Val Leu Glu
               275                 280                 285

Arg Ile Met Gly Asp Lys Val Ala Ser Glu Ala Leu Met Lys Tyr His
               290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
               325                 330                 335

Ser Ile Thr Val Asn Gly Ile Lys Met Val Asn Lys Lys Asp Ile Val
               340                 345                 350

Thr Asn Asn Gly Val Ile His Leu Ile Asp Gln Val Leu Ile Pro Asp
               355                 360                 365

Ser Ala Lys Gln Val Ile Glu Leu Ala Gly Lys Gln Gln Thr Thr Phe
               370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
               405                 410                 415

Thr Leu Ser Met Asp Gln Arg Leu Leu Lys Leu Ile Leu Gln Asn His
               420                 425                 430

Ile Leu Lys Val Lys Val Gly Leu Asn Glu Leu Tyr Asn Gly Gln Ile
               435                 440                 445

Leu Glu Thr Ile Gly Gly Lys Gln Leu Arg Val Phe Val Tyr Arg Thr
               450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
               485                 490                 495

Lys Ser Leu His Glu Lys Leu Lys Gln Asp Lys Arg Phe Ser Thr Phe
               500                 505                 510

Leu Ser Leu Leu Glu Ala Ala Asp Leu Lys Glu Leu Leu Thr Gln Pro
               515                 520                 525

Gly Asp Trp Thr Leu Phe Val Pro Thr Asn Asp Ala Phe Lys Gly Met
               530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
               565                 570                 575

Phe Glu Pro Gly Val Thr Asn Ile Leu Lys Thr Thr Gln Gly Ser Lys
               580                 585                 590

Ile Phe Leu Lys Glu Val Asn Asp Thr Leu Leu Val Asn Glu Leu Lys
               595                 600                 605

Ser Lys Glu Ser Asp Ile Met Thr Thr Asn Gly Val Ile His Val Val
               610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
               645                 650                 655
```

```
Arg Gly Ser Thr Phe Lys Glu Ile Pro Val Thr Val Tyr Thr Thr Lys
            660                 665                 670
Ile Ile Thr Lys Val Val Glu Pro Lys Ile Lys Val Ile Glu Gly Ser
        675                 680                 685
Leu Gln Pro Ile Ile Lys Thr Glu Gly Pro Thr Leu Thr Lys Val Lys
    690                 695                 700
Ile Glu Gly Glu Pro Glu Phe Arg Leu Ile Lys Glu Gly Thr Ile
705                 710                 715                 720
Thr Glu Val Ile His Gly Pro Ile Ile Lys Lys Tyr Thr Lys Ile
                725                 730                 735
Ile Asp Gly Val Pro Val Glu Ile Thr Glu Lys Glu Thr Arg Glu Glu
                740                 745                 750
Arg Ile Ile Thr Gly Pro Glu Ile Lys Tyr Thr Arg Ile Ser Thr Gly
            755                 760                 765
Gly Gly Glu Thr Glu Glu Thr Leu Lys Leu Leu Gln Glu Glu Val
    770                 775                 780
Thr Lys Val Thr Lys Phe Ile Glu Gly Gly Asp Gly His Leu Phe Glu
785                 790                 795                 800
Asp Glu Glu Ile Lys Arg Leu Leu Gln Gly Asp Thr Pro Val Arg Lys
                805                 810                 815
Leu Gln Ala Asn Lys Lys Val Gln Gly Ser Arg Arg Arg Leu Arg Glu
                820                 825                 830
Gly Arg Ser Gln
            835

<210> SEQ ID NO 2
<211> LENGTH: 779
<212> TYPE: PRT
<213> ORGANISM: Homo sapiens

<400> SEQUENCE: 2

Met Ile Pro Phe Leu Pro Met Phe Ser Leu Leu Leu Leu Leu Ile Val
1               5                   10                  15
Asn Pro Ile Asn Ala Asn Asn His Tyr Asp Lys Ile Leu Ala His Ser
            20                  25                  30
Arg Ile Arg Gly Arg Asp Gln Gly Pro Asn Val Cys Ala Leu Gln Gln
        35                  40                  45
Ile Leu Gly Thr Lys Lys Lys Tyr Phe Ser Thr Cys Lys Asn Trp Tyr
    50                  55                  60
Lys Lys Ser Ile Cys Gly Gln Lys Thr Thr Val Leu Tyr Glu Cys Cys
65                  70                  75                  80
Pro Gly Tyr Met Arg Met Glu Gly Met Lys Gly Cys Pro Ala Val Leu
                85                  90                  95
Pro Ile Asp His Val Tyr Gly Thr Leu Gly Ile Val Gly Ala Thr Thr
            100                 105                 110
Thr Gln Arg Tyr Ser Asp Ala Ser Lys Leu Arg Glu Glu Ile Glu Gly
        115                 120                 125
Lys Gly Ser Phe Thr Tyr Phe Ala Pro Ser Asn Glu Ala Trp Asp Asn
    130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
```

-continued

```
                180                 185                 190
Gly Leu Phe Ile Asn His Tyr Pro Asn Gly Val Val Thr Val Asn Cys
            195                 200                 205
Ala Arg Ile Ile His Gly Asn Gln Ile Ala Thr Asn Gly Val Val His
        210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ile Thr
            245                 250                 255
Ser Asp Ile Leu Glu Ala Leu Gly Arg Asp Gly His Phe Thr Leu Phe
        260                 265                 270
Ala Pro Thr Asn Glu Ala Phe Glu Lys Leu Pro Arg Gly Val Leu Glu
    275                 280                 285
Arg Ile Met Gly Asp Lys Val Ala Ser Glu Ala Leu Met Lys Tyr His
290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
            325                 330                 335
Ser Ile Thr Val Asn Gly Ile Lys Met Val Asn Lys Lys Asp Ile Val
            340                 345                 350
Thr Asn Asn Gly Val Ile His Leu Ile Asp Gln Val Leu Ile Pro Asp
    355                 360                 365
Ser Ala Lys Gln Val Ile Glu Leu Ala Gly Lys Gln Gln Thr Thr Phe
    370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
            405                 410                 415
Thr Leu Ser Met Asp Gln Arg Leu Leu Lys Leu Ile Leu Gln Asn His
        420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
            485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Thr Gln Pro
        515                 520                 525
Gly Asp Trp Thr Leu Phe Val Pro Thr Asn Asp Ala Phe Lys Gly Met
    530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
            565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
```

```
Ser Lys Glu Ser Asp Ile Met Thr Thr Asn Gly Val Ile His Val Val
    610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Lys Pro Ile
                660                 665                 670
Ile Lys Lys Tyr Thr Lys Ile Ile Asp Gly Val Pro Val Glu Ile Thr
            675                 680                 685
Glu Lys Glu Thr Arg Glu Arg Ile Ile Thr Gly Pro Glu Ile Lys
    690                 695                 700
Tyr Thr Arg Ile Ser Thr Gly Gly Glu Thr Glu Thr Leu Lys
705                 710                 715                 720
Lys Leu Leu Gln Glu Glu Val Thr Lys Val Thr Lys Phe Ile Glu Gly
                725                 730                 735
Gly Asp Gly His Leu Phe Glu Asp Glu Ile Lys Arg Leu Leu Gln
                740                 745                 750
Gly Asp Thr Pro Val Arg Lys Leu Gln Ala Asn Lys Lys Val Gln Gly
                755                 760                 765
Ser Arg Arg Arg Leu Arg Glu Gly Arg Ser Gln
    770                 775
```

<210> SEQ ID NO 3
<211> LENGTH: 781
<212> TYPE: PRT
<213> ORGANISM: Homo sapiens
<400> SEQUENCE: 3

```
Met Ile Pro Phe Leu Pro Met Phe Ser Leu Leu Leu Leu Leu Ile Val
1               5                   10                  15
Asn Pro Ile Asn Ala Asn Asn His Tyr Asp Lys Ile Leu Ala His Ser
                20                  25                  30
Arg Ile Arg Gly Arg Asp Gln Gly Pro Asn Val Cys Ala Leu Gln Gln
            35                  40                  45
Ile Leu Gly Thr Lys Lys Lys Tyr Phe Ser Thr Cys Lys Asn Trp Tyr
    50                  55                  60
Lys Lys Ser Ile Cys Gly Gln Lys Thr Thr Val Leu Tyr Glu Cys Cys
65                  70                  75                  80
Pro Gly Tyr Met Arg Met Glu Gly Met Lys Gly Cys Pro Ala Val Leu
                85                  90                  95
Pro Ile Asp His Val Tyr Gly Thr Leu Gly Ile Val Gly Ala Thr Thr
                100                 105                 110
Thr Gln Arg Tyr Ser Asp Ala Ser Lys Leu Arg Glu Glu Ile Glu Gly
            115                 120                 125
Lys Gly Ser Phe Thr Tyr Phe Ala Pro Ser Asn Glu Ala Trp Asp Asn
    130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
                180                 185                 190
Gly Leu Phe Ile Asn His Tyr Pro Asn Gly Val Val Thr Val Asn Cys
```

```
            195                 200                 205
Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                    245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                    325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                    405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                    485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
        610                 615                 620
```

```
Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
            675                 680                 685

Glu Gly Glu Thr Ile Thr Glu Val Ile His Gly Glu Pro Ile Ile Lys
690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
            725                 730                 735

Arg Ile Ser Thr Gly Gly Glu Thr Glu Glu Thr Leu Lys Lys Leu
            740                 745                 750

Leu Gln Glu Asp Thr Pro Val Arg Lys Leu Gln Ala Asn Lys Lys Val
            755                 760                 765

Gln Gly Ser Arg Arg Leu Arg Glu Gly Arg Ser Gln
            770                 775                 780

<210> SEQ ID NO 4
<211> LENGTH: 751
<212> TYPE: PRT
<213> ORGANISM: Homo sapiens

<400> SEQUENCE: 4

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
            85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
            130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
            165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
```

```
                 210                 215                 220
Val Ile Asp Arg Val Leu Thr Gln Ile Gly Thr Ser Ile Gln Asp Phe
225                 230                 235                 240

Ile Glu Ala Glu Asp Leu Ser Ser Phe Arg Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
                275                 280                 285

Arg Ile Met Gly Asp Lys Val Ala Ser Glu Ala Leu Met Lys Tyr His
                290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
                340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
                370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
                450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640
```

-continued

```
Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Arg Ile Ile Thr Gly Pro Glu Ile Lys
    690                 695                 700

Tyr Thr Arg Ile Ser Thr Gly Gly Gly Glu Thr Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Arg Leu Arg Glu Gly Arg Ser Gln
            740                 745                 750

<210> SEQ ID NO 5
<211> LENGTH: 659
<212> TYPE: PRT
<213> ORGANISM: Artificial Sequence
<220> FEATURE:
<223> OTHER INFORMATION: mature N-terminal region common to the four
      periostin isoforms

<400> SEQUENCE: 5

Asn Asn His Tyr Asp Lys Ile Leu Ala His Ser Arg Ile Arg Gly Arg
1               5                   10                  15

Asp Gln Gly Pro Asn Val Cys Ala Leu Gln Gln Ile Leu Gly Thr Lys
            20                  25                  30

Lys Lys Tyr Phe Ser Thr Cys Lys Asn Trp Tyr Lys Lys Ser Ile Cys
        35                  40                  45

Gly Gln Lys Thr Thr Val Leu Tyr Glu Cys Cys Pro Gly Tyr Met Arg
    50                  55                  60

Met Glu Gly Met Lys Gly Cys Pro Ala Val Leu Pro Ile Asp His Val
65                  70                  75                  80

Tyr Gly Thr Leu Gly Ile Val Gly Ala Thr Thr Thr Gln Arg Tyr Ser
                85                  90                  95

Asp Ala Ser Lys Leu Arg Glu Glu Ile Glu Gly Lys Gly Ser Phe Thr
            100                 105                 110

Tyr Phe Ala Pro Ser Asn Glu Ala Trp Asp Asn Leu Asp Ser Asp Ile
        115                 120                 125

Arg Arg Gly Leu Glu Ser Asn Val Asn Val Glu Leu Leu Asn Ala Leu
    130                 135                 140

His Ser His Met Ile Asn Lys Arg Met Leu Thr Lys Asp Leu Lys Asn
145                 150                 155                 160

Gly Met Ile Ile Pro Ser Met Tyr Asn Asn Leu Gly Leu Phe Ile Asn
                165                 170                 175

His Tyr Pro Asn Gly Val Val Thr Val Asn Cys Ala Arg Ile Ile His
            180                 185                 190

Gly Asn Gln Ile Ala Thr Asn Gly Val Val His Val Ile Asp Arg Val
        195                 200                 205

Leu Thr Gln Ile Gly Thr Ser Ile Gln Asp Phe Ile Glu Ala Glu Asp
    210                 215                 220

Asp Leu Ser Ser Phe Arg Ala Ala Ala Ile Thr Ser Asp Ile Leu Glu
225                 230                 235                 240

Ala Leu Gly Arg Asp Gly His Phe Thr Leu Phe Ala Pro Thr Asn Glu
```

```
                  245                 250                 255
Ala Phe Glu Lys Leu Pro Arg Gly Val Leu Glu Arg Ile Met Gly Asp
                260                 265                 270

Lys Val Ala Ser Glu Ala Leu Met Lys Tyr His Ile Leu Asn Thr Leu
            275                 280                 285

Gln Cys Ser Glu Ser Ile Met Gly Ala Val Phe Glu Thr Leu Glu
    290                 295                 300

Gly Asn Thr Ile Glu Ile Gly Cys Asp Gly Asp Ser Ile Thr Val Asn
305                 310                 315                 320

Gly Ile Lys Met Val Asn Lys Asp Ile Val Thr Asn Asn Gly Val
                325                 330                 335

Ile His Leu Ile Asp Gln Val Leu Ile Pro Asp Ser Ala Lys Gln Val
            340                 345                 350

Ile Glu Leu Ala Gly Lys Gln Gln Thr Thr Phe Thr Asp Leu Val Ala
                355                 360                 365

Gln Leu Gly Leu Ala Ser Ala Leu Arg Pro Asp Gly Glu Tyr Thr Leu
            370                 375                 380

Leu Ala Pro Val Asn Asn Ala Phe Ser Asp Asp Thr Leu Ser Met Asp
385                 390                 395                 400

Gln Arg Leu Leu Lys Leu Ile Leu Gln Asn His Ile Leu Lys Val Lys
                405                 410                 415

Val Gly Leu Asn Glu Leu Tyr Asn Gly Gln Ile Leu Glu Thr Ile Gly
            420                 425                 430

Gly Lys Gln Leu Arg Val Phe Val Tyr Arg Thr Ala Val Cys Ile Glu
                435                 440                 445

Asn Ser Cys Met Glu Lys Gly Ser Lys Gln Gly Arg Asn Gly Ala Ile
450                 455                 460

His Ile Phe Arg Glu Ile Ile Lys Pro Ala Glu Lys Ser Leu His Glu
465                 470                 475                 480

Lys Leu Lys Gln Asp Lys Arg Phe Ser Thr Phe Leu Ser Leu Glu
                485                 490                 495

Ala Ala Asp Leu Lys Glu Leu Leu Thr Gln Pro Gly Asp Trp Thr Leu
                500                 505                 510

Phe Val Pro Thr Asn Asp Ala Phe Lys Gly Met Thr Ser Glu Glu Lys
            515                 520                 525

Glu Ile Leu Ile Arg Asp Lys Asn Ala Leu Gln Asn Ile Ile Leu Tyr
            530                 535                 540

His Leu Thr Pro Gly Val Phe Ile Gly Lys Gly Phe Glu Pro Gly Val
545                 550                 555                 560

Thr Asn Ile Leu Lys Thr Thr Gln Gly Ser Lys Ile Phe Leu Lys Glu
            565                 570                 575

Val Asn Asp Thr Leu Leu Val Asn Glu Leu Lys Ser Lys Glu Ser Asp
            580                 585                 590

Ile Met Thr Thr Asn Gly Val Ile His Val Val Asp Lys Leu Leu Tyr
            595                 600                 605

Pro Ala Asp Thr Pro Val Gly Asn Asp Gln Leu Leu Glu Ile Leu Asn
            610                 615                 620

Lys Leu Ile Lys Tyr Ile Gln Ile Lys Phe Val Arg Gly Ser Thr Phe
625                 630                 635                 640

Lys Glu Ile Pro Val Thr Val Tyr Gly Gly Ser Gly His His His
                645                 650                 655

His His His
```

<210> SEQ ID NO 6
<211> LENGTH: 445
<212> TYPE: PRT
<213> ORGANISM: Homo sapiens
<220> FEATURE:
<221> NAME/KEY: MISC_FEATURE
<222> LOCATION: (1)..(445)
<223> OTHER INFORMATION: Lebrikizumab Heavy chain

<400> SEQUENCE: 6

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys

-continued

```
                355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 7
<211> LENGTH: 218
<212> TYPE: PRT
<213> ORGANISM: Homo sapiens
<220> FEATURE:
<221> NAME/KEY: MISC_FEATURE
<222> LOCATION: (1)..(218)
<223> OTHER INFORMATION: Lebrikizumab Light chain

<400> SEQUENCE: 7

Asp Ile Val Met Thr Gln Ser Pro Asp Ser Leu Ser Val Ser Leu Gly
1               5                   10                  15
Glu Arg Ala Thr Ile Asn Cys Arg Ala Ser Lys Ser Val Asp Ser Tyr
            20                  25                  30
Gly Asn Ser Phe Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Asn Asn
                85                  90                  95
Glu Asp Pro Arg Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 8
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
```

<223> OTHER INFORMATION: Tralokinumab Heavy chain

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 9
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: Tralokinumab Light chain

<400> SEQUENCE: 9

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 10
<211> LENGTH: 2563
<212> TYPE: DNA
<213> ORGANISM: Homo sapiens

<400> SEQUENCE: 10
ggcgcgccgc accatgattc ccttttttacc catgttttct ctactattgc tgcttattgt      60
taaccctata aacgccaaca atcattatga caagatcttg gctcatagtc gtatcagggg     120
tcgggaccaa ggcccaaatg tctgtgccct tcaacagatt ttgggcacca aaagaaata      180 cttcagcact tgtaagaact ggtataaaaa gtccatctgt ggacagaaaa cgactgtgtt     240
atatgaatgt tgccctggtt atatgagaat ggaaggaatg aaaggctgcc cagcagtttt     300

```
gcccattgac catgtttatg gcactctggg catcgtggga gccaccacaa cgcagcgcta    360
ttctgacgcc tcaaaactga gggaggagat cgagggaaag ggatccttca cttactttgc    420
accgagtaat gaggcttggg acaacttgga ttctgatatc cgtagaggtt tggagagcaa    480
cgtgaatgtt gaattactga atgctttaca tagtcacatg attaataaga gaatgttgac    540
caaggactta aaaaatggca tgattattcc ttcaatgtat aacaatttgg ggcttttcat    600
taaccattat cctaatgggg ttgtcactgt taattgtgct cgaatcatcc atgggaacca    660
gattgcaaca aatggtgttg tccatgtcat tgaccgtgtg cttacacaaa ttggtacctc    720
aattcaagac ttcattgaag cagaagatga cctttcatct tttagagcag ctgccatcac    780
atcggacata ttggaggccc ttggaagaga cggtcacttc acactctttg ctcccaccaa    840
tgaggctttt gagaaacttc cacgaggtgt cctagaaagg atcatgggag acaaagtggc    900
ttccgaagct cttatgaagt accacatctt aaatactctc cagtgttctg agtctattat    960
gggaggagca gtctttgaga cgctggaagg aaatacaatt gagataggat gtgacggtga   1020
cagtataaca gtaaatggaa tcaaaatggt gaacaaaaag gatattgtga caaataatgg   1080
tgtgatccat ttgattgatc aggtcctaat tcctgattct gccaaacaag ttattgagct   1140
ggctggaaaa cagcaaacca ccttcacgga tcttgtggcc caattaggct tggcatctgc   1200
tctgaggcca gatggagaat acactttgct ggcacctgtg aataatgcat tttctgatga   1260
tactctcagc atggatcagc gcctccttaa attaattctg cagaatcaca tattgaaagt   1320
aaaagttggc cttaatgagc tttacaacgg gcaaatactg gaaaccatcg gaggcaaaca   1380
gctcagagtc ttcgtatatc gtacagctgt ctgcattgaa aattcatgca tggagaaagg   1440
gagtaagcaa gggagaaacg gtgcgattca catattccgc gagatcatca agccagcaga   1500
gaaatccctc catgaaaagt taaacaaga taagcgcttt agcaccttcc tcagcctact   1560
tgaagctgca gacttgaaag agctcctgac acaacctgga gactggacat tatttgtgcc   1620
aaccaatgat gcttttaagg gaatgactag tgaagaaaaa gaaattctga tacgggacaa   1680
aaatgctctt caaaacatca ttctttatca cctgacacca ggagttttca ttggaaaagg   1740
atttgaacct ggtgttacta acattttaaa gaccacacaa ggaagcaaaa tctttctgaa   1800
agaagtaaat gatacacttc tggtgaatga attgaaatca aaagaatctg acatcatgac   1860
aacaaatggt gtaattcatg ttgtagataa actcctctat ccagcagaca cacctgttgg   1920
aaatgatcaa ctgctggaaa tacttaataa attaatcaaa tacatccaaa ttaagtttgt   1980
tcgtggtagc accttcaaag aaatccccgt gactgtctat acaactaaaa ttataaccaa   2040
agttgtggaa ccaaaaatta agtgattga aggcagtctt cagcctatta tcaaaactga   2100
aggacccaca ctaacaaaag tcaaaattga aggtgaacct gaattcagac tgattaaaga   2160
aggtgaaaca ataactgaag tgatccatgg agagccaatt attaaaaaat acaccaaaat   2220
cattgatgga gtgcctgtgg aaataactga aaaagagaca cgagaagaac gaatcattac   2280
aggtcctgaa ataaaataca ctaggatttc tactggaggt ggagaaacag aagaaactct   2340
gaagaaattg ttacaagaag aggtcaccaa ggtcaccaaa ttcattgaag tggtgatgg   2400
tcatttattt gaagatgaag aaattaaaag actgcttcag ggagacacac ccgtgaggaa   2460
gttgcaagcc aacaaaaaag ttcaaggatc tagaagacga ttaagggaag gtcgttctca   2520
ggggtctggc tcaggacacc atcatcacca tcatcaccac taa                     2563
```

<210> SEQ ID NO 11
<211> LENGTH: 2392

<212> TYPE: DNA
<213> ORGANISM: Homo sapiens

<400> SEQUENCE: 11

```
ggcgcgccgc accatgattc ccttttacc catgttttct ctactattgc tgcttattgt      60
taaccctata aacgccaaca atcattatga caagatcttg gctcatagtc gtatcagggg    120
tcgggaccaa ggcccaaatg tctgtgccct caacagatt ttgggcacca aaagaaata     180
cttcagcact tgtaagaact ggtataaaaa gtccatctgt ggacagaaaa cgactgtgtt    240
atatgaatgt tgccctggtt atatgagaat ggaaggaatg aaaggctgcc cagcagtttt    300
gcccattgac catgttatg gcactctggg catcgtggga gccaccacaa cgcagcgcta    360
ttctgacgcc tcaaaactga gggaggagat cgagggaaag ggatccttca cttactttgc    420
accgagtaat gaggcttggg acaacttgga ttctgatatc cgtagaggtt tggagagcaa    480
cgtgaatgtt gaattactga atgctttaca tagtcacatg attaataaga gaatgttgac    540
caaggactta aaaaatggca tgattattcc ttcaatgtat aacaatttgg ggcttttcat    600
taaccattat cctaatgggg ttgtcactgt taattgtgct cgaatcatcc atgggaacca    660
gattgcaaca aatggtgttg tccatgtcat tgaccgtgtg cttacacaaa ttggtacctc    720
aattcaagac ttcattgaag cagaagatga cctttcatct tttagagcag ctgccatcac    780
atcggacata ttggaggccc ttggaagaga cggtcacttc acactctttg ctcccaccaa    840
tgaggctttt gagaaacttc cacgaggtgt cctagaaagg atcatgggag acaaagtggc    900
ttccgaagct cttatgaagt accacatctt aaatactctc cagtgttctg agtctattat    960
gggaggagca gtctttgaga cgctggaagg aaatacaatt gagataggat gtgacggtga   1020
cagtataaca gtaaatggaa tcaaaatggt gaacaaaaag gatattgtga caaataatgg   1080
tgtgatccat ttgattgatc aggtcctaat tcctgattct gccaaacaag ttattgagct   1140
ggctggaaaa cagcaaacca ccttcacgga tcttgtggcc caattaggct tggcatctgc   1200
tctgaggcca gatggagaat acactttgct ggcacctgtg aataatgcat tttctgatga   1260
tactctcagc atggatcagc gcctccttaa attaattctg cagaatcaca tattgaaagt   1320
aaaagttggc cttaatgagc tttacaacgg gcaaatactg gaaaccatcg gaggcaaaca   1380
gctcagagtc ttcgtatatc gtacagctgt ctgcattgaa aattcatgca tggagaaagg   1440
gagtaagcaa gggagaaacg gtgcgattca catattccgc gagatcatca agccagcaga   1500
gaaatccctc catgaaaagt taaacaaga taagcgcttt agcaccttcc tcagcctact   1560
tgaagctgca gacttgaaag agctcctgac acaacctgga gactggacat tatttgtgcc   1620
aaccaatgat gcttttaagg gaatgactag tgaagaaaa gaaattctga tacgggacaa    1680
aaatgctctt caaaacatca ttctttatca cctgacacca ggagttttca ttggaaaagg   1740
atttgaacct ggtgttacta acattttaaa gaccacacaa ggaagcaaaa tctttctgaa   1800
agaagtaaat gatacacttc tggtgaatga attgaaatca aagaatctg acatcatgac    1860
aacaaatggt gtaattcatg ttgtagataa actcctctat ccagcagaca cacctgttgg    1920
aaatgatcaa ctgctggaaa tacttaataa attaatcaaa tacatccaaa ttaagtttgt   1980
tcgtggtagc accttcaaag aaatcccccgt gactgtctat aagccaatta ttaaaaaata   2040
caccaaaatc attgatggag tgcctgtgga ataactgaa aaagagacac gagaagaacg    2100
aatcattaca ggtcctgaaa taaaatacac taggatttct actggaggtg gagaaacaga   2160
agaaactctg aagaaattgt tacaagaaga ggtcaccaag gtcaccaaat tcattgaagg   2220
```

| | |
|---|---:|
| tggtgatggt catttatttg aagatgaaga aattaaaaga ctgcttcagg gagacacacc | 2280 |
| cgtgaggaag ttgcaagcca acaaaaaagt tcaaggatct agaagacgat taagggaagg | 2340 |
| tcgttctcag gggtctggct caggacacca tcatcaccat catcaccact aa | 2392 |

<210> SEQ ID NO 12
<211> LENGTH: 2398
<212> TYPE: DNA
<213> ORGANISM: Homo sapiens

<400> SEQUENCE: 12

| | |
|---|---:|
| ggcgcgccgc accatgattc ccttttacc catgttttct ctactattgc tgcttattgt | 60 |
| taaccctata aacgccaaca atcattatga caagatcttg gctcatagtc gtatcagggg | 120 |
| tcgggaccaa ggcccaaatg tctgtgccct tcaacagatt ttgggcacca aaaagaaata | 180 |
| cttcagcact tgtaagaact ggtataaaaa gtccatctgt ggacagaaaa cgactgtgtt | 240 |
| atatgaatgt tgccctggtt atatgagaat ggaaggaatg aaaggctgcc cagcagtttt | 300 |
| gcccattgac catgttttatg gcactctggg catcgtggga gccaccacaa cgcagcgcta | 360 |
| ttctgacgcc tcaaaactga gggaggagat cgagggaaag ggatccttca cttactttgc | 420 |
| accgagtaat gaggcttggg acaacttgga ttctgatatc cgtagaggtt tggagagcaa | 480 |
| cgtgaatgtt gaattactga atgctttaca tagtcacatg attaataaga gaatgttgac | 540 |
| caaggactta aaaaatggca tgattattcc ttcaatgtat aacaatttgg ggcttttcat | 600 |
| taaccattat cctaatgggg ttgtcactgt taattgtgct cgaatcatcc atgggaacca | 660 |
| gattgcaaca aatggtgttg tccatgtcat tgaccgtgtg cttacacaaa ttggtacctc | 720 |
| aattcaagac ttcattgaag cagaagatga cctttcatct tttagagcag ctgccatcac | 780 |
| atcggacata ttggaggccc ttggaagaga cggtcacttc acactctttg ctcccaccaa | 840 |
| tgaggctttt gagaaacttc acgaggtgt cctagaaagg atcatgggag acaaagtggc | 900 |
| ttccgaagct cttatgaagt accacatctt aaatactctc cagtgttctg agtctattat | 960 |
| gggaggagca gtctttgaga cgctggaagg aaatacaatt gagataggat gtgacggtga | 1020 |
| cagtataaca gtaaatggaa tcaaaatggt gaacaaaaag gatattgtga caaataatgg | 1080 |
| tgtgatccat ttgattgatc aggtcctaat tcctgattct gccaaacaag ttattgagct | 1140 |
| ggctggaaaa cagcaaacca ccttcacgga tcttgtggcc caattaggct tggcatctgc | 1200 |
| tctgaggcca gatggagaat acactttgct ggcacctgtg aataatgcat ttctgatga | 1260 |
| tactctcagc atggatcagc gcctccttaa attaattctg cagaatcaca tattgaaagt | 1320 |
| aaaagttggc cttaatgagc tttacaacgg gcaaatactg gaaaccatcg gaggcaaaca | 1380 |
| gctcagagtc ttcgtatatc gtacagctgt ctgcattgaa aattcatgca tggagaaagg | 1440 |
| gagtaagcaa gggagaaacg gtgcgattca catattccgc gagatcatca agccagcaga | 1500 |
| gaaatccctc catgaaaagt taaaacaaga taagcgcttt agcaccttcc tcagcctact | 1560 |
| tgaagctgca gacttgaaag agctcctgac acaacctgga gactggacat tatttgtgcc | 1620 |
| aaccaatgat gctttaagg gaatgactag tgaagaaaaa gaattctga tacgggacaa | 1680 |
| aaatgctctt caaacatca ttctttatca cctgacacca ggagttttca ttggaaaagg | 1740 |
| atttgaacct ggtgttacta acatttaaa gaccacacaa ggaagcaaaa tctttctgaa | 1800 |
| agaagtaaat gatacacttc tggtgaatga attgaaatca aaagaatctg acatcatgac | 1860 |
| aacaaatggt gtaattcatg ttgtagataa actcctctat ccagcagaca cacctgttgg | 1920 |
| aaatgatcaa ctgctggaaa tacttaataa attaatcaaa tacatccaaa ttaagtttgt | 1980 |

| | |
|---|---:|
| tcgtggtagc accttcaaag aaatccccgt gactgtctat agacccacac taacaaaagt | 2040 |
| caaaattgaa ggtgaacctg aattcagact gattaaagaa ggtgaaacaa taactgaagt | 2100 |
| gatccatgga gagccaatta ttaaaaaata caccaaaatc attgatggag tgcctgtgga | 2160 |
| aataactgaa aaagagacac gagaagaacg aatcattaca ggtcctgaaa taaaatacac | 2220 |
| taggatttct actggaggtg gagaaacaga agaaactctg aagaaattgt tacaagaaga | 2280 |
| cacacccgtg aggaagttgc aagccaacaa aaaagttcaa ggatctagaa gacgattaag | 2340 |
| ggaaggtcgt tctcagggt ctggctcagg acaccatcat caccatcatc accactaa | 2398 |

<210> SEQ ID NO 13
<211> LENGTH: 2308
<212> TYPE: DNA
<213> ORGANISM: Homo sapiens

<400> SEQUENCE: 13

| | |
|---|---:|
| ggcgcgccgc accatgattc ccttttttacc catgttttct ctactattgc tgcttattgt | 60 |
| taaccctata aacgccaaca atcattatga caagatcttg gctcatagtc gtatcagggg | 120 |
| tcgggaccaa ggcccaaatg tctgtgccct tcaacagatt ttgggcacca aaagaaata | 180 |
| cttcagcact tgtaagaact ggtataaaaa gtccatctgt ggacagaaaa cgactgtgtt | 240 |
| atatgaatgt tgccctggtt atatgagaat ggaaggaatg aaaggctgcc cagcagtttt | 300 |
| gcccattgac catgtttatg cactctggg catcgtggga gccaccacaa cgcagcgcta | 360 |
| ttctgacgcc tcaaaactga gggaggagat cgagggaaag ggatccttca cttactttgc | 420 |
| accgagtaat gaggcttggg acaacttgga ttctgatatc cgtagaggtt tggagagcaa | 480 |
| cgtgaatgtt gaattactga atgctttaca tagtcacatg attaataaga gaatgttgac | 540 |
| caaggactta aaaaatggca tgattattcc ttcaatgtat aacaatttgg ggcttttcat | 600 |
| taaccattat cctaatgggg ttgtcactgt taattgtgct cgaatcatcc atgggaacca | 660 |
| gattgcaaca aatggtgttg tccatgtcat tgaccgtgtg cttacacaaa ttggtacctc | 720 |
| aattcaagac ttcattgaag cagaagatga cctttcatct tttagagcag ctgccatcac | 780 |
| atcggacata ttggaggccc ttggaagaga cggtcacttc acactctttg ctcccaccaa | 840 |
| tgaggctttt gagaaacttc cacgaggtgt cctagaaagg atcatgggag acaaagtggc | 900 |
| ttccgaagct cttatgaagt accacatctt aaatactctc cagtgttctg agtctattat | 960 |
| gggaggagca gtctttgaga cgctggaagg aaatacaatt gagataggat gtgacggtga | 1020 |
| cagtataaca gtaaatggaa tcaaaatggt gaacaaaaag gatattgtga caaataatgg | 1080 |
| tgtgatccat ttgattgatc aggtcctaat tcctgattct gccaaacaag ttattgagct | 1140 |
| ggctggaaaa cagcaaacca ccttcacgga tcttgtggcc caattaggct tggcatctgc | 1200 |
| tctgaggcca gatggagaat acactttgct ggcacctgtg aataatgcat tttctgatga | 1260 |
| tactctcagc atggatcagc gcctccttaa attaattctg cagaatcaca tattgaaagt | 1320 |
| aaaagttggc cttaatgagc tttacaacgg gcaaatactg gaaaccatcg gaggcaaaca | 1380 |
| gctcagagtc ttcgtatatc gtacagctgt ctgcattgaa aattcatgca tggaaaagg | 1440 |
| gagtaagcaa gggagaaacg gtgcgattca catattccgc gagatcatca gccagcagaa | 1500 |
| gaaatccctc catgaaaagt taaaacaaga taagcgcttt agcaccttcc tcagcctact | 1560 |
| tgaagctgca gacttgaaag agctcctgac acaacctgga gactggacat tatttgtgcc | 1620 |
| aaccaatgat gcttttaagg gaatgactag tgaagaaaaa gaaattctga tacgggacaa | 1680 |

| | |
|---|---|
| aaatgctctt caaaacatca ttctttatca cctgacacca ggagttttca ttggaaaagg | 1740 |
| atttgaacct ggtgttacta acattttaaa gaccacacaa ggaagcaaaa tctttctgaa | 1800 |
| agaagtaaat gatacacttc tggtgaatga attgaaatca aaagaatctg acatcatgac | 1860 |
| aacaaatggt gtaattcatg ttgtagataa actcctctat ccagcagaca cacctgttgg | 1920 |
| aaatgatcaa ctgctggaaa tacttaataa attaatcaaa tacatccaaa ttaagtttgt | 1980 |
| tcgtggtagc accttcaaag aaatccccgt gactgtctat aagccaatta ttaaaaaata | 2040 |
| caccaaaatc attgatggag tgcctgtgga ataactgaa aaagagacac gagaagaacg | 2100 |
| aatcattaca ggtcctgaaa taaaatacac taggatttct actggaggtg gagaaacaga | 2160 |
| agaaactctg aagaaattgt tacaagaaga cacacccgtg aggaagttgc aagccaacaa | 2220 |
| aaaagttcaa ggatctagaa gacgattaag ggaaggtcgt tctcagggt ctggctcagg | 2280 |
| acaccatcat caccatcatc accactaa | 2308 |

<210> SEQ ID NO 14
<211> LENGTH: 2302
<212> TYPE: DNA
<213> ORGANISM: Homo sapiens

<400> SEQUENCE: 14

| | |
|---|---|
| ggcgcgccgc accatgattc ccttttacc catgttttct ctactattgc tgcttattgt | 60 |
| taaccctata aacgccaaca atcattatga caagatcttg gctcatagtc gtatcagggg | 120 |
| tcgggaccaa ggcccaaatg tctgtgccct tcaacagatt ttgggcacca aaaagaaata | 180 |
| cttcagcact tgtaagaact ggtataaaaa gtccatctgt ggacagaaaa cgactgtgtt | 240 |
| atatgaatgt tgccctggtt atatgagaat ggaaggaatg aaaggctgcc agcagttttt | 300 |
| gcccattgac catgttttatg gcactctggg catcgtggga ccaccacaa cgcagcgcta | 360 |
| ttctgacgcc tcaaaactga gggaggagat cgagggaaag ggatccttca cttactttgc | 420 |
| accgagtaat gaggcttggg acaacttgga ttctgatatc cgtagaggtt tggagagcaa | 480 |
| cgtgaatgtt gaattactga atgctttaca tagtcacatg attaataaga gaatgttgac | 540 |
| caaggactta aaaaatggca tgattattcc ttcaatgtat aacaatttgg ggcttttcat | 600 |
| taaccattat cctaatgggg ttgtcactgt taattgtgct cgaatcatcc atgggaacca | 660 |
| gattgcaaca aatggtgttg tccatgtcat tgaccgtgtg cttacacaaa ttggtacctc | 720 |
| aattcaagac ttcattgaag cagaagatga cctttcatct tttagagcag ctgccatcac | 780 |
| atcggacata ttggaggccc ttggaagaga cggtcacttc acactctttg ctcccaccaa | 840 |
| tgaggctttt gagaaacttc cacgaggtgt cctagaaagg atcatgggag acaaagtggc | 900 |
| ttccgaagct cttatgaagt accacatctt aaatactctc cagtgttctg agtctattat | 960 |
| gggaggagca gtctttgaga cgctggaagg aaatacaatt gagataggat gtgacggtga | 1020 |
| cagtataaca gtaaatggaa tcaaatggt gaacaaaaag gatattgtga caaataatgg | 1080 |
| tgtgatccat ttgattgatc aggtcctaat tcctgattct gccaaacaag ttattgagct | 1140 |
| ggctggaaaa cagcaaacca ccttcacgga tcttgtggcc caattaggct tggcatctgc | 1200 |
| tctgaggcca gatggagaat acactttgct ggcacctgtg aataatgcat tttctgatga | 1260 |
| tactctcagc atggatcagc gcctccttaa attaattctg cagaatcaca tattgaaagt | 1320 |
| aaaagttggc cttaatgagc tttacaacgg gcaaatactg gaaaccatcg gaggcaaaca | 1380 |
| gctcagagtc ttcgtatatc gtacagctgt ctgcattgaa aattcatgca tggagaaagg | 1440 |
| gagtaagcaa gggagaaacg gtgcgattca catattccgc gagatcatca agccagcaga | 1500 |

```
gaaatccctc catgaaaagt taaaacaaga taagcgcttt agcaccttcc tcagcctact   1560
tgaagctgca gacttgaaag agctcctgac acaacctgga gactggacat tatttgtgcc   1620
aaccaatgat gcttttaagg gaatgactag tgaagaaaaa gaaattctga tacgggacaa   1680
aaatgctctt caaaacatca ttctttatca cctgacacca ggagttttca ttggaaaagg   1740
atttgaacct ggtgttacta acattttaaa gaccacacaa ggaagcaaaa tctttctgaa   1800
agaagtaaat gatacacttc tggtgaatga attgaaatca aaagaatctg acatcatgac   1860
aacaaatggt gtaattcatg ttgtagataa actcctctat ccagcagaca cacctgttgg   1920
aaatgatcaa ctgctggaaa tacttaataa attaatcaaa tacatccaaa ttaagtttgt   1980
tcgtggtagc accttcaaag aaatccccgt gactgtctat ggtcctgaaa taaaatacac   2040
taggatttct actggaggtg gagaaacaga agaaactctg aagaaattgt tacaagaaga   2100
ggtcaccaag gtcaccaaat tcattgaagg tggtgatggt catttatttg aagatgaaga   2160
aattaaaaga ctgcttccag gagacacacc cgtgaggaag ttgcaagcca acaaaaaagt   2220
tcaaggatct agaagacgat taagggaagg tcgttctcag gggtctggct caggacacca   2280
tcatcaccat catcaccact aa                                            2302
```

<210> SEQ ID NO 15
<211> LENGTH: 2212
<212> TYPE: DNA
<213> ORGANISM: Homo sapiens

<400> SEQUENCE: 15

```
ggcgcgccgc accatgattc ccttttacc catgttttct ctactattgc tgcttattgt    60
taaccctata aacgccaaca atcattatga caagatcttg gctcatagtc gtatcagggg   120
tcgggaccaa ggcccaaatg tctgtgccct tcaacagatt ttgggcacca aaaagaaata   180
cttcagcact tgtaagaact ggtataaaaa gtccatctgt ggacagaaaa cgactgtgtt   240
atatgaatgt tgccctggtt atatgagaat ggaaggaatg aaaggctgcc cagcagtttt   300
gcccattgac catgtttatg cactctgggg catcgtggga gccaccacaa cgcagcgcta   360
ttctgacgcc tcaaaactga gggaggagat cgagggaaag ggatccttca cttactttgc   420
accgagtaat gaggcttggg acaacttgga ttctgatatc cgtagaggtt tggagagcaa   480
cgtgaatgtt gaattactga atgctttaca tagtcacatg attaataaga gaatgttgac   540
caaggactta aaaaatggca tgattattcc ttcaatgtat aacaatttgg ggcttttcat   600
taaccattat cctaatgggg ttgtcactgt taattgtgct cgaatcatcc atgggaacca   660
gattgcaaca aatggtgttg tccatgtcat tgaccgtgtg cttacacaaa ttggtaccto   720 aattcaagac ttcattgaag cagaagatga cctttcatct tttagagcag ctgccatcac   780
atcggacata ttggaggccc ttggaagaga cggtcacttc acactctttg ctcccaccaa   840
tgaggctttt gagaaacttc cacgaggtgt cctagaaagg atcatgggag acaaagtggc   900
ttccgaagct cttatgaagt accacatctt aaatactctc cagtgttctg agtctattat   960
gggaggagca gtcttttgaga cgctggaagg aaatacaatt gagataggat gtgacggtga  1020
cagtataaca gtaaatggaa tcaaaatggt gaacaaaaag gatattgtga caaataatgg  1080
tgtgatccat ttgattgatc aggtcctaat tcctgattct gccaaacaag ttattgagct  1140
ggctggaaaa cagcaaacca ccttcacgga tcttgtggcc caattaggct ggcatctgc   1200 tctgaggcca gatggagaat acactttgct ggcacctgtg aataatgcat tttctgatga  1260
```

```
tactctcagc atggatcagc gcctccttaa attaattctg cagaatcaca tattgaaagt    1320
aaaagttggc cttaatgagc tttacaacgg gcaaatactg gaaaccatcg gaggcaaaca    1380
gctcagagtc ttcgtatatc gtacagctgt ctgcattgaa aattcatgca tggagaaagg    1440
gagtaagcaa gggagaaacg gtgcgattca catattccgc gagatcatca agccagcaga    1500
gaaatccctc catgaaaagt taaaacaaga taagcgcttt agcaccttcc tcagcctact    1560
tgaagctgca gacttgaaag agctcctgac acaacctgga gactggacat tatttgtgcc    1620
aaccaatgat gcttttaagg gaatgactag tgaagaaaaa gaaattctga tacgggacaa    1680
aaatgctctt caaaacatca ttctttatca cctgacacca ggagttttca ttggaaaagg    1740
atttgaacct ggtgttacta acattttaaa gaccacacaa ggaagcaaaa tctttctgaa    1800
agaagtaaat gatacacttc tggtgaatga attgaaatca aaagaatctg acatcatgac    1860
aacaaatggt gtaattcatg ttgtagataa actcctctat ccagcagaca cacctgttgg    1920
aaatgatcaa ctgctggaaa tacttaataa attaatcaaa tacatccaaa ttaagtttgt    1980
tcgtggtagc accttcaaag aaatccccgt gactgtctat ggtcctgaaa taaaatacac    2040
taggatttct actggaggtg gagaaacaga agaaactctg aagaaattgt tacaagaacc    2100
cgtgaggaag ttgcaagcca acaaaaaagt tcaaggatct agaagacgat taagggaagg    2160
tcgttctcag gggtctggct caggacacca tcatcaccat catcaccact aa             2212
```

<210> SEQ ID NO 16
<211> LENGTH: 788
<212> TYPE: PRT
<213> ORGANISM: Homo sapiens

<400> SEQUENCE: 16

```
Ala Arg Arg Thr Met Ile Pro Phe Leu Pro Met Phe Ser Leu Leu Leu
1               5                   10                  15

Leu Leu Ile Val Asn Pro Ile Asn Ala Asn Asn His Tyr Asp Lys Ile
            20                  25                  30

Leu Ala His Ser Arg Ile Arg Gly Arg Asp Gln Gly Pro Asn Val Cys
        35                  40                  45

Ala Leu Gln Gln Ile Leu Gly Thr Lys Lys Tyr Phe Ser Thr Cys
    50                  55                  60

Lys Asn Trp Tyr Lys Lys Ser Ile Cys Gly Gln Lys Thr Thr Val Leu
65                  70                  75                  80

Tyr Glu Cys Cys Pro Gly Tyr Met Glu Thr Arg Met Glu Thr Glu Gly
                85                  90                  95

Met Glu Thr Lys Gly Cys Pro Ala Val Leu Pro Ile Asp His Val Tyr
            100                 105                 110

Gly Thr Leu Gly Ile Val Gly Ala Thr Thr Thr Gln Arg Tyr Ser Asp
        115                 120                 125

Ala Ser Lys Leu Arg Glu Glu Ile Glu Gly Lys Gly Ser Phe Thr Tyr
    130                 135                 140

Phe Ala Pro Ser Asn Glu Ala Trp Asp Asn Leu Asp Ser Asp Ile Arg
145                 150                 155                 160

Arg Gly Leu Glu Ser Asn Val Asn Val Glu Leu Leu Asn Ala Leu His
                165                 170                 175

Ser His Met Ile Asn Lys Arg Met Glu Thr Leu Thr Lys Asp Leu Lys
            180                 185                 190

Asn Gly Met Glu Thr Ile Ile Pro Ser Met Glu Thr Tyr Asn Asn Leu
        195                 200                 205
```

```
Gly Leu Phe Ile Asn His Tyr Pro Asn Gly Val Val Thr Val Asn Cys
210                 215                 220

Ala Arg Ile Ile His Gly Asn Gln Ile Ala Thr Asn Gly Val Val His
225                 230                 235                 240

Val Ile Asp Arg Val Leu Thr Gln Ile Gly Thr Ser Ile Gln Asp Phe
            245                 250                 255

Ile Glu Ala Glu Asp Asp Leu Ser Ser Phe Arg Ala Ala Ile Thr
        260                 265                 270

Ser Asp Ile Leu Glu Ala Leu Gly Arg Asp Gly His Phe Thr Leu Phe
        275                 280                 285

Ala Pro Thr Asn Glu Ala Phe Glu Lys Leu Pro Arg Gly Val Leu Glu
290                 295                 300

Arg Ile Met Glu Thr Gly Asp Lys Val Ala Ser Glu Ala Leu Met Glu
305                 310                 315                 320

Thr Lys Tyr His Ile Leu Asn Thr Leu Gln Cys Ser Glu Ser Ile Met
                325                 330                 335

Glu Thr Gly Gly Ala Val Phe Glu Thr Leu Glu Gly Asn Thr Ile Glu
            340                 345                 350

Ile Gly Cys Asp Gly Asp Ser Ile Thr Val Asn Gly Ile Lys Met Glu
        355                 360                 365

Thr Val Asn Lys Lys Asp Ile Val Thr Asn Asn Gly Val Ile His Leu
370                 375                 380

Ile Asp Gln Val Leu Ile Pro Asp Ser Ala Lys Gln Val Ile Glu Leu
385                 390                 395                 400

Ala Gly Lys Gln Gln Thr Thr Phe Thr Asp Leu Val Ala Gln Leu Gly
                405                 410                 415

Leu Ala Ser Ala Leu Arg Pro Asp Gly Glu Tyr Thr Leu Leu Ala Pro
            420                 425                 430

Val Asn Asn Ala Phe Ser Asp Thr Leu Ser Met Asp Gln Arg Leu
        435                 440                 445

Leu Lys Leu Ile Leu Gln Asn His Ile Leu Lys Val Lys Val Gly Leu
450                 455                 460

Asn Glu Leu Tyr Asn Gly Gln Ile Leu Glu Thr Ile Gly Gly Lys Gln
465                 470                 475                 480

Leu Arg Val Phe Val Tyr Arg Thr Ala Val Cys Ile Glu Asn Ser Cys
            485                 490                 495

Met Glu Thr Glu Lys Gly Ser Lys Gln Gly Arg Asn Gly Ala Ile His
                500                 505                 510

Ile Phe Arg Glu Ile Ile Lys Pro Ala Glu Lys Ser Leu His Glu Lys
            515                 520                 525

Leu Lys Gln Asp Lys Arg Phe Ser Thr Phe Leu Ser Leu Leu Glu Ala
530                 535                 540

Ala Asp Leu Lys Glu Leu Leu Thr Gln Pro Gly Asp Trp Thr Leu Phe
545                 550                 555                 560

Val Pro Thr Asn Asp Ala Phe Lys Gly Met Thr Ser Glu Glu Lys Glu
            565                 570                 575

Ile Leu Ile Arg Asp Lys Asn Ala Leu Gln Asn Ile Ile Leu Tyr His
                580                 585                 590

Leu Thr Pro Gly Val Phe Ile Gly Lys Gly Phe Glu Pro Gly Val Thr
            595                 600                 605

Asn Ile Leu Lys Thr Thr Gln Gly Ser Lys Ile Phe Leu Lys Glu Val
610                 615                 620

Asn Asp Thr Leu Leu Val Asn Glu Leu Lys Ser Lys Glu Ser Asp Ile
```

```
            625                 630                 635                 640
Met Thr Thr Asn Gly Val Ile His Val Asp Lys Leu Leu Tyr Pro
                    645                 650                 655
Ala Asp Thr Pro Val Gly Asn Asp Gln Leu Leu Glu Ile Leu Asn Lys
                        660                 665                 670
Leu Ile Lys Tyr Ile Gln Ile Lys Phe Val Arg Gly Ser Thr Phe Lys
                675                 680                 685
Glu Ile Pro Val Thr Val Tyr Gly Pro Glu Ile Lys Tyr Thr Arg Ile
            690                 695                 700
Ser Thr Gly Gly Glu Thr Glu Thr Leu Lys Lys Leu Leu Gln
705                 710                 715                 720
Glu Glu Val Thr Lys Val Thr Lys Phe Ile Glu Gly Asp Gly His
                    725                 730                 735
Leu Phe Glu Asp Glu Glu Ile Lys Arg Leu Leu Gln Gly Asp Thr Pro
                740                 745                 750
Val Arg Lys Leu Gln Ala Asn Lys Lys Val Gln Gly Ser Arg Arg Arg
                    755                 760                 765
Leu Arg Glu Gly Arg Ser Gln Gly Ser Gly Ser Gly His His His
                770                 775                 780
His His His His
785

<210> SEQ ID NO 17
<211> LENGTH: 736
<212> TYPE: PRT
<213> ORGANISM: Homo sapiens

<400> SEQUENCE: 17

Ala Arg Arg Thr Met Ile Pro Phe Leu Pro Met Phe Ser Leu Leu Leu
1               5                   10                  15
Leu Leu Ile Val Asn Pro Ile Asn Ala Asn Asn His Tyr Asp Lys Ile
                20                  25                  30
Leu Ala His Ser Arg Ile Arg Gly Arg Asp Gln Gly Pro Asn Val Cys
            35                  40                  45
Ala Leu Gln Gln Ile Leu Gly Thr Lys Lys Lys Tyr Phe Ser Thr Cys
        50                  55                  60
Lys Asn Trp Tyr Lys Lys Ser Ile Cys Gly Gln Lys Thr Thr Val Leu
65                  70                  75                  80
Tyr Glu Cys Cys Pro Gly Tyr Met Arg Met Glu Gly Met Lys Gly Cys
                    85                  90                  95
Pro Ala Val Leu Pro Ile Asp His Val Tyr Gly Thr Leu Gly Ile Val
                100                 105                 110
Gly Ala Thr Thr Thr Gln Arg Tyr Ser Asp Ala Ser Lys Leu Arg Glu
            115                 120                 125
Glu Ile Glu Gly Lys Gly Ser Phe Thr Tyr Phe Ala Pro Ser Asn Glu
        130                 135                 140
Ala Trp Asp Asn Leu Asp Ser Asp Ile Arg Arg Gly Leu Glu Ser Asn
145                 150                 155                 160
Val Asn Val Glu Leu Leu Asn Ala Leu His Ser His Met Ile Asn Lys
                165                 170                 175
Arg Met Leu Thr Lys Asp Leu Lys Asn Gly Met Ile Ile Pro Ser Met
                180                 185                 190
Tyr Asn Asn Leu Gly Leu Phe Ile Asn His Tyr Pro Asn Gly Val Val
            195                 200                 205
```

```
Thr Val Asn Cys Ala Arg Ile Ile His Gly Asn Gln Ile Ala Thr Asn
    210                 215                 220

Gly Val Val His Val Ile Asp Arg Val Leu Thr Gln Ile Gly Thr Ser
225                 230                 235                 240

Ile Gln Asp Phe Ile Glu Ala Glu Asp Leu Ser Ser Phe Arg Ala
                245                 250                 255

Ala Ala Ile Thr Ser Asp Ile Leu Glu Ala Leu Gly Arg Asp Gly His
            260                 265                 270

Phe Thr Leu Phe Ala Pro Thr Asn Glu Ala Phe Glu Lys Leu Pro Arg
        275                 280                 285

Gly Val Leu Glu Arg Ile Met Gly Asp Lys Val Ala Ser Glu Ala Leu
290                 295                 300

Met Lys Tyr His Ile Leu Asn Thr Leu Gln Cys Ser Glu Ser Ile Met
305                 310                 315                 320

Gly Gly Ala Val Phe Glu Thr Leu Glu Gly Asn Thr Ile Glu Ile Gly
                325                 330                 335

Cys Asp Gly Asp Ser Ile Thr Val Asn Gly Ile Lys Met Val Asn Lys
            340                 345                 350

Lys Asp Ile Val Thr Asn Asn Gly Val Ile His Leu Ile Asp Gln Val
        355                 360                 365

Leu Ile Pro Asp Ser Ala Lys Gln Val Ile Glu Leu Ala Gly Lys Gln
370                 375                 380

Gln Thr Thr Phe Thr Asp Leu Val Ala Gln Leu Gly Leu Ala Ser Ala
385                 390                 395                 400

Leu Arg Pro Asp Gly Glu Tyr Thr Leu Leu Ala Pro Val Asn Asn Ala
                405                 410                 415

Phe Ser Asp Asp Thr Leu Ser Met Asp Gln Arg Leu Leu Lys Leu Ile
            420                 425                 430

Leu Gln Asn His Ile Leu Lys Val Lys Val Gly Leu Asn Glu Leu Tyr
        435                 440                 445

Asn Gly Gln Ile Leu Glu Thr Ile Gly Gly Lys Gln Leu Arg Val Phe
450                 455                 460

Val Tyr Arg Thr Ala Val Cys Ile Glu Asn Ser Cys Met Glu Lys Gly
465                 470                 475                 480

Ser Lys Gln Gly Arg Asn Gly Ala Ile His Ile Phe Arg Glu Ile Ile
                485                 490                 495

Lys Pro Ala Glu Lys Ser Leu His Glu Lys Leu Lys Gln Asp Lys Arg
            500                 505                 510

Phe Ser Thr Phe Leu Ser Leu Leu Glu Ala Ala Asp Leu Lys Glu Leu
        515                 520                 525

Leu Thr Gln Pro Gly Asp Trp Thr Leu Phe Val Pro Thr Asn Asp Ala
530                 535                 540

Phe Lys Gly Met Thr Ser Glu Glu Lys Glu Ile Leu Ile Arg Asp Lys
545                 550                 555                 560

Asn Ala Leu Gln Asn Ile Ile Leu Tyr His Leu Thr Pro Gly Val Phe
                565                 570                 575

Ile Gly Lys Gly Phe Glu Pro Gly Val Thr Asn Ile Leu Lys Thr Thr
            580                 585                 590

Gln Gly Ser Lys Ile Phe Leu Lys Glu Val Asn Asp Thr Leu Leu Val
        595                 600                 605

Asn Glu Leu Lys Ser Lys Glu Ser Asp Ile Met Thr Thr Asn Gly Val
610                 615                 620

Ile His Val Val Asp Lys Leu Leu Tyr Pro Ala Asp Thr Pro Val Gly
```

-continued

```
            625                 630                 635                 640

Asn Asp Gln Leu Leu Glu Ile Leu Asn Lys Leu Ile Lys Tyr Ile Gln
                    645                 650                 655

Ile Lys Phe Val Arg Gly Ser Thr Phe Lys Glu Ile Pro Val Thr Val
                    660                 665                 670

Tyr Gly Pro Glu Ile Lys Tyr Thr Arg Ile Ser Thr Gly Gly Gly Glu
                    675                 680                 685

Thr Glu Glu Thr Leu Lys Lys Leu Leu Gln Glu Pro Val Arg Lys Leu
                    690                 695                 700

Gln Ala Asn Lys Lys Val Gln Gly Ser Arg Arg Arg Leu Arg Glu Gly
705                 710                 715                 720

Arg Ser Gln Gly Ser Gly Ser Gly His His His His His His His
                    725                 730                 735
```

MONOCLONAL ANTIBODIES WHICH BIND HUMAN PERIOSTIN

CROSS-REFERENCE TO RELATED APPLICATIONS

This is a U.S. national stage entry of International Patent Application No. PCT/US2015/014652, filed on Feb. 5, 2015, which claims priority to U.S. Provisional Patent Application No. 61/936,967, filed on Feb. 7, 2014, the entire contents of all of which are fully incorporated herein by reference.

REFERENCE TO SEQUENCE LISTING SUBMITTED ELECTRONICALLY

The content of the electronically submitted sequence listing in ASCII text file (Name SequenceListing-Text; Size: 73,429 bytes; and Date of Creation: Feb. 2, 2015) filed with the application is incorporated herein by reference in its entirety.

BACKGROUND

Interleukin (IL)-13 is a 114 amino acid cytokine with an unmodified molecular mass of approximately 12 kDa (McKenzie, A. N., et al. J Immunol, 1993. 150:5436-44; Minty, A., et al. Nature, 1993. 362:248-50). IL-13 levels have been shown to correlate with disease severity in asthmatics and rodent models of allergic inflammation (see U.S. Pat. Appl. Publ. No. 2012-0052060, published Mar. 1, 2012, and incorporated herein by reference in its entirety).

Bronchial asthma is a common persistent inflammatory disease of the lung characterized by airways hyper-responsiveness, mucus overproduction, fibrosis, and raised serum IgE levels. Airways hyper-responsiveness (AHR) is the exaggerated constriction of the airways to non-specific stimuli such as cold air. Both AHR and mucus overproduction are thought to be responsible for the variable airway obstruction that leads to the shortness of breath characteristic of asthma attacks (exacerbations) and which is responsible for the mortality associated with this disease.

Current British Thoracic Society (BTS) and Global Initiative for Asthma (GINA) guidelines suggest a stepwise approach to the treatment of asthma (Society, B. T., Thorax, 2003. 58 Suppl 1:1-94; GINA, Global Strategy for Asthma Management and Prevention. 2002, National Institute of Health). Mild to moderate asthma can usually be controlled by the use of inhaled corticosteroids, in combination with beta-agonists or leukotriene inhibitors. However, due to the documented side effects of corticosteroids, patients tend not to comply with the treatment regime, which reduces the effectiveness of treatment (Milgrom, H. et al. Ann Allergy Asthma Immunol, 2002. 88:429-31; Fish, L. and C. L. Lung, Ann Allergy Asthma Immunol, 2001. 86:24-30; Bender, B. G. J Allergy Clin Immunol, 2002. 109: S554-9).

Chronic Obstructive Pulmonary Disease (COPD) includes patient populations with varying degrees of chronic bronchitis, small airway disease, and emphysema, and is characterized by progressive irreversible lung function decline that responds poorly to current asthma based therapy. Zheng et al (J Clin Invest, 2000. 106:1081-93) have demonstrated that overexpression of IL-13 in the mouse lung caused emphysema, elevated mucus production, and inflammation, reflecting aspects of human COPD. The signs are therefore that IL-13 plays an important role in the pathogenesis of COPD, particularly in patients with asthma-like features. IL-13 may also play a role in the pathogenesis of inflammatory bowel disease, and has been associated with fibrotic conditions, such as idiopathic pulmonary fibrosis (IPF). See, e.g., Jovani, M., et al. Curr Drug Targets. 2013.12:1444-52; and Rafii, R., et al. J Thorac Dis. 2013. 1:48-73

Periostin (also known as Osteoblast-Specific Factor 2) is a matricellular protein belonging to the fasciclin family (Masuoka, M., et al. J Clin Invest 2012. 122:2590-2600). Periostin is a highly inducible product of IL-4 or IL-13 in lung fibroblasts, and is involved in fibrosis of bronchial asthma, and other firms of allergic inflammation (Id.). While increased periostin levels are known to correlate with certain IL-13-mediated diseases or disorders, there remains a need for specific and sensitive assays to determine changes in periostin levels in patients suspected or known to have an IL-13-mediated disease or disorder.

SUMMARY

This disclosure provides methods and compositions for treating and diagnosing IL-13-mediated diseases or disorders through measurement of periostin levels in a subject or patient. The methods provided herein can include an immunoassay employing one or more anti-periostin antibodies or antigen binding fragments thereof, where the antibodies or fragments thereof recognize isoforms 1, 2, 3, and 4 of human periostin. The compositions provided herein can include antibodies or fragments thereof recognize isoforms 1, 2, 3, and 4 of human periostin.

In one aspect, the disclosure provides a method of treating a patient having an IL-13-mediated disease or disorder, comprising administering an IL-13 antagonist to the patient if the periostin level in a sample taken from the patient is above a predetermined threshold level, or is elevated relative to the periostin level in one or more control samples. In certain aspects, a patient can be identified as a candidate for treatment by having an elevate periostin level. According to these aspects, the patient's periostin level can be measured in an immunoassay employing one or more anti-periostin antibodies or antigen binding fragments thereof, where the antibodies or fragments thereof recognize isoforms 1, 2, 3, and 4 of human periostin. In certain aspects, the sample taken from the patient by, e.g., a healthcare provider, can be submitted, e.g., to a clinical laboratory which performs the immunoassay measuring the periostin level in the sample.

The disclosure further provides a method of treating a patient having, or suspected of having an IL-13-mediated disease or disorder, where the method includes submitting a first sample, e.g., a body fluid or tissue, taken from the patient for measurement of a first periostin level in the sample. As above, the patient's periostin level can be measured in an immunoassay employing one or more anti-periostin antibodies or antigen binding fragments thereof which recognize isoforms 1, 2, 3, and 4 of human periostin. The method further includes administering an IL-13 antagonist to the patient, e.g., a patient identified for treatment of an IL-13-mediated disease or disorder, if the patient's periostin level in the first sample is above a predetermined threshold level, or is elevated relative to the periostin level in one or more control samples. This method can further comprise submitting a second sample taken from the patient for measurement of a second periostin level in the sample. As above, the patient's second periostin level can be measured in an immunoassay employing one or more anti-periostin antibodies or antigen binding fragments thereof which recognize isoforms 1, 2, 3, and 4 of human periostin.

The method further includes increasing or maintaining the amount or frequency of the IL-13 antagonist administered to the patient if the patient's periostin level in the second sample is higher than the periostin level in the first sample, or maintaining or reducing the amount or frequency of the IL-13 antagonist administered to the patient, e.g., a patient identified for treatment of an IL-13-mediated disease or disorder, if the patient's periostin level in the second sample is lower than or about the same as the periostin level in the first sample.

In another aspect, the disclosure provides a method of treating a patient having an IL-13-mediated disease or disorder where the method comprises measuring the periostin level in a first sample obtained from a patient having an IL-13-mediated disease or disorder. Again, the patient's periostin level in the first sample can be measured in an immunoassay employing one or more anti-periostin antibodies or antigen binding fragments thereof which recognize isoforms 1, 2, 3, and 4 of human periostin. The method further includes determining whether the patient's periostin level in the first sample is above a predetermined threshold level, or is elevated relative to the periostin level in one or more control samples and if so, advising a healthcare provider to administer an IL-13 antagonist to the patient. This method can further comprise measuring the periostin level in a second sample obtained from the patient, where again, the patient's periostin level in the second sample can be measured in an immunoassay employing one or more anti-periostin antibodies or antigen binding fragments thereof which recognize isoforms 1, 2, 3, and 4 of human periostin. The method further includes determining whether the patient's periostin level in the second sample is higher than, about the same as, or lower than the periostin level measured in the first sample; and further advising a healthcare provider to increase or maintain the amount or frequency of the IL-13 antagonist administered to the patient if the patient's periostin level in the second sample is higher than the periostin level in the first sample, or to maintain or reduce the amount or frequency of the IL-13 antagonist administered to the patient if the patient's periostin level in the second sample is lower than or about the same as the periostin level in the first sample.

This disclosure further provides a method of monitoring the therapeutic efficacy of an IL-13 antagonist therapeutic regimen in a patient having an IL-13-mediated disease or disorder, where the method includes measuring, or instructing a clinical laboratory to measure, the periostin level in a first sample obtained from a patient having, or suspected of having, an IL-13-mediated disease or disorder. As above, the patient's periostin level is measured in an immunoassay employing one or more anti-periostin antibodies or antigen binding fragments thereof which recognize isoforms 1, 2, 3, and 4 of human periostin. The method further includes administering, or advising a healthcare professional to administer, an IL-13 antagonist to a patient if the patient's periostin level in the first sample is above a predetermined threshold level, or is elevated relative to the periostin level in one or more control samples. The method can further include measuring the periostin level in a second sample obtained from the patient, e.g., in an immunoassay employing one or more anti-periostin antibodies or antigen binding fragments thereof which recognize isoforms 1, 2, 3, and 4 of human periostin, and determining, or obtaining results indicating whether the patient's periostin level in the second sample is higher than, about the same as, or lower than the periostin level measured in the first sample. According to this method, the IL-13 antagonist therapeutic regimen can be considered effective if the patient's periostin level in the second sample is lower than or about the same as the periostin level in the first sample.

In any of the methods provided above, the patient, having, or suspected of having, an IL-13-mediated disease or disorder can be diagnosed with a pulmonary disease, e.g., one or more of asthma, idiopathic pulmonary fibrosis (IPF), chronic obstructive pulmonary disease (COPD), allergic rhinitis, chronic rhinosinusitis, or an inflammatory bowel disease or disorder, e.g., ulcerative colitis (UC). Diagnosis can be accomplished through a differential diagnosis which can include testing for IL-13-mediated diseases or disorders. Measurements for the differential diagnosis can include measuring one or more of: the patient's IgE levels, measuring the patient's eosinophil count, making a symptom analysis, determining the patient's Fraction of Exhaled Nitric Oxide (FENO), determining the patient's Eosinophil/Lymphocyte and Eosinophil/Neutrophil (ELEN) index, or combinations thereof.

This disclosure further provides a method of treating a patient diagnosed with a pulmonary disease or disorder, where the method includes administering an IL-13 antagonist to the patient, e.g., a patient identified as a candidate for treatment, if the periostin level in a sample taken from the patient is above a predetermined threshold level, or is elevated relative to the periostin level in one or more control samples. Again, the patient's periostin level can be measured in an immunoassay employing one or more anti-periostin antibodies or antigen binding fragments thereof which recognize isoforms 1, 2, 3, and 4 of human periostin.

This disclosure further provides a method of treating a patient diagnosed with a pulmonary disease or disorder, where the method includes submitting a first sample taken from the patient for measurement of a first periostin level in the sample, where again the patient's periostin level can be measured in an immunoassay employing one or more anti-periostin antibodies or antigen binding fragments thereof which recognize isoforms 1, 2, 3, and 4 of human periostin. The method further includes administering an IL-13 antagonist to a patient, e.g., a patient identified as a candidate for treatment, if the patient's periostin level in the first sample is above a predetermined threshold level, or is elevated relative to the periostin level in one or more control samples. This method can further include submission of a second sample taken from the patient for measurement of a second periostin level in the sample, which again, can be measured in an immunoassay employing one or more anti-periostin antibodies or antigen binding fragments thereof which recognize isoforms 1, 2, 3, and 4 of human periostin, and increasing or maintaining the amount or frequency of the IL-13 antagonist administered to the patient if the patient's periostin level in the second sample is higher than or about the same as the periostin level in the first sample, or maintaining or reducing the amount or frequency of the IL-13 antagonist administered to the patient if the patient's periostin level in the second sample is lower than the periostin level in the first sample.

The disclosure further provides a method of determining whether to treat a patient diagnosed with a pulmonary disease or disorder with an IL-13 antagonist therapeutic regimen where the method comprises measuring, or instructing a clinical laboratory to measure the periostin level in a first sample obtained from a patient diagnosed with a pulmonary disease or disorder. As above, the patient's periostin level can be measured in an immunoassay employing one or more anti-periostin antibodies or antigen binding fragments thereof which recognize isoforms 1, 2, 3, and 4 of human periostin. The method further includes treating, or instructing a healthcare provider to treat the patient with an IL-13 antagonist therapeutic regimen if the patient's periostin level in the first sample is above a predetermined threshold level, or is elevated relative to the periostin level in one or more control samples.

In any of the methods provided above, the pulmonary disease or disorder can be, e.g., one or more of asthma, idiopathic pulmonary fibrosis (IPF), chronic obstructive pulmonary disease (COPD), allergic rhinitis, chronic rhinosinusitis.

In any of the methods provided above, the IL-13 antagonist can include one or more of an anti-IL-13 antibody or antigen-binding fragment thereof, an IL-13 mutein, an IL-4 mutein, an anti-IL-13Rα1 antibody or antigen-binding fragment thereof, or an anti-IL-4Rα antibody or antigen-binding fragment thereof. In any of the methods provided above, the patient can be on other therapeutic regimens or medications, either before, simultaneously with, or after the treatment or diagnostic methods provided above. Examples of additional medications include, but are not limited to, steroids, e.g., fluticasone or budesonide, a bronchodilator, e.g., salbutamol, or a combination thereof. The one or more additional medications can be administered by inhalation, by oral administration, by injection, or by a combination thereof.

In certain aspects, the IL-13 antagonist is an anti-IL13 antibody, or antigen-binding fragment thereof. In certain aspects the antibody or fragment thereof binds to the same IL-13 epitope as tralokinumab, competitively inhibits binding of tralokinumab to IL-13, or both. In some aspects the antibody or fragment thereof is tralokinumab or an antigen-binding fragment thereof. In certain aspects the antibody or fragment thereof binds to the same IL-13 epitope as lebrikizumab, competitively inhibits binding of lebrikizumab to IL-13, or both. In some aspects the antibody or fragment thereof is lebrikizumab or an antigen-binding fragment thereof.

In certain aspects of the methods provided herein, the patient is an asthma patient, and the sample taken from the patient can be serum. According to this aspect the predetermined threshold periostin level can be, e.g., at least about 15 ng/mL, in the range of about 15 ng/mL to about 25 ng/mL, or at least about 25 ng/mL, or in the range of about 25 ng/mL to about 50 ng/mL, or at least about 50 ng/mL.

In certain aspects of the methods provided herein, the patient is an idiopathic pulmonary fibrosis (IPF) patient, and the sample taken from the patient can be serum. According to this aspect the predetermined threshold periostin level can be, e.g., at least about 40 ng/mL, in the range of about 40 ng/mL to about 60 ng/mL, or at least about 60 ng/mL.

In certain aspects of the methods provided herein, the patient is an ulcerative colitis (UC) patient, and the sample taken from the patient can be serum. According to this aspect the predetermined threshold periostin level can be, e.g., at least about 20 ng/mL, in the range of about 20 ng/mL to about 40 ng/mL, or at least about 40 ng/mL.

In certain aspects of the methods provided herein, the patient is an idiopathic pulmonary fibrosis (IPF) patient, and the sample taken from the patient can be a lung tissue extract. According to this aspect the predetermined threshold periostin level can be, e.g., at least about 5 pg/mg total protein, in the range of about 5 pg/mg total protein to about 10 mg/pg total protein, or to about 25 mg/pg total protein or at least about 10 pg/mg total protein. In certain other aspects of the methods provided herein, the patient is an IPF patient, and the sample taken from the patient can be a lung tissue extract. According to this aspect the predetermined threshold periostin level can be, e.g., at least about 15 pg/mg total protein, in a range of about 15 pg/mg total protein to about 25 pg/mg total protein or at least about 25 pg/mg total protein.

As alluded to above, this disclosure provides a method of measuring periostin levels in a sample obtained from a subject, where the method includes assaying the sample in an immunoassay employing one or more anti-periostin antibodies or antigen binding fragments thereof. In certain aspects, the anti-periostin antibodies recognize isoforms 1, 2, 3, and 4 of human periostin. Anti-periostin antibodies or antigen-binding fragments thereof for use in the methods and/or immunoassays provided herein can include one or more of an isolated antibody or antigen-binding fragment or derivative thereof which binds to the same periostin epitope as monoclonal antibody 4B4.B11 produced from a hybridoma deposited at the American Type Culture Collection (ATCC) under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209. In certain aspects, the isolated antibody or antigen-binding fragment or derivative thereof can competitively inhibit binding of one or more of monoclonal antibodies 4B4.B11 produced from a hybridoma deposited at the ATCC under Deposit No. PTA-120210, 7B5.C4 produced from a hybridoma deposited at the ATCC under Deposit No. PTA-120211, or 3C11.G5 produced from a hybridoma deposited at the ATCC under Deposit No. PTA-120209 to periostin. In certain aspects, each of the one or more anti-periostin antibodies can be an isolated antibody or antigen-binding fragment or derivative thereof that includes a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, where the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, and/or monoclonal antibody 3C11.G5 produced from a hybridoma deposited at the ATCC under Deposit No. PTA-120209. In certain aspects, each of the one or more anti-periostin antibodies can be an isolated antibody or antigen-binding fragment or derivative thereof that includes a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, and/or monoclonal antibody 3C11.G5 produced from a hybridoma deposited at the ATCC under Deposit No. PTA-120209.

In any of the methods provided herein, the patient sample can include one or more of whole blood, serum, plasma, saliva, sputum, bronchoalveolar lavage fluid, lung epithelial cells, or nasal polyps. Moreover, the one or more control samples can be obtained from normal healthy individuals; patients with a non-IL-13-mediated subset of asthma, COPD, IPF, or UC; a pre-determined standard amount of isolated periostin; or a combination thereof. The control samples can be one or more of whole blood, serum, plasma, saliva, sputum, bronchoalveolar lavage fluid, lung epithelial cells, or a combination thereof. In certain aspects, the control sample is matched to the sample taken from the patient.

This disclosure further provides an immunoassay for use in any of the methods provided herein. In certain aspects, the immunoassay can include a sandwich immunoassay, e.g., a sandwich ELISA, which can include a first anti-periostin "capture" antibody or antigen-binding fragment thereof attached to a solid support, and a second anti-periostin "detection" antibody or antigen binding fragment thereof. An immunoassay as provided herein can include attaching a capture antibody or antigen-binding fragment thereof to a solid support; applying the patient sample or control sample under conditions sufficient to allow periostin, if present in the sample, to bind to the capture antibody or antigen-binding fragment thereof; applying the detection antibody or antigen-binding fragment thereof under conditions sufficient to allow binding to periostin already bound to the capture antibody or antigen-binding fragment thereof; and measuring the amount of detection antibody or antigen-binding fragment thereof bound to periostin. According to this aspect, the detection antibody or fragment thereof can include a detectable label, e.g., biotin and/or ruthenium chelate. In certain aspects, the capture antibody can be 3C11.G5 or 7B5.C4, produced by the hybridomas provided herein, and the detection antibody can be 4B4.B11 or 7B5.C4, produced by the hybridomas provided herein. In one aspect, the capture antibody is 7B5.C4 and the detection antibody is 4B4.B11.

Further provided is an isolated antibody or antigen-binding fragment or derivative thereof which can bind to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209. Likewise, the disclosure provides an isolated antibody or antigen-binding fragment or derivative thereof which can competitively inhibit binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin. In a further aspect, the disclosure provides an isolated antibody or fragment or derivative thereof that includes a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209. The disclosure further provides an isolated antibody, or fragment or derivative thereof comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

In certain aspects an isolated antibody fragment as described above can be a Fab fragment, a Fab' fragment, a F(ab')2 fragment, a Fv fragment, or a single chain antibody molecule.

Also provided is a hybridoma that can be the hybridoma deposited at the ATCC under Deposit No. PTA-120210, the hybridoma deposited at the ATCC under Deposit No. PTA-120211, the hybridoma deposited at the ATCC under Deposit No. PTA-120209, or a combination thereof. The disclosure further provides an antibody-producing cell culture that includes the hybridoma deposited at the ATCC under Deposit No. PTA-120210, the hybridoma deposited at the ATCC under Deposit No. PTA-120211, the hybridoma deposited at the ATCC under Deposit No. PTA-120209, or a combination thereof. The antibody or fragment thereof as described above, which can be produced by the hybridoma or the cell culture described above can further comprise a heterologous polypeptide fused thereto or a heterologous moiety conjugated thereto.

Any of the anti-periostin antibodies or fragments thereof provided by this disclosure can further include a heterologous polypeptide fused thereto or a heterologous moiety conjugated thereto. The heterologous polypeptide can be a stabilizing polypeptide, a tag, a label, or a combination thereof, and the heterologous moiety can be one or more of: a peptide, a protein, an enzyme, a lipid, a heterologous antibody or fragment thereof, a detectable label, or polyethylene glycol (PEG). In certain aspects, the heterologous moiety can include biotin or a ruthenium chelate.

In further aspects, the disclosure provides a composition comprising one or more of the antibodies or fragments thereof provided herein. The disclosure further provides a kit for measuring periostin levels in a sample, where the kit contains one or more of the antibodies or fragments thereof provided herein. The kit can further include a solid support and detection reagents. The antibody or antibodies provided in the can be a capture antibody or fragment thereof and/or a detection antibody or fragment thereof. In certain aspects the capture antibody is 7B5.C4 or an antigen-binding fragment thereof and the detection antibody is 4B4.B11 or an antigen-binding fragment thereof. In certain aspects the detection antibody comprises a detectable label, e.g., biotin or ruthenium chelate, and the kit includes detection reagents such as a streptavidin-horse radish peroxidase (HRP) conjugate and a colorimetric substrate for HRP.

This disclosure provides methods and compositions for treating a patient having an IL-13-mediated disease or disorder. The methods provided herein can include administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, 4, 7, and 8 of human periostin.

In another aspect, the disclosure provides a method of treating a patient having an IL-13-mediated disease or disorder, wherein the method can include administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more antiperiostin antibodies or antigen binding fragments thereof which recognize isoforms 1, 2, 3, 4, 7, and 8 of human periostin.

The disclosure further provides a method of treating a patient having an IL-13-mediated disease or disorder, wherein the method can include submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; administering an IL-13 antagonist to the patient if the patient's periostin level in the first sample is above a predetermined threshold level, or is elevated relative to the periostin level in one or more control samples.

The disclosure further provides a method of treating a patient having an IL-13-mediated disease or disorder, wherein the method can include submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; and administering an IL-13 antagonist to the patient identified as a candidate for treatment by having a periostin level in the first sample above a predetermined threshold level, or by having an elevated periostin level relative to a periostin level in one or more control samples.

The disclosure further provides a method of treating a patient having an IL-13-mediated disease or disorder, wherein the method can include measuring the periostin level in a first sample obtained from a patient having an IL-13-mediated disease or disorder, wherein the patient's periostin level in the first sample is measured in an immunoassay employing one or more anti-periostin antibodies or antigen binding fragments thereof which recognize isoforms 1, 2, 3, 4, 7, and 8 of human periostin; determining whether the patient's periostin level in the first sample is above a predetermined threshold level, or is elevated relative to the periostin level in one or more control samples; and advising a healthcare provider to administer an IL-13 antagonist to the patient if the patient's periostin level is above a predetermined threshold level, or is elevated relative to the periostin level in one or more control samples.

The disclosure further provides a method of monitoring the therapeutic efficacy of an IL-13 antagonist therapeutic regimen in a patient having an IL-13-mediated disease or disorder. The method can include measuring, or instructing a clinical laboratory to measure the periostin level in a first sample obtained from a patient having an IL-13-mediated disease or disorder, wherein the patient's periostin level is measured in an immunoassay employing one or more anti-periostin antibodies or antigen binding fragments thereof which recognize isoforms 1, 2, 3, 4, 7, and 8 of human periostin; administering, or advising a healthcare professional to administer an IL-13 antagonist to a patient if the patient's periostin level in the first sample is above a predetermined threshold level, or is elevated relative to the periostin level in one or more control samples; measuring the periostin level in a second sample obtained from the patient, wherein the patient's periostin level in the second sample is measured in an immunoassay employing one or more anti-periostin antibodies or antigen binding fragments thereof which recognize isoforms 1, 2, 3, 4, 7, and 8 of human periostin; and determining, or obtaining results indicating whether the patient's periostin level in the second sample is higher than, about the same as, or lower than the periostin level measured in the first sample; wherein the IL-13 antagonist therapeutic regimen is effective if the patient's periostin level in the second sample is lower than or about the same as the periostin level in the first sample.

The disclosure further provides a method of treating a patient diagnosed with a pulmonary disease or disorder. The method can include administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, 4, 7, and 8 of human periostin.

The disclosure further provides a method of treating a patient diagnosed with a pulmonary disease or disorder, wherein the method can include administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, 4, 7, and 8 of human periostin.

The disclosure further provides a method of treating a patient diagnosed with a pulmonary disease or disorder, wherein the method can include submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; administering an IL-13 antagonist to a patient if the patient's periostin level in the first sample is above a predetermined threshold level, or is elevated relative to the periostin level in one or more control samples.

The disclosure further provides a method of treating a patient diagnosed with a pulmonary disease or disorder, wherein the method can include submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; and administering an IL-13 antagonist to a patient identified as a candidate for treatment by having a periostin level in the first sample above a predetermined threshold level, or by having an elevated periostin level relative to a periostin level in one or more control samples.

The disclosure further provides a method of determining whether to treat a patient diagnosed with a pulmonary disease or disorder with an IL-13 antagonist therapeutic regimen. The method can include measuring, or instructing a clinical laboratory to measure the periostin level in a first sample obtained from a patient diagnosed with a pulmonary disease or disorder, wherein the patient's periostin level is measured in an immunoassay employing one or more anti-periostin antibodies or antigen binding fragments thereof which recognize isoforms 1, 2, 3, 4, 7, and 8 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples.

The disclosure further provides a method of measuring periostin levels in a sample obtained from a subject. The method can include assaying the sample in an immunoassay employing one or more anti-periostin antibodies or antigen binding fragments thereof, wherein the anti-periostin antibodies recognize isoforms 1, 2, 3, 4, 7, and 8 of human periostin.

The disclosure further provides a composition including an antibody or fragment thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

The disclosure further provides a composition including a combination of two or more antibodies or fragments thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

The disclosure further provides a kit for measuring periostin levels in a sample. The kit can include one or more of the antibodies or fragments thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

The disclosure further provides an immunoassay for detecting periostin levels in one or more samples. The immunoassay can include the use of one or more anti-periostin antibodies or antigen-binding fragments thereof, wherein the one or more antibodies or antigen-binding fragments thereof recognize isoforms 1, 2, 3, 4, 7, and 8 of human periostin.

The disclosure further provides a method for determining periostin levels in a test sample. The method provided herein can include (a) contacting the test sample with at least one capture antibody, wherein the capture antibody binds to an epitope on periostin or a fragment of periostin to form a capture antibody-periostin antigen complex; (b) contacting the capture antibody-periostin antigen complex with at least one detection antibody comprising a detectable label, wherein the detection antibody binds to an epitope on periostin that is not bound by the capture antibody and forms a capture antibody-periostin antigen-detection antibody complex; and (c) determining the periostin concentration in the test sample based on the signal generated by the detectable label in the capture antibody-periostin antigen-detection antibody complex formed in (b). The at least one capture antibody comprises the isolated antibody or antibody fragment as described above and the at least one detection antibody comprises the isolated antibody or fragment antibody as described above, and wherein the least one capture antibody is different from the at least one detection antibody.

BRIEF DESCRIPTION OF THE DRAWINGS/FIGURES

FIG. 1: Multiple sequence alignment of the N-terminal domain periostin construct (SEQ ID NO:5) with four endogenously-produced isoforms (SEQ ID NOs 1-4).

Figures 2B, 2C:
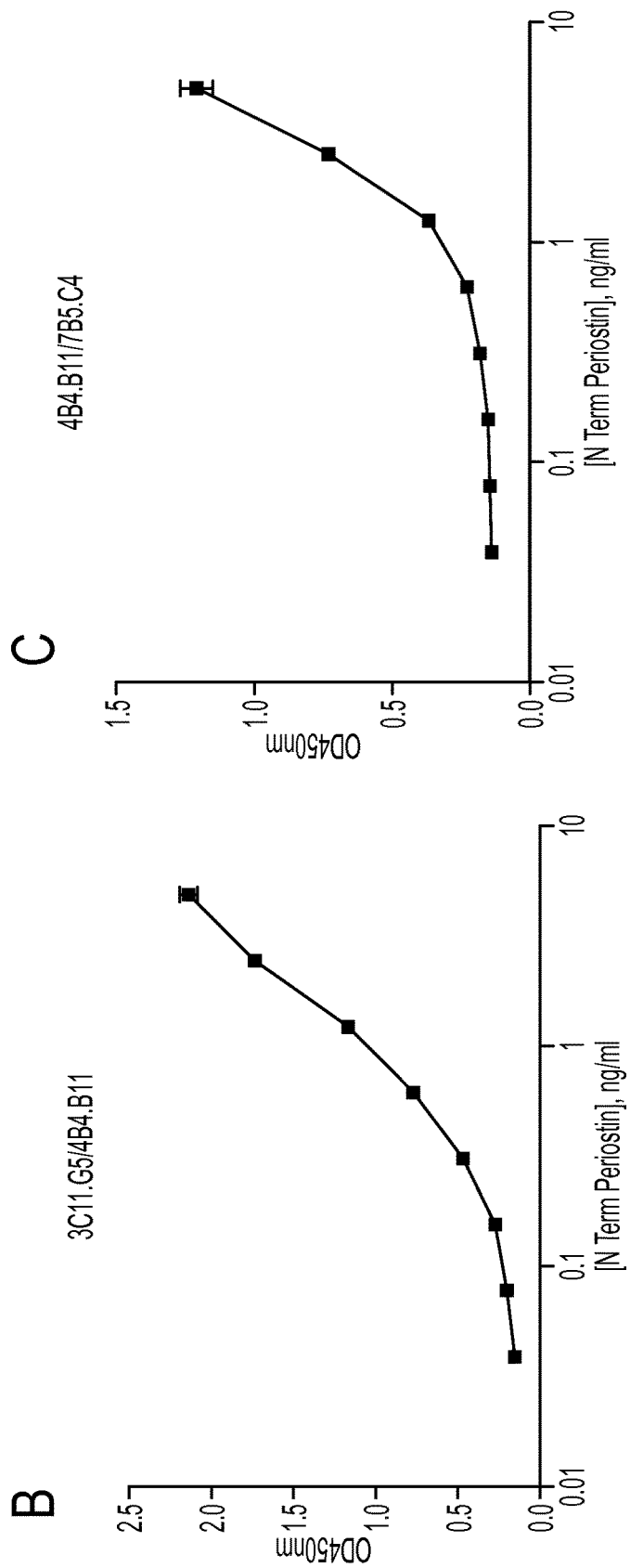

FIGS. 2A-2C: FIG. 2A. Binding specificity of 7B5.C4, 4B4.B11, and 3C11.G5 mAbs, as determined in the ECL immunoassay. FIGS. 2B and 2C: Specificity of the binding of 7B5.C4, 4B4.B11, and 3C11.G5 mAbs to the common N-terminal fragment of human periostin as determined in the biotin/streptavidin-HRP sandwich ELISA assay using 3C11.G5 as the capture antibody and biotinylated 4B4.B11 as the detection antibody (FIG. 2B) or 4B4.B11 as the capture antibody and biotinylated 7B5.C4 as the detection antibody (FIG. 2C).

FIGS. 3A-3C: FIG. 3A. Schematic of the assay used to determine relative binding specificities of 7B5.C4, 4B4.B11, and 3C11.G5. FIG. 3B. Graph showing results of competition assay showing the % maximal response observed with Ru-labeled 3C11.G5 when increasing amounts of unlabeled 7B5.C4, 4B4.B11 and 3C11.G5 mAbs were added. FIG. 3C. Diagram showing the relative binding specificities of the 7B5.C4, 4B4.B11, and 3C11.G5 mAbs.

Figures 4A, 4B:
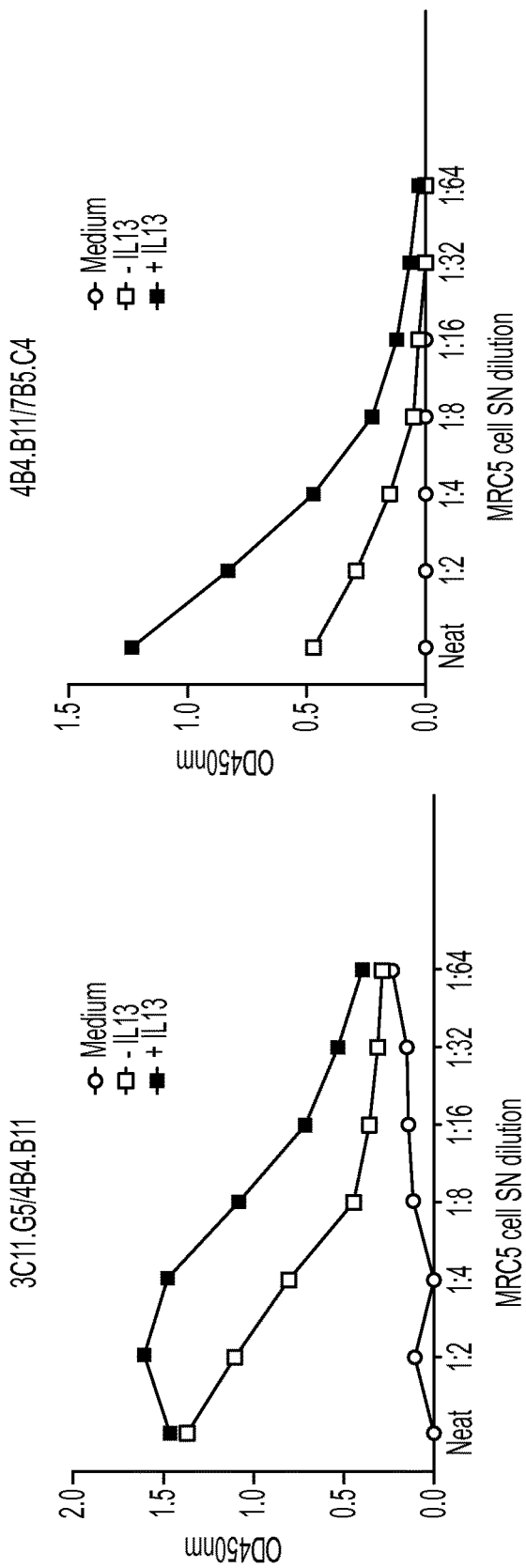

FIGS. 4A and 4B: Detection of spontaneous and IL-13-induced periostin in MRC5 cell supernatants in the biotin/streptavidin-HRP sandwich ELISA assay using 3C11.G5 as the capture antibody and biotinylated 4B4.B11 as the detection antibody (FIG. 4A), or 4B4.B11 as the capture antibody and biotinylated 7B5.C4 as the detection antibody (FIG. 4B).

Figure 5A:
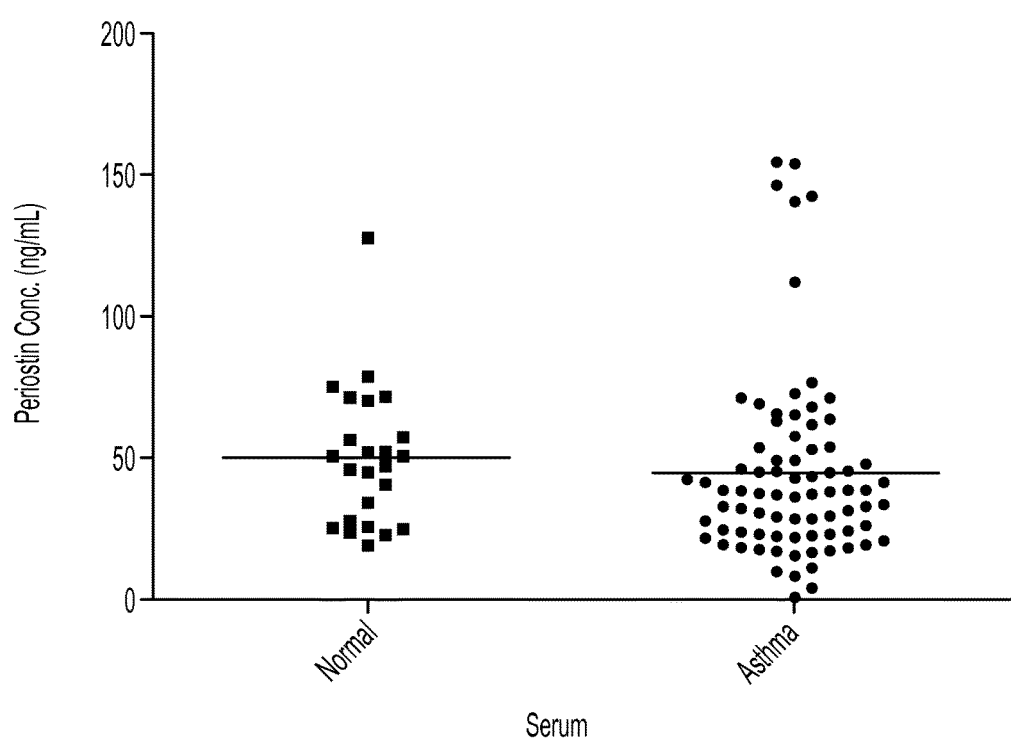
Figure 5B:
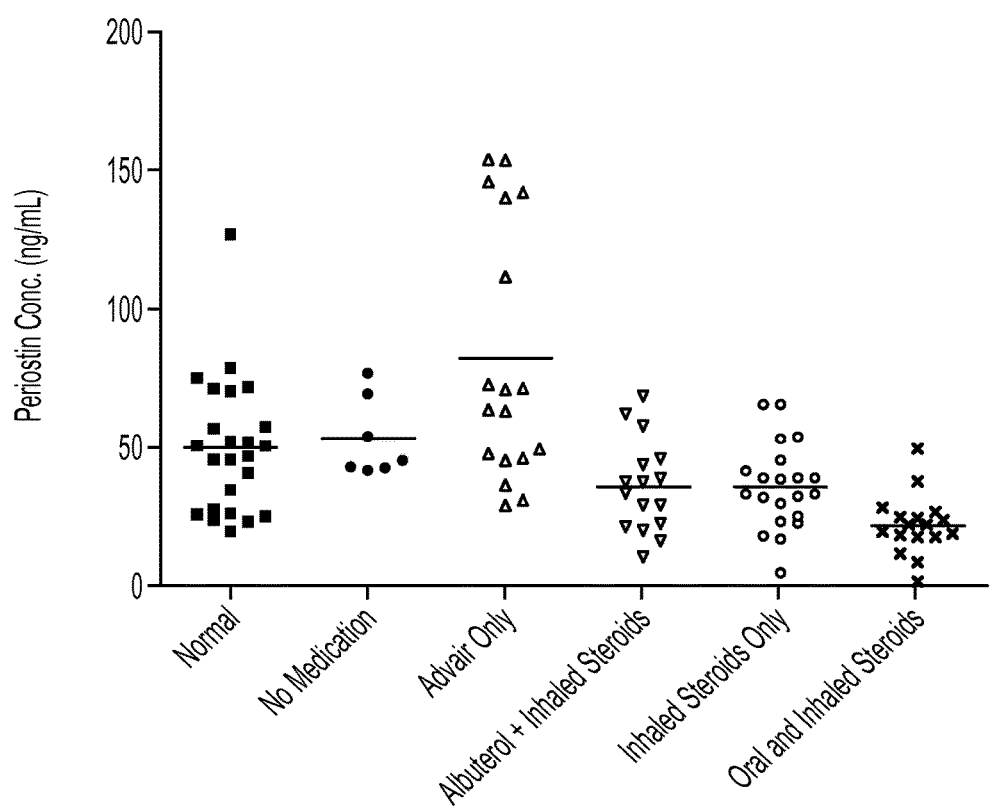

FIGS. 5A-5B: FIG. 5A. Detection of periostin levels in serum samples from asthma patients and normal human donors. Periostin levels were determined using the biotin/streptavidin-HRP sandwich ELISA assay using 4B4.B11 as the capture antibody and biotinylated 7B5.C4 as the detection antibody. FIG. 5B. Same results as in FIG. 5A, but with the asthma patients broken down into groups based on medication status. The lines in the scatter plots of both panels indicate the mean periostin levels.

Figure 6:
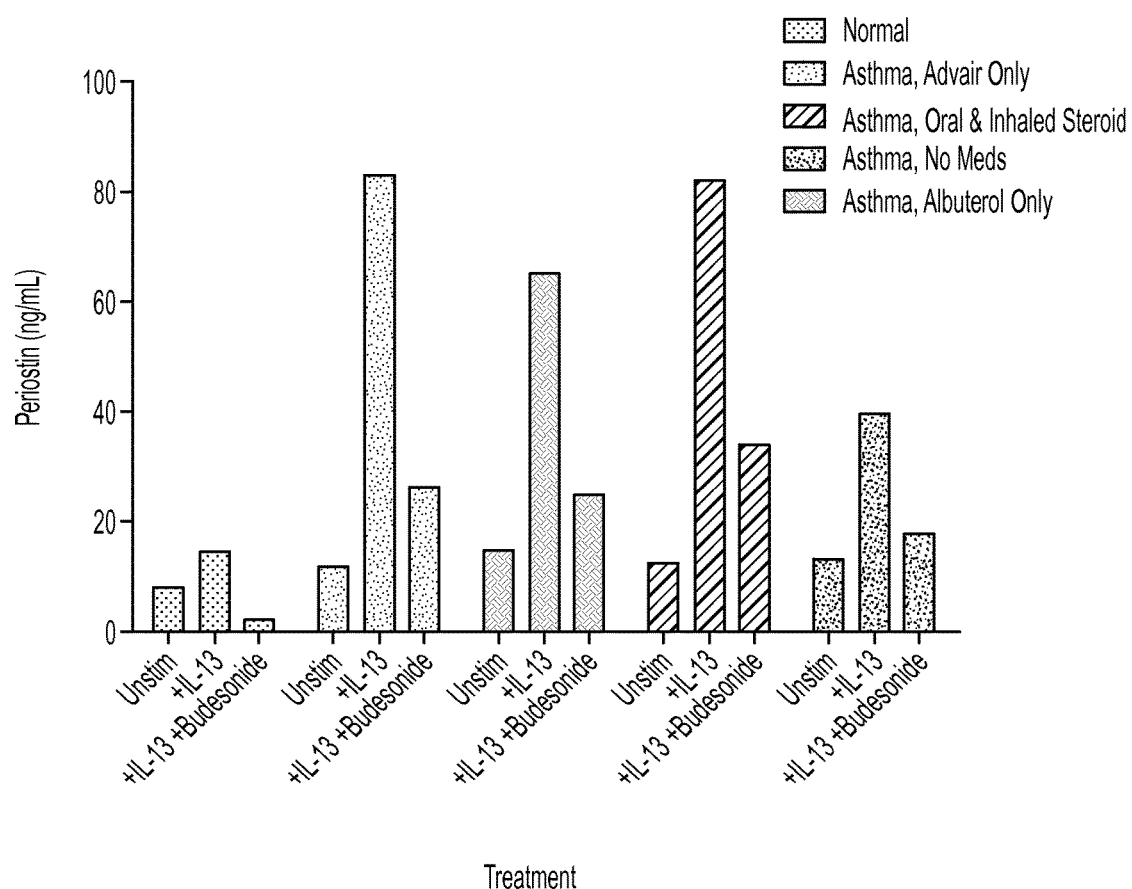

FIG. 6: Periostin levels in IL-13 Stimulated EPIAIRWAY™ Models (Normal and Asthmatic Lung Epithelium). Detection of periostin levels in EPIAIRWAY™ tissue obtained from either normal healthy individuals or from asthma patients each receiving different treatments: Advair only; oral and inhaled steroids; no medication; or albuterol only. Periostin levels were determined using the biotin/streptavidin-HRP sandwich ELISA assay using 4B4.B11 as the capture antibody and biotinylated 7B5.C4 as the detection antibody. Samples receiving steroid were pre-treated for 6 hrs with 100 nM budesonide. Samples were either unstimulated or stimulated with 50 ng/mL IL-13±budesonide for 48 hours. Periostin levels increase following stimulation with IL-13. This increase is reduced with steroid treatment.

Figures 7A, 7B:
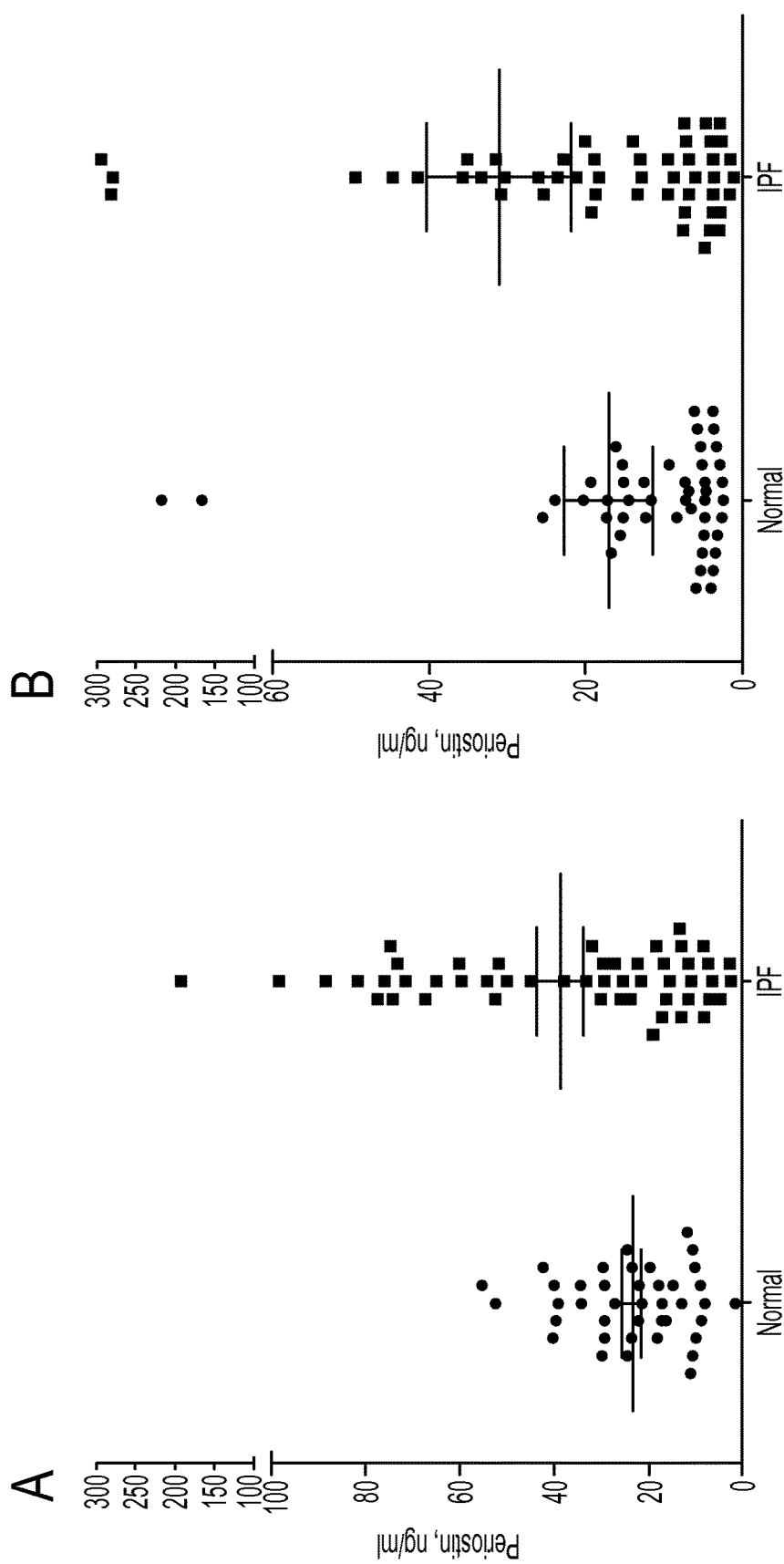
Figures 7C, 7D:
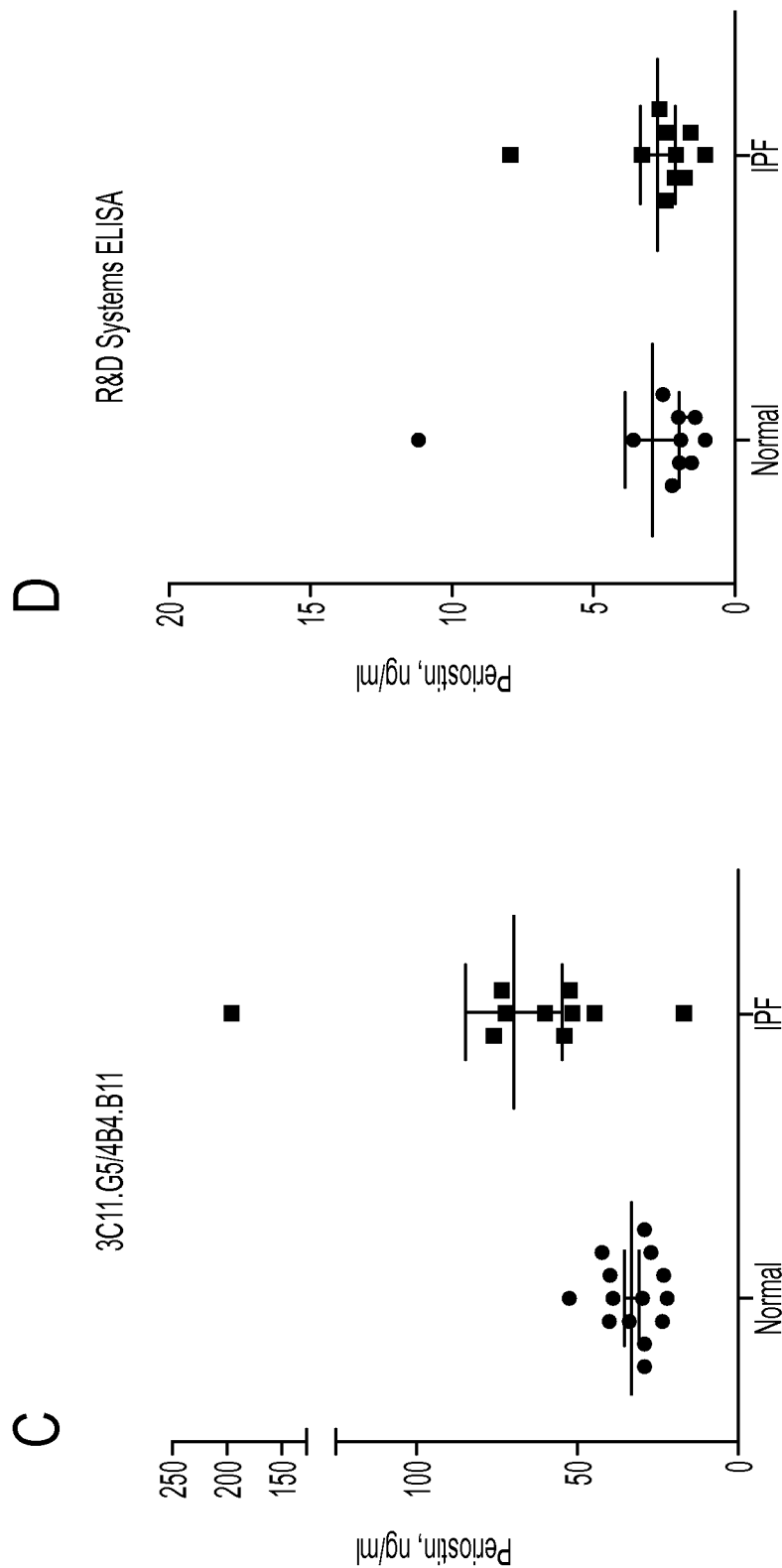

FIGS. 7A-7D: FIGS. 7A-7B. Detection of periostin levels in serum samples from IPF patients and normal human donors. Periostin levels were determined using the biotin/streptavidin-HRP sandwich ELISA assay using 3C11.G5 as the capture antibody and biotinylated 4B4.B11 as the detection antibody (FIG. 7A), or 4B4.B11 as the capture antibody and biotinylated 7B5.C4 as the detection antibody (FIG. 7B). FIGS. C-D. Comparison of the biotin/streptavidin-HRP assay using 3C11.G5 as the capture antibody and biotinylated 4B4.B11 as the detection antibody in a subset of IPF and normal serum samples (FIG. 7C) to a commercially available periostin assay (Human Periostin/OSF-2 DuoSet, Catalog No. DY3548, available from R & D Systems) (FIG. 7D). The lines in the scatter plots of the panels indicate the mean periostin levels.

Figure 8:
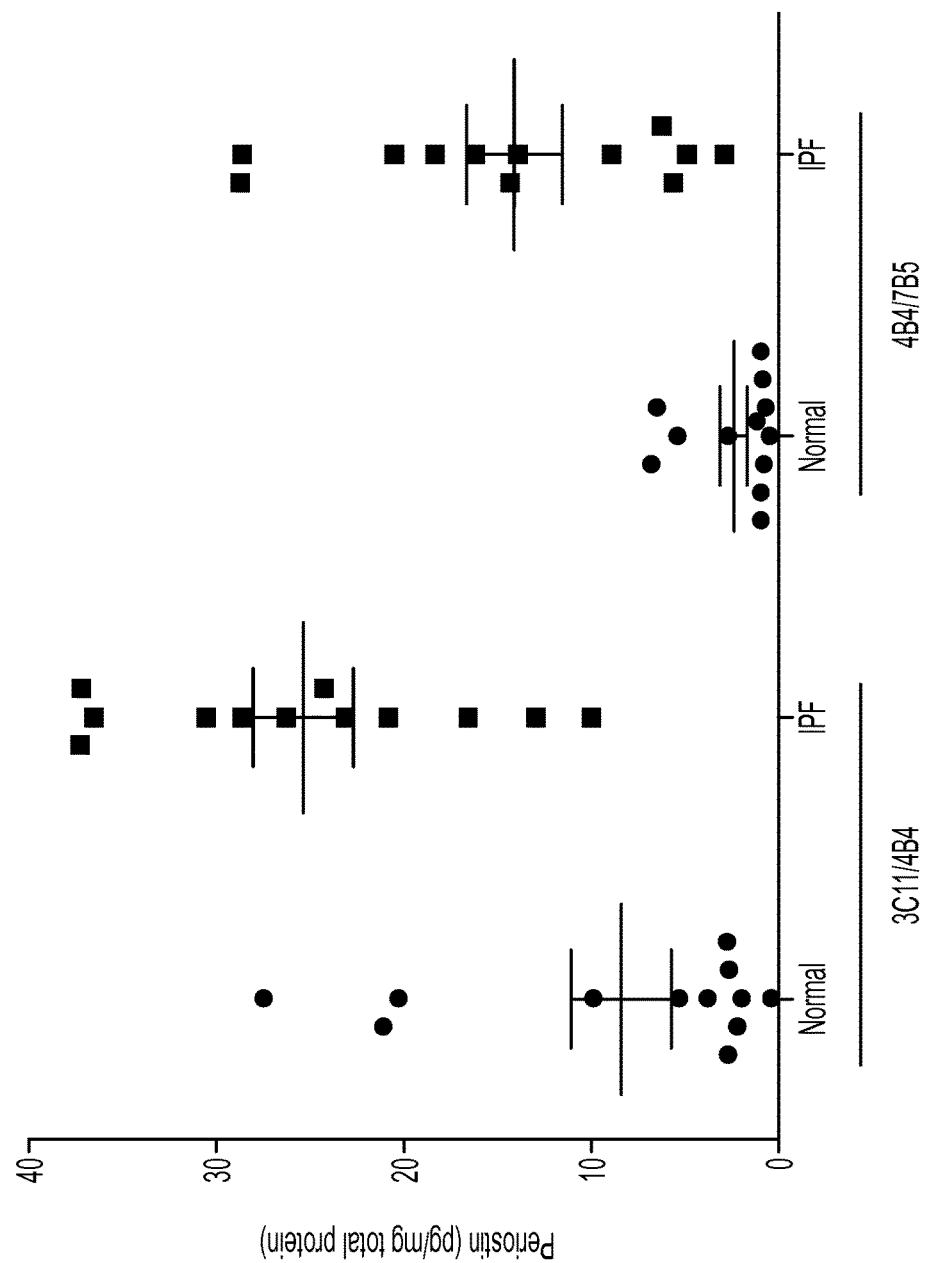

FIG. 8: Detection of periostin protein in IPF lung extracts using the Biotin/Avidin ELISA assay with either 3C11.G5 as the capture antibody and biotinylated 4B4.B11 as the detection antibody, or 4B4.B11 as the capture antibody and biotinylated 7B5.C4 as the detection antibody. The lines in the scatter plots of both panels indicate the mean periostin levels.

Figure 9:
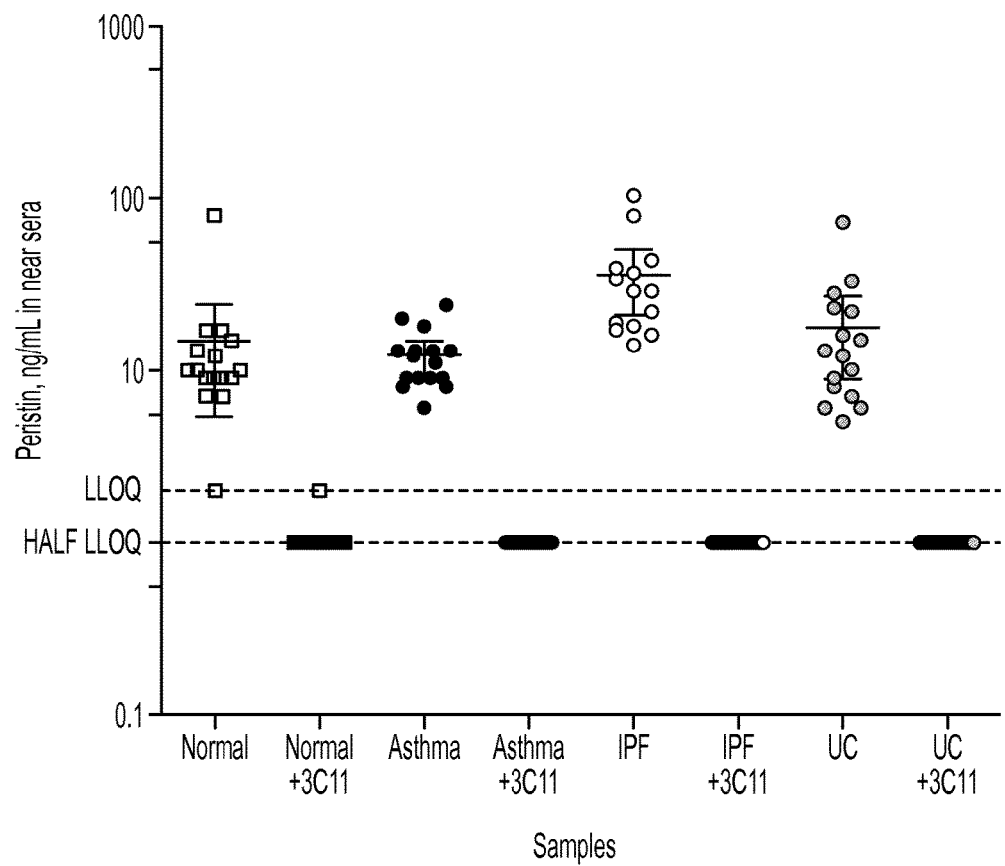

FIG. 9: Determination of assay specificity in serum from normal donors and patients with asthma, IPF, or UC. The MSD assay was used with 7B5.C4 as the capture antibody and Ru-labeled 4B4.B11 as the detection antibody. Periostin concentrations were determined in the presence and absence of spiked 3C11 antibody, a competitive inhibitor of 7B5.C4. The mean±95% Confidence Interval for each population is plotted. LLOQ=lower limit of quantitation (2 ng/mL).

Figure 10A:
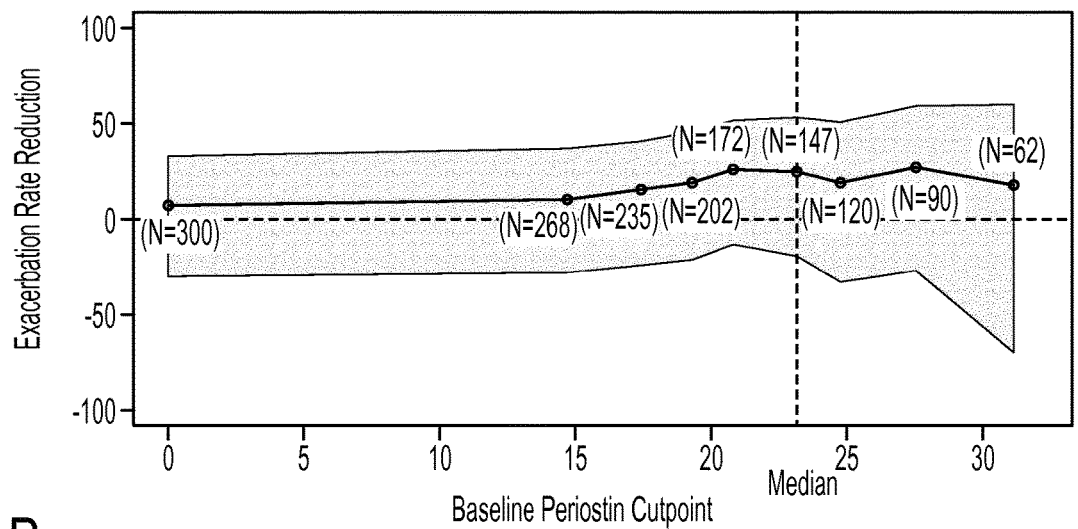
Figure 10B:
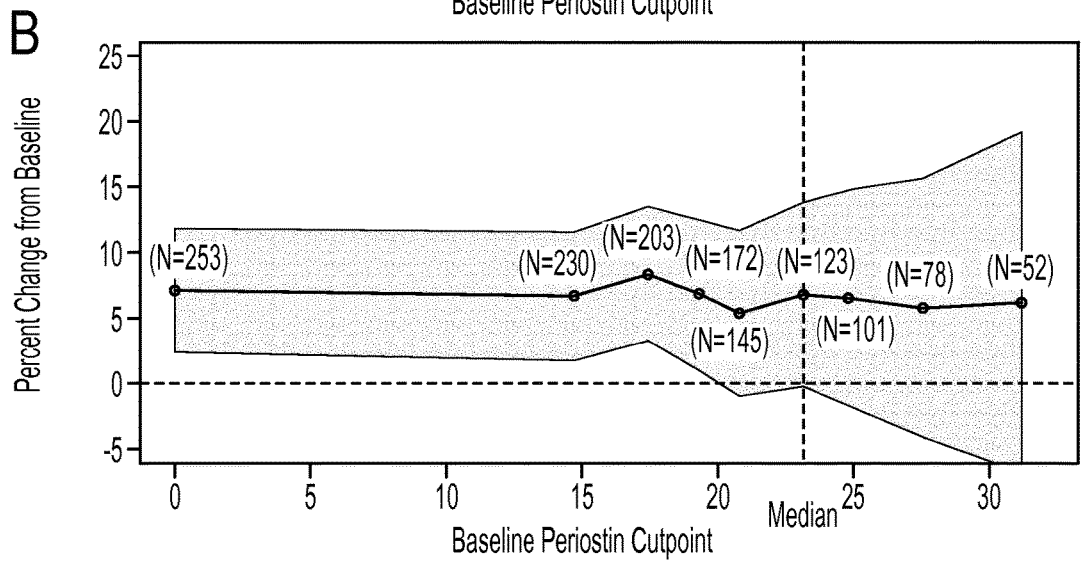

FIGS. 10A-10B: asthma exacerbation rate (AER) reduction and mean percent change from baseline in pre-bronchodilator FEV1 at Week 53 for patients by baseline serum periostin level (Tralokinumab vs. Placebo). FIG. 10A is a continuous representation of AER reduction (95% CI) by serum periostin level in asthma patients treated with Tralokinumab showing the patients' median periostin value and the effect of changing the median periostin value (baseline periostin cutpoint) on AER Reduction at week 53. FIG. 10B is a continuous representation of percent change from baseline in pre-bronchodilator FEV1 (95% CI) by serum periostin level in asthma patients treated with Tralokinumab showing the patients' median periostin value and the effect of changing the median periostin value (baseline periostin cutpoint) on the percent change from baseline in pre-bronchodilator FEV1 at Week 53. Q2W=every 2 weeks; AER=Asthma Exacerbation Rate; FEV1=forced expiratory volume in 1 second; CI=confidence interval.

Figure 11A:
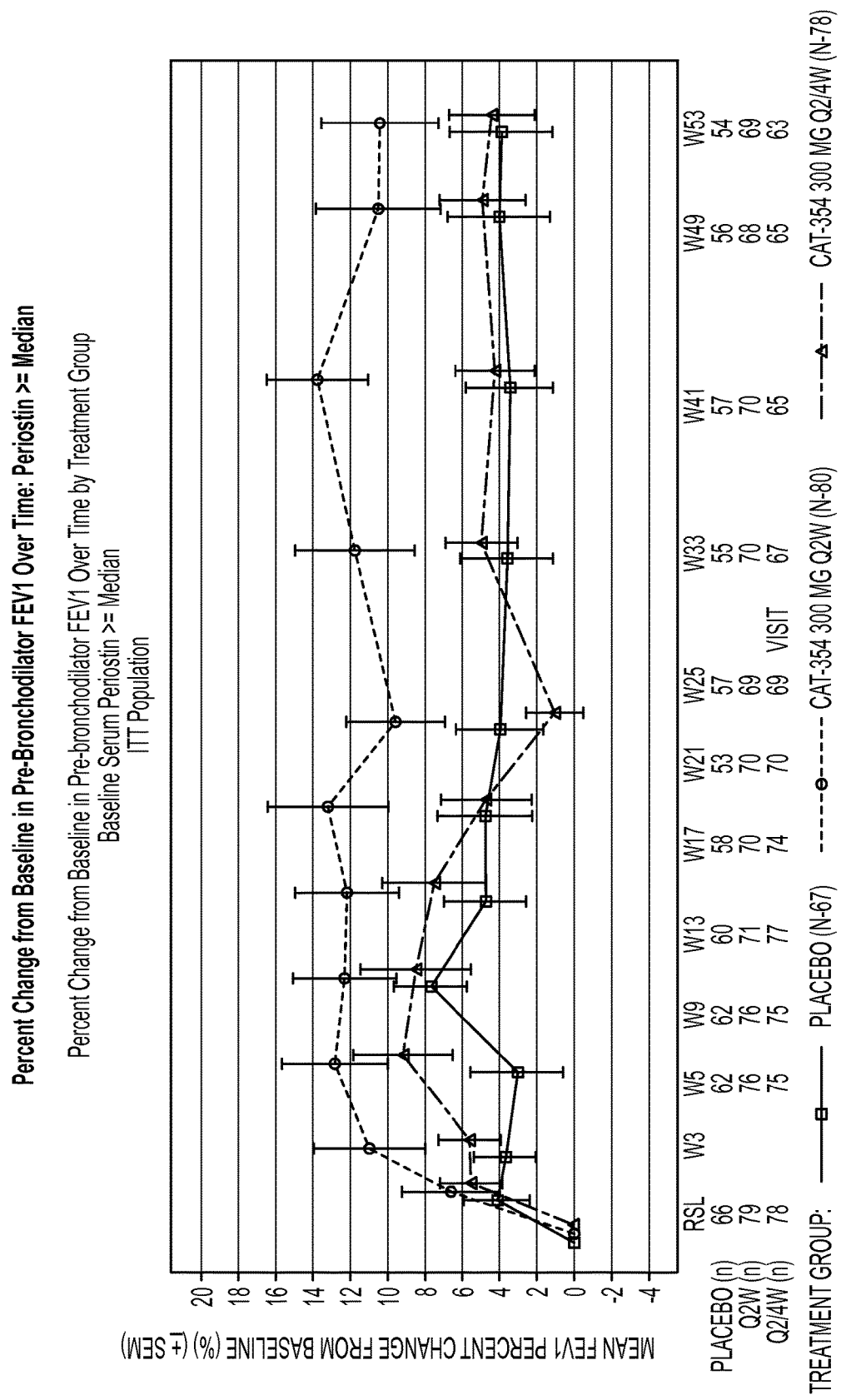

FIG. 11A: percent change from baseline in pre-bronchodilator FEV1 over time when periostin >=median in patients treated with Tralokinumab. Relative increases in FEV1 were observed in the 300 mg Tralokinumab Q2W group through to Week 53 in patients having periostin levels >=median. FEV1=forced expiratory flow in one second; ITT=intent to treat; Q2W=every 2 weeks; Q2/4W=2 injections Q2W for 12 weeks followed by Q4W for 38 weeks; CAT-354=tralokinumab.

Figure 11B:
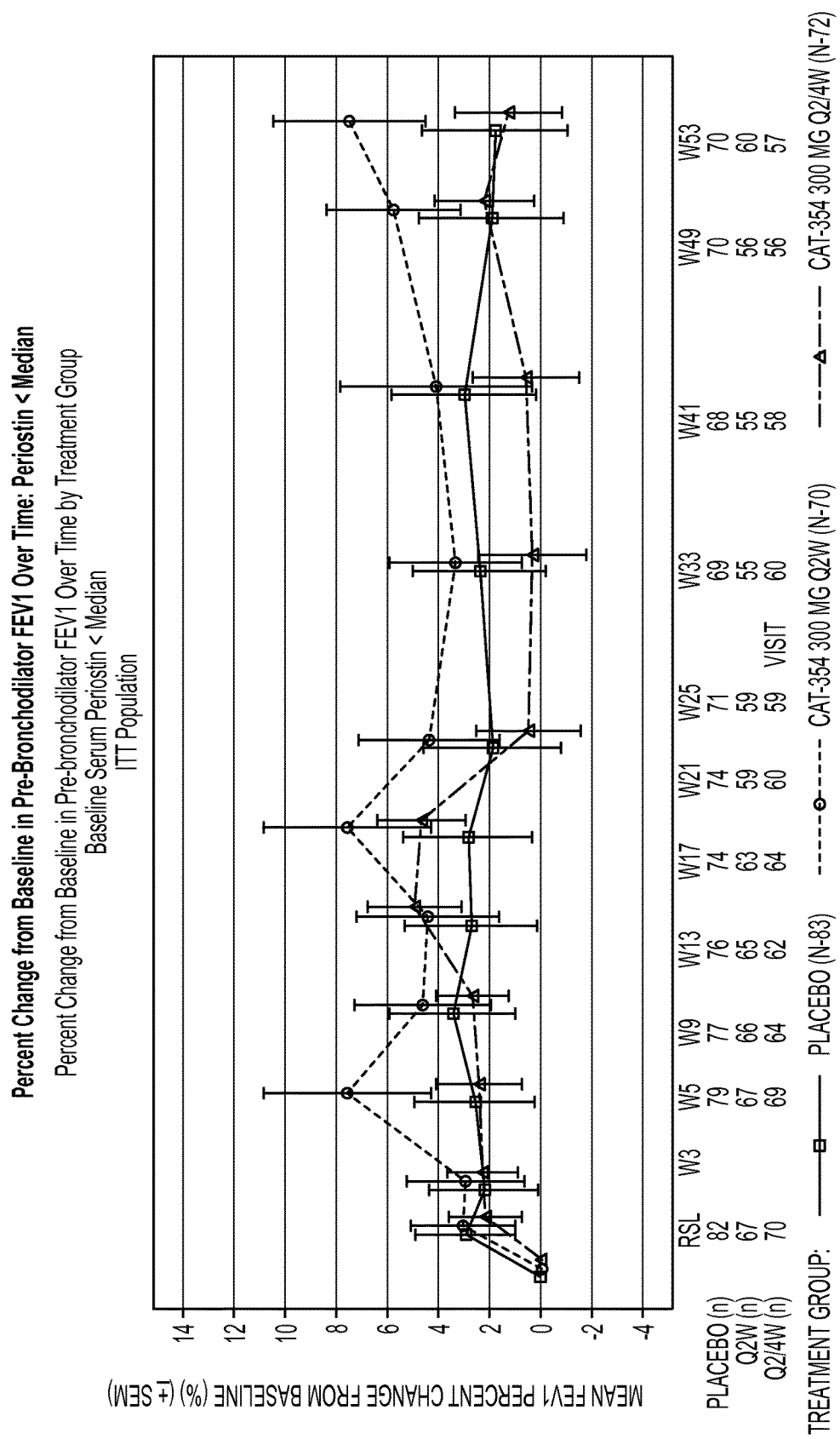

FIG. 11B: percent change from baseline in pre-bronchodilator FEV1 over time when periostin <median in patients treated with Tralokinumab. No significant increases in FEV1 were observed in the 300 mg Tralokinumab Q2W group or the Q2/4W through to Week 53. FEV1=forced expiratory flow in one second; ITT=intent to treat; Q2W=every 2 weeks; Q2/4W=2 injections Q2W for 12 weeks followed by Q4W for 38 weeks; CAT-354=tralokinumab.

FIG. 12: exon map for periostin isoforms 2, 3, 4, 7, and 8, relative to isoform 1.

Figure 13:
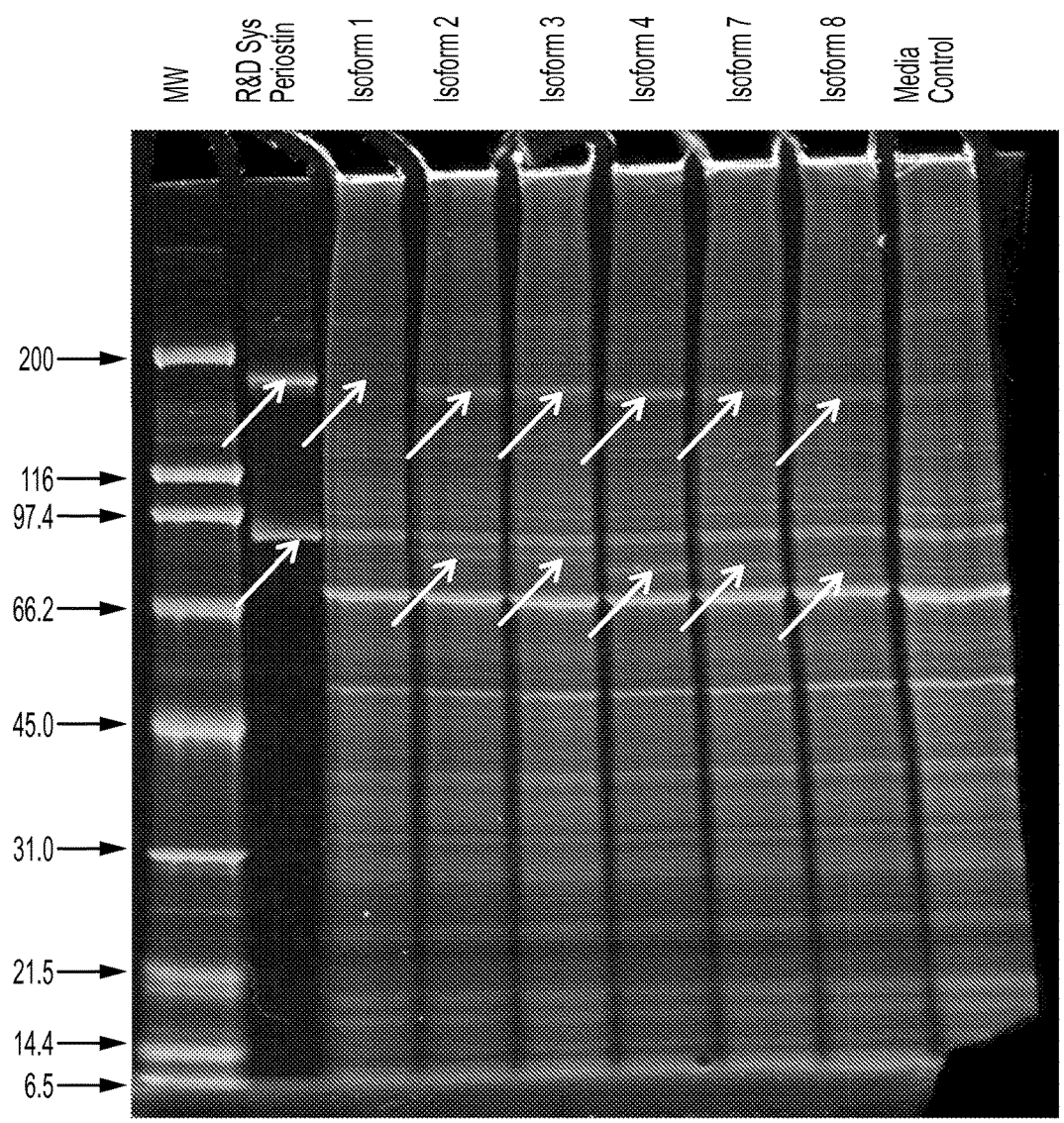

FIG. 13: non-denaturing SDS-PAGE gel of periostin isoforms.

Figure 14A:
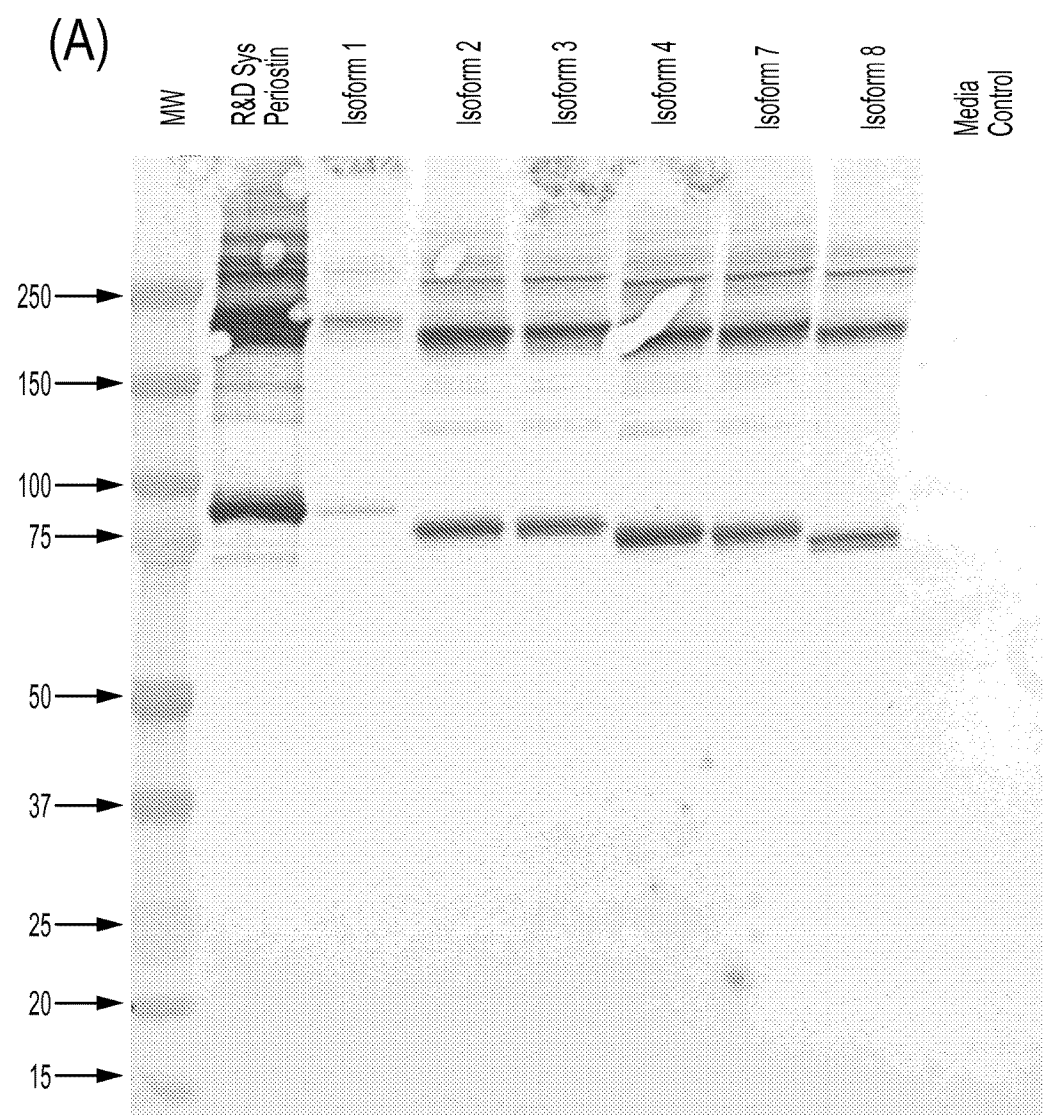
Figure 14B:
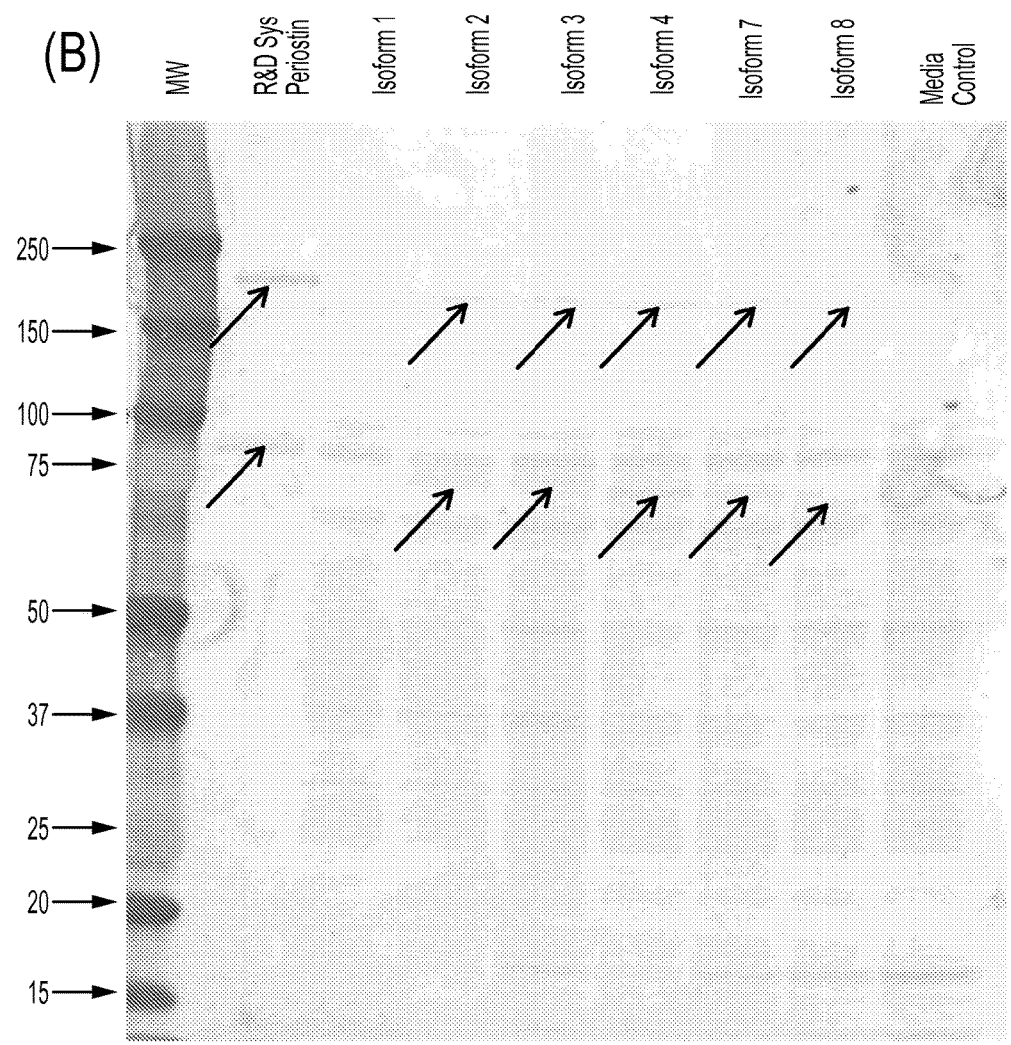

FIGS. 14A-14B: Western blot of antibodies (FIG. 14A) 4B4.B11 and (FIG. 14B) 7B5.C4 binding to periostin isoforms.

Figure 15:
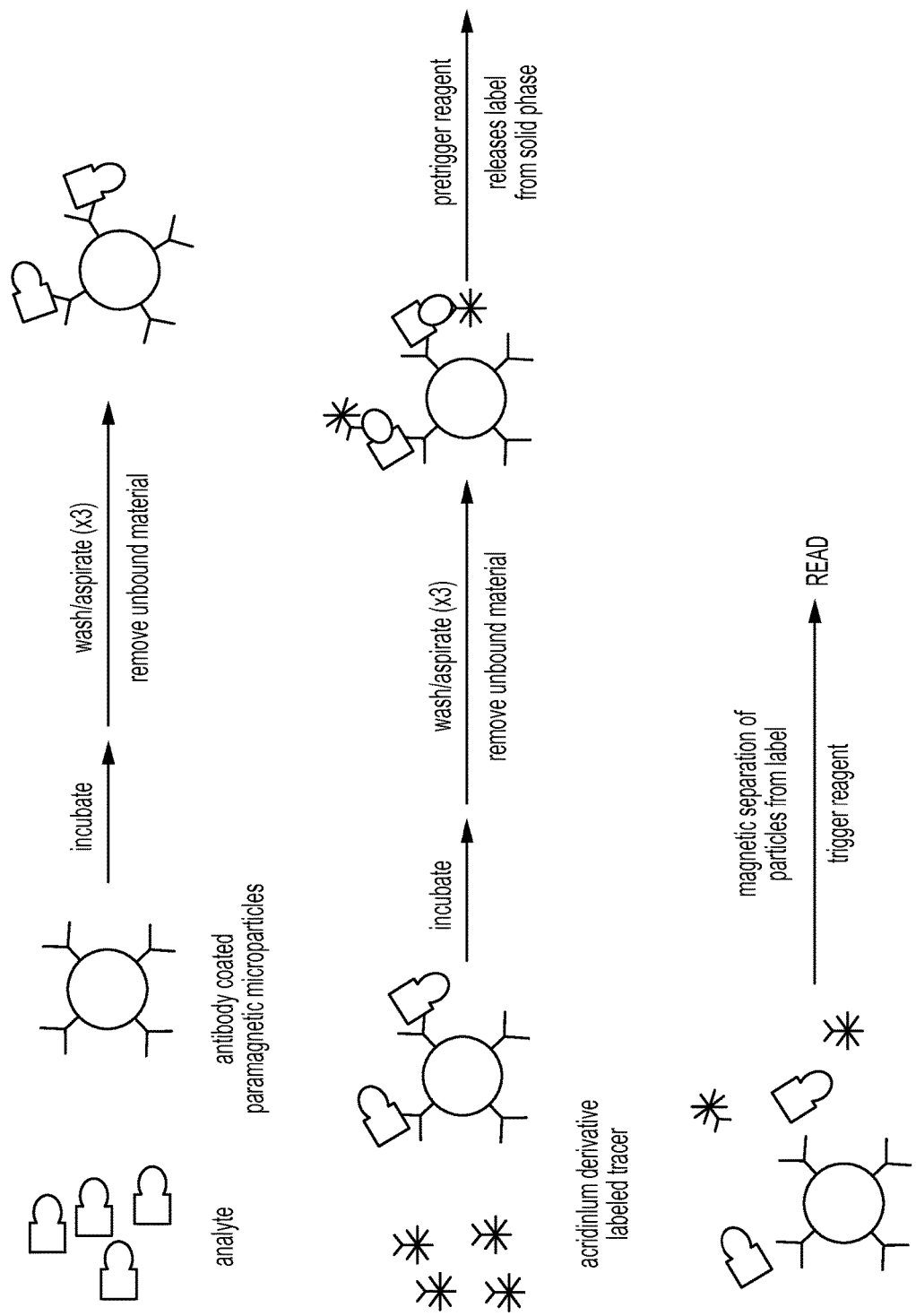

FIG. 15: schematic of the ARCHITECT® sandwich immunoassay principle.

DETAILED DESCRIPTION

The present disclosure provides methods and systems for diagnosing and treating a subject as having an IL-13-mediated disease or disorder, comprising administering an IL-13 antagonist to the patient if the periostin level in a sample taken from the patient is above a predetermined threshold level, or is elevated relative to the periostin level in one or more control samples.

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

The term "about" as used in connection with a numerical value throughout the specification and the claims denotes an interval of accuracy, familiar and acceptable to a person skilled in the art. In general, such interval of accuracy is ±10%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The term "periostin," as used herein refers to the periostin protein, also known as osteoblast-specific factor 2 (OSF-2). A total of 23 exons have been identified in the full length isoform 1, and human periostin exists in at least six isoforms: 1, 2, 3, 4, 7, and 8. An exon map for all isoforms is shown in FIG. 12, and the lengths and molecular weights of isoforms 1, 2, 3, 4, 7, and 8 are shown in Table 1. Exons 1-17 and 22-23 are conserved between all isoforms, but the region containing exons 17-21 is variable. In particular, the term refers to any mammalian periostin, for example, isoforms 1, 2, 3 and 4 of a mammalian periostin. For example, the term "periostin" may refer to isoforms 1, 2, 3, 4, 7, and 8 of a mammalian periostin. In certain aspects, periostin is human periostin. Human periostin exists in at least four isoforms 1, 2, 3 and 4, comprising the following amino acid sequences: NP_006466.2 (SEQ ID NO:1); NP_001129406.1 (SEQ ID NO:2), NP_001129407.1 (SEQ ID NO:3), and NP_001129408.1 (SEQ ID NO:4), respectively, according to the NCBI database. Human periostin may also exist as isoforms 7 and 8, comprising the following amino acid sequences SEQ ID NO:16, and SEQ ID NO: 17. The common N-terminal region of the four mature human periostin isoforms listed above is also shown in FIG. 1, and is presented herein as SEQ ID NO:5. The N-terminal signal sequence facilitates secretion from the cell. The Periostin isoforms 1, 2, 3, 4, 7, and 8 are encoded by polynucleotide sequences SEQ ID NOs: 10-15. It has been discovered that 5 isoforms exist in normal lung tissue: isoforms 2, 3, 4, 7, and 8 (Morra et al. Lung Cancer. 2012. 76(2):183-190).

TABLE 1

Periostin isoforms.

| Isoform | Amino Acids | MW (without signal peptide |
|---------|-------------|----------------------------|
| 1 | 829 | 92492 |
| 2 | 772 | 86199 |
| 3 | 774 | 86432 |
| 4 | 744 | 83028 |
| 7 | 742 | 82676 |
| 8 | 712 | 79289 |

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like.

As indicated above, the variable region allows the binding molecule to selectively recognize and specifically bind epitopes on antigens. That is, the VL domain and VH domain, or a subset of the complementarity determining regions (CDRs), of an antibody combine to form the variable region that defines a three-dimensional antigen-binding site. This quaternary binding molecule structure forms the antigen-binding site present at the end of each arm of the Y. More specifically, the antigen-binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the cases where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al, J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that an antibody or fragment, variant, or derivative thereof binds to an epitope via its antigen-binding domain, and that the binding entails some complementarity between the antigen binding domain and the epitope. According to this definition, an antibody is said to "specifically bind" to an epitope when it binds to that epitope via its antigen-binding domain more readily than it would bind to a random, unrelated epitope.

An antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

Antibodies or antigen-binding fragments, variants, or derivatives thereof disclosed herein can be described or specified in terms of the epitope(s) or portion(s) of an antigen, e.g., a target polysaccharide that they recognize or specifically bind. For example, the portion of human periostin that specifically interacts with the antigen-binding domain of an antibody provided in this disclosure is an "epitope."

As used herein, the term "IL-13-mediated disease or disorder" refers to any pathology caused by (alone or in association with other mediators), exacerbated by, associated with, or prolonged by abnormal levels of IL-13 in the subject having the disorder. In some embodiments, the IL-13-mediated disease or disorder may be a pulmonary disease or disorder, a chronic inflammatory skin disease or disorder, an inflammatory bowel disease or disorder. Non-limiting examples of IL-13-mediated diseases or disorders include asthma, idiopathic pulmonary fibrosis (IPF), chronic obstructive pulmonary disease (COPD), ulcerative colitis (UC), allergic rhinitis, or chronic rhinosinusitis. A non-limiting example of a IL-13-mediated disease or disorder includes atopic dermatitis.

As used herein, the term "pulmonary disease or disorder" refers to any pathology affecting at least in part the lungs or respiratory system. Non-limiting examples include asthma, IPF, COPD, allergic rhinitis, or chronic rhinosinusitis. In certain aspects, the pulmonary disease or disorder is IL-13-mediated.

The term "asthma" refers to diseases that present as reversible airflow obstruction and/or bronchial hyper-responsiveness that may or may not be associated with underlying inflammation. Examples of asthma include allergic asthma, atopic asthma, corticosteroid naive asthma, chronic asthma, corticosteroid resistant asthma, corticosteroid refractory asthma, asthma due to smoking, asthma uncontrolled on corticosteroids and other asthmas as mentioned, e.g., in the Expert Panel Report 3: Guidelines for the Diagnosis and Management of Asthma, National Asthma Education and Prevention Program (2007) ("NAEPP Guidelines"), incorporated herein by reference in its entirety.

The term "COPD" as used herein refers to chronic obstructive pulmonary disease. The term "COPD" includes two main conditions: emphysema and chronic obstructive bronchitis.

The term "Idiopathic Pulmonary Fibrosis" (IPF) refers to a disease characterized by progressive scarring, or fibrosis, of the lungs. It is a specific type of interstitial lung disease in which the alveoli gradually become replaced by fibrotic tissue. With IPF, progressive scarring causes the normally thin and pliable tissue to thicken and become stiff, making it more difficult for the lungs to expand, preventing oxygen from readily getting into the bloodstream. See, e.g., Am. J. Respir. Crit. Care Med. 2000. 161:646-664.

The term "Ulcerative colitis" (UC) refers to an inflammatory disorder of the gastrointestinal (GI) tract that affects the colorectum which includes characteristic ulcers, or open sores. UC is an intermittent disease, with periods of exacerbated symptoms, and periods that are relatively symptom-free. Symptom of active disease include constant diarrhea mixed with blood that persists for an extended period (weeks), weight loss, chronic loss of blood from the GI tract, anaemia, abdominal pain, and mild discomfort to painful bowel movements or painful abdominal cramping with bowel movements. See, e.g., Danese, et al. N Engl J Med. 2011 365 (18) :1713-25.

The term "chronic inflammatory skin disease or disorder" refers to any pathology affecting at least in part the skin. Non-limiting examples include atopic dermatitis, skin fibrosis, allergic contact dermatitis, eczema, or psoriasis.

As used herein the terms "treat, " "treatment, " or "treatment of" (e.g., in the phrase "treating a patient having an IL-13-mediated disease or disorder") refers to reducing the potential for an IL-13-mediated disease or disorder, reducing the occurrence of the IL-13-mediated disease or disorder, and/or a reduction in the severity of the IL-13-mediated disease or disorder, preferably, to an extent that the subject no longer suffers discomfort and/or altered function due to it (for example, a relative reduction in asthma exacerbations when compared to untreated patients). For example, treating can refer to the ability of a therapy when administered to a subject, to prevent an IL-13-mediated disease or disorder from occurring and/or to cure or to alleviate IL-13-mediated disease symptoms, signs, or causes. Treating also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

The present disclosure provides methods and systems providing therapeutic benefit in the treatment of an IL-13-mediated disease or disorder. A therapeutic benefit is not necessarily a cure for a particular IL-13-mediated disease or disorder, but rather encompasses a result which most typically includes alleviation of the IL-13-mediated disease or disorder or increased survival, elimination of the IL-13-mediated disease or disorder, reduction of a symptom associate with the IL-13-mediated disease or disorder, prevention or alleviation of a secondary disease, disorder or condition resulting from the occurrence of a primary IL-13-mediated disease or disorder, and/or prevention of the IL-13-mediated disease or disorder.

The terms "subject" or "patient" as used herein refer to any subject, particularly a mammalian subject, for whom diagnosis, prognosis, or therapy of an IL-13-mediated disease or disorder is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having an IL-13-mediated disease or disorder" includes subjects, such as mammalian subjects, that would benefit from the administration of a therapy, imaging or other diagnostic procedure, and/or preventive treatment for that IL-13-mediated disease or disorder.

In some aspects of the present disclosure, a subject is a naïve subject. A naïve subject is a subject that has not been administered a therapy, for example a therapeutic agent. In some aspects, a naïve subject has not been treated with a therapeutic agent prior to being diagnosed as having an IL-13-mediated disease or disorder, for example, asthma, IFP, COPD, or UC. In some aspects, a naïve subject has not been treated with a therapeutic agent prior to being diagnosed as having an IL-13-mediated disease or disorder, for example, atopic dermatitis. In another aspect, a subject has received therapy and/or one or more doses of a therapeutic agent (e.g., a therapeutic agent capable of modulating an inflammatory response associated with an IL-13-mediated disease or disorder, a pulmonary disease or disorder, or an inflammatory bowel disease or disorder) prior to being diagnosed as having an IL-13-mediated disease or disorder. In another aspect, a subject has received therapy and/or one or more doses of a therapeutic agent (e.g., a therapeutic agent capable of modulating an inflammatory response associated with an IL-13-mediated disease or disorder, a pulmonary disease or disorder, an inflammatory bowel disease or disorder, or a chronic inflammatory skin disease or disorder) prior to being diagnosed as having an IL-13-mediated disease or disorder. In one aspect, the therapeutic agent is a small molecule drug. In a specific aspect, the agent is a corticosteroid. In another aspect, the agent can be a leukotriene modifier such as montelukast, zafirlukast or zileuton. In a further aspect, the therapeutic agent can be a methylxanthine (e.g., theophylline) or a cromone (e.g., sodium cromolyn and nedocromil). In another aspect, the therapeutic agent can be a long-acting beta-2 agonist such as salmeterol, fomoterol, or indacaterol. In a further aspect, the agent can be methotrexate or cyclosporin.

In certain aspects, the therapeutic agent can be an agent used for preventing, treating, managing, or ameliorating asthma. Non-limiting examples of therapies for asthma include anti-cholinergics (e.g., ipratropium bromide and oxitropium bromide), beta-2 antagonists (e.g., albuterol (PROVENTIL® or VENTOLIN®), bitolterol (TOMALATE®), fenoterol, formoterol, isoetharine, metaproterenol, pibuterol (MAXAIR®), salbutamol, salbutamol terbutaline, and salmeterol, terbutlaine (BRETHAIRE®)), corticosteroids (e.g., prednisone, beclomethasone dipropionate (VANCERIL® or BECLOVENT®), triamcinolone acetonide (AZMACORF®), flunisolide (AEROBID®), and fluticasone propionate (FLOVENT®)), leukotriene antagonists (e.g., montelukast, zafirlukast, and zileuton), theophylline (THEO-DUR®, UNIDUR® tablets, and SLO-BID® Gyrocaps), and salmeterol (SEREVENT®), cromolyn, and nedochromil (INTAL® and TILADE®)), IgE antagonists, IL-4 antagonists (including antibodies), IL-5 antagonists (including antibodies), PDE4 inhibitors, NF-Kappa-B inhibitors, IL-13 antagonists (including antibodies), CpG, CD23 antagonists, selectin antagonist (e.g., TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine), C2a receptor antagonists (including antibodies), and supportive respiratory therapy, such as supplemental and mechanical ventilation.

In some aspects, a subject has received at least one therapeutically effective dose of oral or inhaled corticosteroids. In certain aspects the subject has received a long-acting beta2-adrenergic agonist, e.g., salmeterol xinafoate. In some aspects the subject has received a synthetic glucocorticoid, e.g., fluticasone propionate. In certain aspects the subject has received a combination of salmeterol xinafoate and fluticasone propionate (ADVAIR®). In certain aspects the subject has received a beta2-adrenergic bronchodilator, e.g., albuterol sulfate. In other aspects, a subject has received at least one therapeutically effective dose of an antibody (e.g., an anti-IL-13 antibody, e.g., tralokinumab (SEQ ID NOs 8-9)) capable of neutralizing IL-13-mediated pathology. Other anti-IL-13 monoclonal antibodies that can be used include those described in U.S. Pat. Appl. Publ. No. 2012-0052060, published Mar. 1, 2012. Other IL-13 antagonists include, without limitation: (a) an anti-human-IL-13 antibody, for example, Lebrikizumab (SEQ ID NOs 6-7) (MILR1444A/RG3637, Roche/Genentech), ABT-308 (Abbott), GSK679586 (GlaxoSmithKline) or QAX576 (Novartis); (b) an anti-human-IL-13Rα1 antibody, for example, Merck MK6105; (c) an IL-13-toxin conjugate such as IL-13-PE38QQR (NeoPharm, Inc.); (d) an IL-4 mutein Aerovant™ (Aerovance, Inc.); (e) an anti-IL-4Rα antibody such as dupilumab/REGN668 (Regeneron); (f) a double-stranded oligonucleotide directed against IL-4Rα such as AIR645 (Isis); or (g) an IL-4 /IL-13 bispecific antibody such as GSK2434735 (Glaxo SmithKline).

In one aspect, the therapeutic agent used according to methods disclosed herein is an antibody, e.g., an anti-IL-13 antibody.

As used herein, the term "IL-13 antagonist" refers to any agent, which can affect the expression, activity, or half-life of IL-13 either in vitro or in vivo, or symptoms, pathology, or sequelae caused by or exacerbated by IL-13 in a subject with an IL-13-mediated disease or disorder. An IL-13 antagonist can be any "therapeutic agent" as defined below, which either directly or indirectly can inhibit, lessen, or neutralize IL-13 activity, inhibit or reduce IL-13 expression, reduce IL-13 half-life, or can prevent exacerbation of symptoms due to IL-13. In certain aspects, an IL-13 antagonist is an anti-IL-13 monoclonal antibody, e.g., tralokinumab (SEQ ID NOs 8-9), or other anti-IL-13 monoclonal antibodies described in U.S. Pat. Appl. Publ. No. 2012-0052060, published Mar. 1, 2012, herein incorporated by reference in its entirety.

The term "therapy" as used herein includes any means for curing, mitigating, or preventing an IL-13-mediated disease or disorder, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of an IL-13-mediated disease or disorder. In some aspects, the term "therapy" refers to administering a therapeutically effective amount of a therapeutic agent that is capable of reducing IL-13 activity or periostin levels in a patient in need thereof.

The term "therapeutic agent" as used herein refers to any therapeutically active substance that is administered to a subject having an IL-13-mediated disease or disorder to produce a desired, usually beneficial, effect. The term therapeutic agent includes, e.g., classical low molecular weight therapeutic agents commonly referred to as small molecule drugs and biologics including but not limited to: antibodies or active fragments thereof, peptides, lipids, protein drugs, protein conjugate drugs, enzymes, oligonucleotides, ribozymes, genetic material, prions, virus, bacteria, and eukaryotic cells. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated. A therapeutic agent can also be a radioactive isotope or agent activated by some other form of energy such as light or ultrasonic energy, or by other circulating molecules that can be systemically administered. In some aspects, the term "therapeutic agent" refers to therapeutically active substance that is capable of reducing IL-13 activity or periostin levels in a patient in need thereof.

A "therapeutically effective" amount as used herein is an amount of therapeutic agent that provides some improvement or benefit to a subject having an IL-13-mediated disease or disorder. Thus, a "therapeutically effective" amount is an amount that provides some alleviation, mitigation, and/or decrease in at least one clinical symptom of the pulmonary disease or disorder. Clinical symptoms associated with the pulmonary diseases and disorders that can be treated by the methods and systems of the disclosure are well known to those skilled in the art. In some embodiments, "therapeutically effective" amount is an amount that provides some alleviation, mitigation, and/or decrease in at least one clinical symptom of the chronic inflammatory skin disease or disorder. Clinical symptoms associated with the chronic inflammatory skin disease or disorder that can be treated by the methods and systems of the disclosure are well known to those skilled in the art. Further, those skilled in the art will appreciate that the therapeutic effects need not be complete or curative, as long as some benefit is provided to the subject. In some aspects, the term "therapeutically effective" refers to an amount of a therapeutic agent therapeutic agent that is capable of reducing IL-13 activity or periostin levels in a patient in need thereof.

As used herein, a "sufficient amount" or "an amount sufficient to" achieve a particular result in a patient having an IL-13-mediated disease or disorder refers to an amount of a therapeutic agent (e.g., an antibody) that is effective to produce a desired effect, which is optionally a therapeutic effect (i.e., by administration of a therapeutically effective amount). In some aspects, such particular result is a reduction in IL-13 activity or periostin levels in a patient in need thereof.

The term "sample" as used herein includes any biological fluid or issue, such as whole blood, serum, muscle, saliva obtained from a subject. Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, lung tissue, peripheral blood mononuclear cells, total white blood cells, lymph node cells, spleen cells, tonsil cells, or skin. In some specific aspects, that sample is blood or a fraction thereof, muscle, skin, or a combination thereof. Samples can be obtained by any means known in the art.

In order to apply the methods and systems of the disclosure, samples from a patient can be obtained before or after the administration of a therapy to treat an IL-13-mediated disease or disorder. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat an IL-13-mediated disease or disorder. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., a therapeutic agent that treats an IL-13-mediated disease or disorder such as asthma, IPF, COPD, or UC), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

"Vector" is used herein to describe a nucleic acid molecule that can transport another nucleic acid to which it has been linked. One type of vector is a "plasmid," which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Anti-Periostin Antibodies

This disclosure provides isolated anti-periostin antibodies and antigen-binding fragments thereof. In certain aspects, the anti-periostin antibodies and antigen-binding fragments provided herein can bind to human periostin. In certain aspects the antibodies and fragments provided herein bind to multiple isoforms of human periostin, e.g., at least isoforms 1, 2, 3, and 4. In some embodiments, the antibodies and fragments provided herein may bind at least one of isoforms 1, 2, 3, 4, 7, and 8. For example, the antibodies as detailed herein may bind at least one, at least two, at least three, at least four, at least five, or all six of isoforms 1, 2, 3, 4, 7, and 8. Isoforms 1, 2, 3, and 4 of human periostin are presented herein as SEQ ID NOs: 1 to 4, respectively, and their N-terminal regions are aligned in FIG. 1. Isoforms 7 and 8 of human periostin are presented herein as SEQ ID NOs 16 and 17. In some aspects, anti-periostin antibodies or fragments thereof provided herein can also bind to other isoforms of human periostin, and can also bind to periostin proteins from other species, e.g., mouse, rat, rabbit, and the like.

The disclosure provides, in particular, three novel murine monoclonal antibodies, which bind to the N-terminal region of human periostin. These antibodies were produced by standard hybridoma technology, and the hybridomas producing these antibodies have been deposited under the Budapest Treaty at the American Type Culture Collection, Manassas, Va. on Apr. 17, 2013. These anti-periostin antibodies are referred to herein as 4B4.B11, 7B5.C4, and 3C11.G5. Also provided are antigen-binding fragments, variants, and/or derivatives of these antibodies. Also provided are antibodies that are related to these antibodies in that they bind to the same epitope, or they are capable of competitively inhibiting one or more of 4B4.B11, 7B5.C4, and 3C11.G5. Monoclonal antibody 4B4.B11 is produced from a hybridoma deposited at the American Type Culture Collection, Manassas, Va. (the ATCC) under Deposit No. PTA-120210, monoclonal antibody 7B5.C4 is produced from a hybridoma deposited at the ATCC under Deposit No PTA-120211, and monoclonal antibody 3C11.G5 is produced from a hybridoma deposited at the ATCC under Deposit No. PTA-120209.

In certain aspects, an isolated antibody or antigen-binding fragment or derivative thereof is provided, wherein the antibody binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209.

In certain aspects, an isolated antibody or antigen-binding fragment or derivative thereof is provided, wherein the antibody competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209 to periostin, e.g., human periostin. For example, monoclonal antibodies 7B5.C4 and 3C11.G5 are capable of competitively inhibiting each other for binding to human periostin.

In certain aspects, an isolated anti-periostin antibody or fragment or derivative thereof is provided, wherein the antibody comprises a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209.

In certain aspects, an isolated anti-periostin antibody or fragment or derivative thereof is provided, wherein the antibody comprises a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209.

A person of ordinary skill in the art, upon obtaining one or more of the antibodies from one or more of the deposited hybridomas can isolate, clone, and sequence the expressed antibodies to determine the VH, VL, and CDR regions, without undue experimentation.

In certain aspects, an antibody-producing cell culture is provided, wherein the cell culture can be used to express an anti-periostin antibody or fragment or derivative thereof as provided herein. In certain aspects, the cell culture comprises a hybridoma selected from the group consisting of the hybridoma deposited at the ATCC under Deposit No. PTA-120210, the hybridoma deposited at the ATCC under Deposit No. PTA-120211, the hybridoma deposited at the ATCC under Deposit No. PTA-120209, and a combination thereof.

Any anti-periostin antibody or fragments, variants or derivatives thereof described herein can further include additional polypeptides, e.g., a signal peptide to direct secretion. Additionally, anti-periostin antibody or fragments, variants or derivatives thereof described herein can be, for example, fusion polypeptides, Fab fragments, scFvs, or other derivatives, as described herein.

In certain aspects, an anti-periostin antibody or fragment thereof as provided herein can be part of a fusion protein, that is, the antibody or antigen-binding fragment thereof can be fused to a heterologous polypeptide. The term "heterologous polypeptide" as used herein means that the polypeptide is derived from a distinct entity from the anti-periostin antibody or fragment thereof. In a non-limiting example, a "heterologous polypeptide" to be fused to an antibody or an antigen-binding fragment, variant, or derivative thereof can be derived from a non-immunoglobulin polypeptide of the same species, or an immunoglobulin or non-immunoglobulin heterologous polypeptide. In some aspects, the heterologous polypeptide can be, for example, a stabilizing polypeptide, a tag, a label, or a combination thereof.

In certain aspects, an anti-periostin antibody or fragment, variant or derivative thereof described herein can comprise a heterologous amino acid sequence or one or more other moieties not normally associated with an antibody (e.g., a peptide, a protein, an enzyme, a lipid, a heterologous antibody or fragment thereof, a detectable label, polyethylene glycol (PEG), or a combination of two or more of any said agents). In further aspects, an anti-periostin antibody or fragment, variant or derivative thereof described herein can comprise a detectable label selected from the group consisting of an enzyme, a fluorescent label, a chemiluminescent label, a bioluminescent label, a radioactive label, or a combination of two or more of any said detectable labels. In certain aspects, the detectable label is biotin, which can interact with streptavidin conjugated, e.g., to an enzyme, e.g., horseradish peroxidase (HRP). In certain aspects, the detectable label is a ruthenium chelate, which can emit light upon exposure to electrical current. Other detectable labels are well-known to those of ordinary skill in the art.

Also provided herein is a composition comprising one or more of the anti-periostin antibodies or fragments thereof as noted above. In certain aspects, a composition includes a "capture" antibody and a "detection" antibody, as described elsewhere herein. Compositions as provided herein can include without limitation buffers, carriers, and preservatives. Preservatives, stabilizers, buffers, antioxidants and/or other additives can include buffers such as phosphate, citrate, and other organic acids; antioxidants, such as ascorbic acid and methionine; preservatives such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol; low molecular weight polypeptides; proteins, such as serum albumin, gelatin, or immunoglobulins; hydrophilic polymers, such as polyvinylpyrrolidone; amino acids, such as glycine, glutamine, asparagines, histidine, arginine, or lysine; monosaccharides, disaccharides, and other carbohydrates including glucose, mannose, or dextrins; chelating agents, such as EDTA; sugars, such as sucrose, mannitol, trehalose, or sorbitol; salt-forming counter-ions, such as sodium; metal complexes (e.g., Zn-protein complexes); and/or non-ionic surfactants, such as TWEEN™, PLURONIC™, or polyethylene glycol (PEG). Compositions as provided herein can be mixed in a single vial or receptacle, or can be provided in two or more vials or receptacles, or as part of a kit, as described elsewhere herein.

Also provided herein is an isolated nucleic acid encoding an anti-periostin antibody, a fragment thereof, or a variant thereof. In some embodiments, the anti-periostin antibody, a fragment thereof, or a variant thereof, encoded by the isolated nucleic acid binds to isoforms 1, 2, 3, 4, 7, and 8 of human periostin. The isolated nucleic acid may comprise a nucleotide sequence that hybridizes, under stringent conditions, to the nucleic acid molecule that encodes an anti-periostin antibody, a fragment thereof, or a variant thereof. Also provided herein is a vector that comprises the isolated nucleic acid encoding an anti-periostin antibody, a fragment thereof, or a variant thereof.

Antibodies of the present disclosure can be prepared by delivering a nucleic acid or vector encoding an antibody of this disclosure to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489. Antibodies also can be prepared by delivering a nucleic acid or vector encoding an antibody of this disclosure to provide transgenic plants and cultured plant cells (for example, but not limited to, tobacco, maize, and duckweed) that produce such antibodies in the plant parts or in cells cultured therefrom.

In some embodiments, the anti-periostin antibodies or fragments thereof disclosed herein are produced in a host cell. In some embodiments, a host cell comprises a vector. The host cell may be prokaryotic. In some embodiments, the prokaryotic cell is an Escherichia coli cell. The host cell may be eukaryotic. In some embodiments, the eukaryotic cell is a CHO cell, a COS cell, a NSO cell, or a yeast cell. In some embodiments, the eukaryotic cell is a protist cell, animal cell, plant cell, or fungal cell. In some embodiments, the animal cell is a mammalian cell, an avian cell, or an insect cell. When vectors comprising nucleic acids encoding antibodies are introduced into host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Assays for Detecting Periostin Levels

This disclosure provides a method of measuring periostin levels in a sample obtained from a subject comprising assaying the sample in an immunoassay employing one or more anti-periostin antibodies or antigen binding fragments thereof, which recognize at least isoforms 1, 2, 3, and 4 of human periostin. In other aspects, the one or more anti-periostin antibodies or antigen binding fragments thereof, recognize at least isoforms 1, 2, 3, 4, 7, and 8 of human periostin. Exemplary antibodies for use in this method include one or more of murine monoclonal antibodies 4B4.B11, 7B5.C4, and 3C11.G5, or antigen-binding fragments or derivatives thereof, as described herein.

While not wishing to be bound by theory, an elevated periostin level in patients with asthma, IPF, COPD, and UC, as well as other inflammatory diseases that can be caused by, exacerbated by, or complicated by IL-13 expression, can be used to identify those patients who can benefit from therapies to reduce or neutralize IL-13 activity. See, e.g., Jia, et al., J Allergy Clin. Immunol 2012 130:647-654; Takayama, et al., J Allergy Clin Immunol 2006 118:98-104; and PCT Publ. No. WO 2012/083132.

The methods disclosed herein provide a much-needed assay for distinguishing between normal and elevated periostin levels and to thereby determine, for example, whether a patient having, or is suspected of having, an IL-13-mediated disease or disorder, such as certain subsets of asthma, COPD, IPF, or UC patients, would benefit from therapy. Moreover, the assays provided herein can distinguish between normal and elevated periostin levels at a level that is not provided by current commercially available periostin testing assays. See, e.g., FIGS. 7C and 7D.

The method involves the use of one or more highly specific and sensitive immunoassays for the detection of periostin in samples obtained from a subject. The samples are assayed in an immunoassay employing one or more anti-periostin antibodies provided herein, e.g., murine monoclonal antibodies 4B4.B11, 7B5.C4, and 3C11.G5, as described herein, or related antibodies, or antigen-binding fragments or derivatives thereof.

For example, the disclosure provides a method of measuring periostin levels in a sample obtained from a subject using an immunoassay provided herein, wherein each of the one or more anti-periostin antibodies is, independently, an isolated antibody or antigen-binding fragment or derivative thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209. In another aspect, each of the one or more anti-periostin antibodies is, independently, an isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209 to periostin. In another aspect, each of the one or more anti-periostin antibodies is, independently, an isolated antibody or antigen-binding fragment or derivative thereof comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209. In another aspect, each of the one or more anti-periostin antibodies is, independently, an isolated antibody or antigen-binding fragment or derivative thereof comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at ATCC under Deposit No. PTA-120209. Any of these antibodies or fragments thereof can be fused to one or more heterologous polypeptides, e.g., a stabilizing polypeptide, a tag, a label, or a combination thereof, or can be conjugated to a heterologous moiety, e.g., a peptide, a protein, an enzyme, a lipid, a heterologous antibody or fragment thereof, a detectable label, polyethylene glycol (PEG), or a combination of two or more of any the agents. In certain aspects, the antibody comprises a detectable label such as biotin or a ruthenium chelate. Other detectable labels are well known to those of ordinary skill in the art and are included in this disclosure.

The disclosure further provides a method for determining periostin levels in a test sample. The method provided herein can include (a) contacting the test sample with at least one capture antibody, wherein the capture antibody binds to an epitope on periostin or a fragment of periostin to form a capture antibody-periostin antigen complex; (b) contacting the capture antibody-periostin antigen complex with at least one detection antibody comprising a detectable label, wherein the detection antibody binds to an epitope on periostin that is not bound by the capture antibody and forms a capture antibody-periostin antigen-detection antibody complex; and (c) determining the periostin concentration in the test sample based on the signal generated by the detectable label in the capture antibody-periostin antigen-detection antibody complex formed in (b). The at least one capture antibody comprises the isolated antibody or antibody fragment as described above and the at least one detection antibody comprises the isolated antibody or fragment antibody as described above, and wherein the least one capture antibody is different from the at least one detection antibody.

In certain aspects, the immunoassay comprises a sandwich immunoassay, e.g., an enzyme-linked immunosorbent assay (ELISA) or a sandwich electrochemiluminescent (ECL) assay, in which a first anti-periostin "capture" antibody or antigen-binding fragment thereof is attached to a solid support, antigen from a sample or standard is allowed to bind to the capture antibody, and then a second anti-periostin "detection" antibody or antigen binding fragment thereof is added, and detected either by an enzymatic reaction, an electrochemiluminescent reaction, radioactivity, or other detection method. Sandwich assays may include, for example, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.). A chemiluminescent microparticle immunoassay, in particular one employing the ARCHITECT® automated analyzer (Abbott Laboratories, Abbott Park, Ill.), is an example of a preferred immunoassay. Other methods include, for example, mass spectrometry and immunohistochemistry (e.g., with sections from tissue biopsies) using anti-periostin antibodies as detailed herein.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and processed quickly through washes and detection steps to generate a measurable signal, such as a colored spot.

In certain aspects, the immunoassay comprises the following: first, the capture antibody or fragment thereof is allowed to bind to a solid support, e.g., a multi-well plate or other assay device known to those of ordinary skill in the art. The capture antibody is allowed to attach for a period of time, e.g., overnight, and then unbound antibody is removed. The plate can then be washed to remove any unbound capture antibody. The plate can then be treated with a blocking solution to allow non-specific protein to bind to any unbound regions of the solid support. Typical blocking solutions include an unrelated protein, e.g., nonfat dry milk or serum albumin. The plate can then again be washed to remove any unbound blocking solution. Next, a sample suspected of containing periostin is added to the plate. Samples are typically serially diluted and plated in duplicate or triplicate. Controls, including standard amounts of periostin or a suitable fragment thereof and various negative controls are also included. The antigen is allowed to bind to the capture antibody for a period of time, e.g., one hour at room temperature. Following incubation, the plate can then be washed to remove any unbound antigen.

Next, a detection antibody is added. The detection antibody is typically an anti-periostin antibody that binds to a different periostin epitope than the capture antibody. The detection antibody can be labeled or unlabeled. Where the detection antibody is unlabeled, an addition step of addition a labeled secondary antibody will be required, as is well known by those of ordinary skill in the art. Where the detection antibody is labeled, any detectable label known in the art can be used. The detection antibody can be directly labeled with an enzyme, e.g., horseradish peroxidase or alkaline phosphatase, or can be labeled with a tag that will allow an enzyme to bind. For example the detection antibody can be conjugated to biotin, and the enzyme attached in a subsequent step by allowing enzyme-conjugated streptavidin to bind to the biotin tag. Alternatively the detection antibody can be conjugated to a chemiluminescent, fluorescent, or electrochemiluminescent tag. An example of the latter is a ruthenium chelate. Following incubation, the plate can then be washed to remove any unbound detection antibody. Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed. The order in which the test sample and the specific binding partner(s) are added to form the mixture for chemiluminescent assay is not critical.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art. Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Detection of the detection antibody is accomplished by methods that will vary based on the type of detection antibody that is used. If the detection antibody is tagged with biotin, then enzyme-conjugated streptavidin is added, unbound streptavidin is washed away, and a substrate is added which provides a colorimetric reaction that can be read, e.g., on a spectrophotometer. If the detection antibody is conjugated to a ruthenium chelate, the plate is subjected to electrical current, and light emission is measured.

For chemiluminescent assays, a detectable signal, namely, a chemiluminescent signal, indicative of the presence of periostin is generated upon the simultaneous or subsequent addition of at least one basic solution to the sample. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. The chemiluminescent signal that is generated can be detected using routine techniques known to those skilled in the art. Based on the intensity of the signal generated, the amount of periostin in the sample can be quantified. Specifically, the amount of periostin in the sample is proportional to the intensity of the signal generated. The amount of periostin present can be quantified by comparing the amount of light generated to a standard curve for periostin or by comparison to a reference standard. The standard curve can be generated using serial dilutions or solutions of known concentrations of periostin by mass spectroscopy, gravimetric methods, and other techniques known in the art. In a chemiluminescent microparticle assay employing the ARCHITECT® (or its successor) analyzer, the conjugate diluent pH should be about 6.0+/−0.2, the microparticle coating buffer should be maintained at room temperature (i.e., at about 17° C. to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

In certain aspects, the method directly measures periostin levels in a patient sample, where absolute levels are calculated by plotting the immunoassay results on a standard curve using, e.g., purified full length or N-terminal periostin. The detected signal from the detection antibody can then be quantitated based on the various standards and controls included on the plate. By plotting the results on a standard curve, the absolute levels of periostin in the test samples can be calculated, e.g., in ng/mL or pg periostin/mg protein.

Based on comparison to known control samples, a threshold periostin level can be determined, and test samples that fall above that threshold can indicate that the patient from whom the sample was taken may benefit from treatment with an IL-13 antagonist. Threshold levels must be predetermined, and must be matched as to the type of sample (e.g., serum or lung tissue), the type of disease (e.g., asthma, IPF, COPD, or UC), and in some instances, the assay used. In some embodiments, the type of disease is atopic dermatitis. For example, a threshold level of serum periostin in a patient sample from an asthma patient, above which the patient might benefit from IL-13 antagonist treatment can be at least about 15 ng periostin/mL serum to about 150 ng periostin/mL serum, e.g., about 15 ng periostin/mL serum, about 20 ng periostin/mL serum, about 25 ng periostin/mL serum, about 30 ng periostin/mL serum, about 35 ng periostin/mL serum, about 40 ng periostin/mL serum, about 45 ng periostin/mL serum, about 50 ng periostin/mL serum, about 55 ng periostin/mL serum, about 60 ng periostin/mL serum, about 65 ng periostin/mL serum, about 70 ng periostin/mL serum, about 75 ng periostin/mL serum, about 80 ng periostin/mL serum, about 85 ng periostin/mL serum, about 90 ng periostin/mL serum, about 95 ng periostin/mL serum, about 100 ng periostin/mL serum, about 105 ng periostin/mL serum, about 110 ng periostin/mL serum, about 115 ng periostin/mL serum, about 120 ng periostin/mL serum, about 125 ng periostin/mL serum, about 130 ng periostin/mL serum, about 135 ng periostin/mL serum, about 140 ng periostin/mL serum, about 145 ng periostin/mL serum, or about 150 ng periostin/mL serum. In some aspects, the predetermined periostin level in a patient sample from an asthma patient, above which the patient might benefit from IL-13 antagonist treatment can be a serum periostin mean or median level as depicted in FIGS. 5B, 6, 9, 10A or 10B. In some aspects, the predetermined periostin level in a patient sample from an asthma patient, above which the patient might benefit from IL-13 antagonist treatment can be at least about 15 ng periostin/mL serum to about 25 ng periostin/mL serum, e.g., at least about 15 ng periostin/mL serum, at least about 20 ng periostin/mL serum, or at least about 25 ng periostin/mL serum. A threshold level of serum periostin in a patient sample from an asthma patient, above which the patient might benefit from IL-13 antagonist treatment can be at least about 5 ng periostin/mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. A threshold level of serum periostin in a patient sample from an asthma patient, above which the patient might benefit from IL-13 antagonist treatment can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. A threshold level of serum periostin in a patient sample from an asthma patient, above which the patient might benefit from IL-13 antagonist treatment can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum. In another example, a threshold level of serum periostin in a patient sample from an IPF patient, above which the patient might benefit from IL-13 antagonist treatment can be at least about 15 ng periostin/mL serum to about 150 ng periostin/mL serum, e.g., about 15 ng periostin/mL serum, about 20 ng periostin/mL serum, about 25 ng periostin/mL serum, about 30 ng periostin/mL serum, about 35 ng periostin/mL serum, about 40 ng periostin/mL serum, about 45 ng periostin/mL serum, about 50 ng periostin/mL serum, about 55 ng periostin/mL serum, about 60 ng periostin/mL serum, about 65 ng periostin/mL serum, about 70 ng periostin/mL serum, about 75 ng periostin/mL serum, about 80 ng periostin/mL serum, about 85 ng periostin/mL serum, about 90 ng periostin/mL serum, about 95 ng periostin/mL serum, about 100 ng periostin/mL serum, about 105 ng periostin/mL serum, about 110 ng periostin/mL serum, about 115 ng periostin/mL serum, about 120 ng periostin/mL serum, about 125 ng periostin/mL serum, about 130 ng periostin/mL serum, about 135 ng periostin/mL serum, about 140 ng periostin/mL serum, about 145 ng periostin/mL serum, or about 150 ng periostin/mL serum. In some aspects, the predetermined periostin level in a patient sample from an IPF patient, above which the patient might benefit from IL-13 antagonist treatment can be a serum periostin mean level as depicted in FIG. 7 or 9. In some aspects, the predetermined periostin level in a patient sample from an IPF patient, above which the patient might benefit from IL-13 antagonist treatment can be at least about 40 ng periostin/mL serum to about 60 ng periostin/mL serum, e.g., at least about 40 ng periostin/mL serum, at least about 50 ng periostin/mL serum, or at least about 60 ng periostin/mL serum. A threshold level of serum periostin in a patient sample from an IPF patient, above which the patient might benefit from IL-13 antagonist treatment can be at least about 5 ng periostin/mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. A threshold level of serum periostin in a patient sample from an IPF patient, above which the patient might benefit from IL-13 antagonist treatment can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. A threshold level of serum periostin in a patient sample from an IPF patient, above which the patient might benefit from IL-13 antagonist treatment can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum. In another example, a threshold level of serum periostin in a patient sample from an atopic dermatitis patient, above which the patient might benefit from IL-13 antagonist treatment can be at least about 5 ng periostin/mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. A threshold level of serum periostin in a patient sample from an atopic dermatitis patient, above which the patient might benefit from IL-13 antagonist treatment can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. A threshold level of serum periostin in a patient sample from an IPF patient, above which the patient might benefit from IL-13 antagonist treatment can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum.

In some aspects, the predetermined periostin level in a patient sample above which the patient might benefit from IL-13 antagonist treatment is at least about 16.44 ng periostin/mL serum. In some aspects, the predetermined periostin level in a patient sample from an asthma patient above which the patient might benefit from IL-13 antagonist treatment is at least about 16.44 ng periostin/mL serum.

In another example, a threshold level of periostin in a lung tissue extract from a IPF patient, above which the patient might benefit from IL-13 antagonist treatment can be at least about 2 pg periostin/mg total protein to about 25 pg periostin/mg total protein, e.g., about 2 pg periostin/mg total protein, about 3 pg periostin/mg total protein, about 4 pg periostin/mg total protein, about 5 pg periostin/mg total protein, about 6 pg periostin/mg total protein, about 7 pg periostin/mg total protein, about 8 pg periostin/mg total protein, about 9 pg periostin/mg total protein, about 10 pg periostin/mg total protein, about 11 pg periostin/mg total protein, about 12 pg periostin/mg total protein, about 13 pg periostin/mg total protein, about 14 pg periostin/mg total protein, about 15 pg periostin/mg total protein, about 18 pg periostin/mg total protein, about 20 pg periostin/mg total protein, about 22 pg periostin/mg total protein, about 24 pg periostin/mg total protein, or about 25 pg periostin/mg total protein. In some aspects, the predetermined periostin level in a lung tissue extract from an IPF patient, above which the patient might benefit from IL-13 antagonist treatment can be a periostin mean level as depicted in FIG. 8. In some aspects, the predetermined periostin level in a lung tissue extract from an IPF patient, above which the patient might benefit from IL-13 antagonist treatment can be at least about at least about 15 pg periostin/mg total protein to about 25 pg periostin/mg total protein, e.g., at least about 15 pg periostin/mg total protein, at least about 20 pg periostin/mg total protein, or at least about 25 pg periostin/mg total protein. A threshold level of periostin in a lung tissue extract from a IPF patient, above which the patient might benefit from IL-13 antagonist treatment can be at least about 5 pg periostin/mg total protein, at least about 10 pg periostin/mg total protein, at least about 15 pg periostin/mg total protein, at least about 16.44 pg periostin/mg total protein, at least about 20 pg periostin/mg total protein, at least about 25 pg periostin/mg total protein, at least about 30 pg periostin/mg total protein, at least about 35 pg periostin/mg total protein, at least about 40 pg periostin/mg total protein, at least about 45 pg periostin/mg total protein, at least about 50 pg periostin/mg total protein, at least about 55 pg periostin/mg total protein, at least about 60 pg periostin/mg total protein, at least about 65 pg periostin/mg total protein, at least about 70 pg periostin/mg total protein, at least about 75 pg periostin/mg total protein, at least about 80 pg periostin/mg total protein, at least about 85 pg periostin/mg total protein, at least about 90 pg periostin/mg total protein, at least about 95 pg periostin/mg total protein, at least about 100 pg periostin/mg total protein, at least about 105 pg periostin/mg total protein, at least about 110 pg periostin/mg total protein, at least about 115 pg periostin/mg total protein, at least about 120 pg periostin/mg total protein, at least about 125 pg periostin/mg total protein, at least about 130 pg periostin/mg total protein, at least about 135 pg periostin/mg total protein, at least about 140 pg periostin/mg total protein, at least about 145 pg periostin/mg total protein, or at least about 150 pg periostin/mg total protein. A threshold level of periostin in a lung tissue extract from a IPF patient, above which the patient might benefit from IL-13 antagonist treatment can be less than about 150 pg periostin/mg total protein, less than about 145 pg periostin/mg total protein, less than about 140 pg periostin/mg total protein, less than about 135 pg periostin/mg total protein, less than about 130 pg periostin/mg total protein, less than about 125 pg periostin/mg total protein, less than about 120 pg periostin/mg total protein, less than about 115 pg periostin/mg total protein, less than about 110 pg periostin/mg total protein, less than about 105 pg periostin/mg total protein, less than about 100 pg periostin/mg total protein, less than about 95 pg periostin/mg total protein, less than about 90 pg periostin/mg total protein, less than about 85 pg periostin/mg total protein, less than about 80 pg periostin/mg total protein, less than about 75 pg periostin/mg total protein, less than about 70 pg periostin/mg total protein, less than about 65 pg periostin/mg total protein, less than about 60 pg periostin/mg total protein, less than about 55 pg periostin/mg total protein, less than about 50 pg periostin/mg total protein, less than about 45 pg periostin/mg total protein, less than about 40 pg periostin/mg total protein, less than about 35 pg periostin/mg total protein, less than about 30 pg periostin/mg total protein, less than about 25 pg periostin/mg total protein, less than about 20 pg periostin/mg total protein, less than about 16.44 pg periostin/mg total protein, less than about 15 pg periostin/mg total protein, less than about 10 pg periostin/mg total protein, or less than about 5 pg periostin/mg total protein. A threshold level of periostin in a lung tissue extract from a IPF patient, above which the patient might benefit from IL-13 antagonist treatment can be about 4.5 to about 150 pg periostin/mg total protein, about 4.5 to about 125 pg periostin/mg total protein, about 4.5 to about 100 pg periostin/mg total protein, about 4.5 to about 75 pg periostin/mg total protein, about 4.5 to about 50 pg periostin/mg total protein, about 4.5 to about 25 pg periostin/mg total protein, about 5 to about 150 pg periostin/mg total protein, about 5 to about 125 pg periostin/mg total protein, about 5 to about 100 pg periostin/mg total protein, about 5.2 to about 73.3 pg periostin/mg total protein, about 5 to about 75 pg periostin/mg total protein, about 5 to about 50 pg periostin/mg total protein, about 5 to about 25 pg periostin/mg total protein, about 25 to about 150 pg periostin/mg total protein, about 25 to about 125 pg periostin/mg total protein, about 25 to about 100 pg periostin/mg total protein, about 25 to about 75 pg periostin/mg total protein, about 25 to about 50 pg periostin/mg total protein, about 50 to about 150 pg periostin/mg total protein, about 50 to about 125 pg periostin/mg total protein, about 50 to about 100 pg periostin/mg total protein, about 50 to about 75 pg periostin/mg total protein, about 100 to about 150 pg periostin/mg total protein, about 100 to about 125 pg periostin/mg total protein, or about 125 to about 150 pg periostin/mg total protein.

In another example, a threshold level of serum periostin in a patient sample from an UC patient, above which the patient might benefit from IL-13 antagonist treatment can be at least about 15 ng periostin/mL serum to about 150 ng periostin/mL serum, e.g., about 15 ng periostin/mL serum, about 20 ng periostin/mL serum, about 25 ng periostin/mL serum, about 30 ng periostin/mL serum, about 35 ng periostin/mL serum, about 40 ng periostin/mL serum, about 45 ng periostin/mL serum, about 50 ng periostin/mL serum, about 55 ng periostin/mL serum, about 60 ng periostin/mL serum, about 65 ng periostin/mL serum, about 70 ng periostin/mL serum, about 75 ng periostin/mL serum, about 80 ng periostin/mL serum, about 85 ng periostin/mL serum, about 90 ng periostin/mL serum, about 95 ng periostin/mL serum, about 100 ng periostin/mL serum, about 105 ng periostin/mL serum, about 110 ng periostin/mL serum, about 115 ng periostin/mL serum, about 120 ng periostin/mL serum, about 125 ng periostin/mL serum, about 130 ng periostin/mL serum, about 135 ng periostin/mL serum, about 140 ng periostin/mL serum, about 145 ng periostin/mL serum, or about 150 ng periostin/mL serum. In some aspects, the predetermined periostin level in a patient sample from an UC patient, above which the patient might benefit from IL-13 antagonist treatment can be a serum periostin mean level as depicted in FIG. 9. In some aspects, the predetermined periostin level in a patient sample from an UC patient, above which the patient might benefit from IL-13 antagonist treatment can be at least about 20 ng periostin/mL serum to about 40 ng periostin/mL serum, e.g., at least about 20 ng periostin/mL serum, at least about 30 ng periostin/mL serum, or at least about 40 ng periostin/mL serum. A threshold level of serum periostin in a patient sample from an UC patient, above which the patient might benefit from IL-13 antagonist treatment can be at least about 5 ng periostin/mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. A threshold level of serum periostin in a patient sample from an UC patient, above which the patient might benefit from IL-13 antagonist treatment can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. A threshold level of serum periostin in a patient sample from an UC patient, above which the patient might benefit from IL-13 antagonist treatment can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum.

The threshold level can vary based on the nature of the assay, e.g., the capture and detection antibodies used, the source, purity, and composition of the periostin standard, and the like.

In one aspect, instead of using an arbitrary threshold level to determine whether a patient can benefit from treatment with an IL-13 antagonist, the patient's periostin levels can be compared to one or more control periostin levels. According to this aspect, the test (e.g., patient) sample is compared to one or more control samples, e.g., to samples taken from normal healthy individuals, to earlier samples taken from the same patient, to samples taken from patients with a non-IL-13-mediated subset of the patient's disease, e.g., asthma, COPD, IPF, or UC, or to a pre-determined standard amount of isolated periostin, or a combination thereof. In some embodiments, the patient's disease is atopic dermatitis. The results can be expressed as a ratio with the control samples to determine a percent increase or a percent decrease in the patient's periostin levels compared to the control periostin levels. According to this aspect, the control sample can be a matched pair with the patient sample, e.g., one or more of whole blood if the patient sample is whole blood, serum if the patient sample is serum, plasma if the patient sample is plasma, saliva if the patient sample is saliva, sputum if the patient sample is sputum, bronchoalveolar lavage fluid if the patient sample is bronchoalveolar lavage fluid, or lung tissue if the patient sample is lung tissue.

In some aspects, patients who would likely benefit from IL-13 antagonist treatment can be selected by identifying those having periostin levels above the mean and/or median level of periostin in a population of patients (e.g., asthma, IPF, COPD, UC patients); with the use of the mean and/or median value for all patients defining the cutoff point between a high-periostin subgroup (mean and/or median value or higher) and a low-periostin subgroup (less than the mean and/or median value). In some embodiments, the population of patients include atopic dermatitis patients. See Corren et al. N Engl J Med. 365(12):1088-98 (2011), herein incorporated by reference in its entirety for all purposes. According to this aspect, those patients falling within the high-periostin subgroup would likely benefit from treatment with an IL-13 antagonist.

In certain aspects of the immunoassay and method provided herein the capture antibody is 3C11.G5 or 7B5.C4. In certain aspects of the immunoassay and method provided herein the detection antibody is 4B4.B11 or 7B5.C4. In certain aspects of the immunoassay and method provided herein the capture antibody is 7B5.C4 and the detection antibody is 4B4.B11.

A variety of subject samples, taken from either a patient or a healthy control, can be used in the methods presented herein. Exemplary, non-limiting examples of samples include one or more of whole blood, serum, plasma, saliva, sputum, nasal polyps, nasal mucus, bronchoalveolar lavage fluid, or lung tissue, e.g., lung epithelial cells. The choice of sample can depend on, e.g., the type of disease, the severity of the disease, the availability of suitable controls, or patient compliance. In specific aspects, the sample is a serum sample or lung tissue.

Methods of Treatment

This disclosure provides a method of treating a patient having an IL-13-mediated disease or disorder, or a patient with a pulmonary or inflammatory bowel disease or disorder of unknown etiology which might be IL-13-mediated, comprising administering an IL-13 antagonist to the patient if the periostin level in a sample taken from the patient is above a predetermined threshold level, or is elevated relative to the periostin level in one or more control samples. In one aspect, the patient's periostin level is measured in an immunoassay employing one or more anti-periostin antibodies or antigen binding fragments thereof which recognize at least isoforms 1, 2, 3, and 4 of human periostin, e.g., murine monoclonal antibodies 4B4.B11, 7B5.C4, and 3C11.G5, as described herein, or antigen-binding fragments, variants or derivatives thereof, or related antibodies or antigen-binding fragments thereof, also as described herein. In one aspect, the patient's periostin level is measured in an immunoassay employing one or more anti-periostin antibodies or antigen binding fragments thereof which recognize at least isoforms 1, 2, 3, 4, 7, and 8 of human periostin, e.g., murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

This disclosure provides methods, assays, and kits to facilitate a determination by a healthcare provider, a healthcare benefits provider, or a clinical laboratory to as to whether a patient will benefit from treatment with an IL-13 antagonist, e.g., an ant-IL-13 antibody or antigen-binding fragment thereof, e.g., tralokinumab (SEQ ID NOs 8-9), or a fragment, variant, or derivative thereof, an antibody or fragment thereof that binds to the same IL-13 epitope as tralokinumab, or an antibody or fragment thereof that competitively inhibits binding of tralokinumab to IL-13. The methods assays and kits provided herein will also facilitate a determination by a healthcare provider, a healthcare benefits provider, or a clinical laboratory to as to whether a patient will benefit from treatment with any other IL-13 antagonist IL-13 disclosed herein, or known to those of ordinary skill in the art.

In one aspect, this disclosure provides a method of treating a patient having an IL-13-mediated disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, and 4 of human periostin. In another aspect, this disclosure provides a method of treating a patient having an IL-13-mediated disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, 4, 7, and 8 of human periostin. According to this method immunoassays provided herein or variations known to those of ordinary skill in the art can utilized to determine treatment for the patient. In certain aspects, the one or more anti-periostin antibodies are one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, the immunoassay is performed on a sample obtained from the patient, by the healthcare professional treating the patient, e.g., using an immunoassay as described herein, formulated as a "point of care" diagnostic kit. In some aspects, a sample is obtained from the patient and is submitted, e.g., to a clinical laboratory, for measurement of the periostin level in the sample according to the healthcare professional's instructions, e.g., using an immunoassay as described herein. In certain aspects, the clinical laboratory performing the assay will advise the healthcare provide as to whether the patient can benefit from treatment with an IL-13 antagonist based on whether the patient's periostin level is above a predetermined threshold value or is elevated relative to one or more control samples.

In certain aspects, this disclosure provides a method of treating a patient having an IL-13-mediated disease or disorder over a period of time, comprising: measuring a first periostin level in a first sample taken from the patient, or submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, and 4 of human periostin, and administering an IL-13 antagonist to the patient if the patient's periostin level in the first sample is above a predetermined threshold level, or is elevated relative to the periostin level in one or more control samples. In other aspects, this disclosure provides a method of treating a patient having an IL-13-mediated disease or disorder over a period of time, comprising: measuring a first periostin level in a first sample taken from the patient, or submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, 4, 7, and 8 of human periostin, and administering an IL-13 antagonist to the patient if the patient's periostin level in the first sample is above a predetermined threshold level, or is elevated relative to the periostin level in one or more control samples. The test can be performed by a healthcare provider or a clinical laboratory as noted above. In certain aspects, the one or more anti-periostin antibodies are one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, the immunoassay is performed on a sample obtained from the patient by the healthcare professional treating the patient, e.g., using an immunoassay as described herein, formulated as a "point of care" diagnostic kit. In some aspects, a sample is obtained from the patient and is submitted, e.g., to a clinical laboratory, for measurement of the periostin level in the sample according to a healthcare professional's instructions, e.g., using an immunoassay as described herein. In certain aspects, the clinical laboratory performing the assay will advise the healthcare provide as to whether the patient can benefit from treatment with an IL-13 antagonist based on whether the patient's periostin level is above a predetermined threshold value or is elevated relative to one or more control samples.

According to this aspect, the method can further comprise: measuring a second periostin level in a second sample taken from the patient, or submitting a second sample taken from the patient for measurement of a second periostin level in the sample, wherein the patient's periostin level is again measured in an immunoassay employing one or more anti-periostin antibodies or antigen binding fragments thereof which recognize at least isoforms 1, 2, 3, and 4 of human periostin; comparing the first and second periostin levels in the patient, and altering the dose, e.g., increasing or maintaining the amount or frequency of the IL-13 antagonist administered to the patient, or even discontinuing IL-13 antagonist therapy if the patient's periostin level in the second sample is higher than the periostin level in the first sample, or maintaining or reducing the amount or frequency of the IL-13 antagonist administered to the patient if the patient's periostin level in the second sample is lower than or about the same as the periostin level in the first sample. In other aspects, the method can further comprise: measuring a second periostin level in a second sample taken from the patient, or submitting a second sample taken from the patient for measurement of a second periostin level in the sample, wherein the patient's periostin level is again measured in an immunoassay employing one or more anti-periostin antibodies or antigen binding fragments thereof which recognize at least isoforms 1, 2, 3, 4, 7, and 8 of human periostin; comparing the first and second periostin levels in the patient, and altering the dose, e.g., increasing or maintaining the amount or frequency of the IL-13 antagonist administered to the patient, or even discontinuing IL-13 antagonist therapy if the patient's periostin level in the second sample is higher than the periostin level in the first sample, or maintaining or reducing the amount or frequency of the IL-13 antagonist administered to the patient if the patient's periostin level in the second sample is lower than or about the same as the periostin level in the first sample.

In certain aspects of all the method of treatment aspects provided herein, a "loading" dose of an IL-13 antagonist is administered to achieve a desired therapeutic level in the patient. If the loading dose does not affect the patient's periostin levels significantly or the patient's periostin levels rise, a decision could be made to discontinue treatment—e.g., to use a non-IL-13 antagonist therapy. If the loading dose results in steady or reduced periostin levels in the patient a decision could be made to reduce the dose size or frequency to a "maintenance" dose. It is important to note that the methods provided here are guidelines for a healthcare provider to administer treatment, and the ultimate treatment decision will be based on the healthcare provider's sound judgment.

In certain aspects, results of an immunoassay as provided herein can be submitted to a healthcare benefits provider for determination of whether the patient's insurance will cover treatment with an IL-13 antagonist.

In certain aspects this disclosure provides a method of treating a patient having an IL-13-mediated disease or disorder comprising: measuring, e.g., in a clinical laboratory, the periostin level in a first sample obtained from a patient having an IL-13-mediated disease or disorder, e.g., a sample provided by a healthcare provider, wherein the patient's periostin level in the first sample is measured in an immunoassay employing one or more anti-periostin antibodies or antigen binding fragments thereof which recognize at least isoforms 1, 2, 3, and 4 of human periostin, determining whether the patient's periostin level in the first sample is above a predetermined threshold level, or is elevated relative to the periostin level in one or more control samples; and advising a healthcare provider to administer an IL-13 antagonist to the patient if the patient's periostin level is above a predetermined threshold level, or is elevated relative to the periostin level in one or more control samples. In other aspects, this disclosure provides a method of treating a patient having an IL-13-mediated disease or disorder comprising: measuring, e.g., in a clinical laboratory, the periostin level in a first sample obtained from a patient having an IL-13-mediated disease or disorder, e.g., a sample provided by a healthcare provider, wherein the patient's periostin level in the first sample is measured in an immunoassay employing one or more anti-periostin antibodies or antigen binding fragments thereof which recognize at least isoforms 1, 2, 3, 4, 7, and 8 of human periostin, determining whether the patient's periostin level in the first sample is above a predetermined threshold level, or is elevated relative to the periostin level in one or more control samples; and advising a healthcare provider to administer an IL-13 antagonist to the patient if the patient's periostin level is above a predetermined threshold level, or is elevated relative to the periostin level in one or more control samples. In certain aspects, the one or more anti-periostin antibodies are one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, this method can further comprise: measuring the periostin level in a second sample obtained from the patient, e.g., a sample provided by a healthcare provider, wherein the patient's periostin level is again measured in an immunoassay employing one or more anti-periostin antibodies or antigen binding fragments thereof which recognize at least isoforms 1, 2, 3, and 4 of human periostin; determining whether the patient's periostin level in the second sample is higher than, about the same as, or lower than the periostin level measured in the first sample; and advising a healthcare provider to adjust the IL-13 antagonist therapy if indicated, e.g., to increase or maintain the amount or frequency of the IL-13 antagonist administered to the patient, or discontinuing IL-13 antagonist therapy, if the patient's periostin level in the second sample is higher than the periostin level in the first sample, or to maintain or reduce the amount or frequency of the IL-13 antagonist administered to the patient if the patient's periostin level in the second sample is lower than or about the same as the periostin level in the first sample. In other aspects, the method can further comprise: measuring the periostin level in a second sample obtained from the patient, e.g., a sample provided by a healthcare provider, wherein the patient's periostin level is again measured in an immunoassay employing one or more anti-periostin antibodies or antigen binding fragments thereof which recognize at least isoforms 1, 2, 3, 4, 7, and 8 of human periostin; determining whether the patient's periostin level in the second sample is higher than, about the same as, or lower than the periostin level measured in the first sample; and advising a healthcare provider to adjust the IL-13 antagonist therapy if indicated, e.g., to increase or maintain the amount or frequency of the IL-13 antagonist administered to the patient, or discontinuing IL-13 antagonist therapy, if the patient's periostin level in the second sample is higher than the periostin level in the first sample, or to maintain or reduce the amount or frequency of the IL-13 antagonist administered to the patient if the patient's periostin level in the second sample is lower than or about the same as the periostin level in the first sample.

In some aspects, a sample is obtained from the patient and is submitted, e.g., to a clinical laboratory, for measurement of the periostin level in the sample, e.g., using an immunoassay as described herein. In certain aspects, the clinical laboratory performing the assay will advise the healthcare provide as to whether the patient can benefit from treatment with an IL-13 antagonist based on whether the patient's periostin level is above a predetermined threshold value or is elevated relative to one or more control samples.

Similarly, this disclosure provides a method of monitoring the therapeutic efficacy of an IL-13 antagonist therapeutic regimen in a patient having an IL-13-mediated disease or disorder comprising: measuring, or instructing a clinical laboratory to measure the periostin level in a first sample obtained from a patient having an IL-13-mediated disease or disorder, wherein the patient's periostin level is measured in an immunoassay employing one or more anti-periostin antibodies or antigen binding fragments thereof which recognize at least isoforms 1, 2, 3, and 4 of human periostin; administering, or advising a healthcare professional to administer an IL-13 antagonist to a patient if the patient's periostin level in the first sample is above a predetermined threshold level, or is elevated relative to the periostin level in one or more control samples; measuring the periostin level in a second sample obtained from the patient, wherein the patient's periostin level is again measured in an immunoassay employing one or more anti-periostin antibodies or antigen binding fragments thereof which recognize at least isoforms 1, 2, 3, and 4 of human periostin, and determining, or obtaining results indicating whether the patient's periostin level in the second sample is higher than, about the same as, or lower than the periostin level measured in the first sample; wherein the IL-13 antagonist therapeutic regimen is effective if the patient's periostin level in the second sample is lower than or about the same as the periostin level in the first sample. In other aspects, this disclosure provides a method of monitoring the therapeutic efficacy of an IL-13 antagonist therapeutic regimen in a patient having an IL-13-mediated disease or disorder comprising: measuring, or instructing a clinical laboratory to measure the periostin level in a first sample obtained from a patient having an IL-13-mediated disease or disorder, wherein the patient's periostin level is measured in an immunoassay employing one or more anti-periostin antibodies or antigen binding fragments thereof which recognize at least isoforms 1, 2, 3, 4, 7, and 8 of human periostin; administering, or advising a healthcare professional to administer an IL-13 antagonist to a patient if the patient's periostin level in the first sample is above a predetermined threshold level, or is elevated relative to the periostin level in one or more control samples; measuring the periostin level in a second sample obtained from the patient, wherein the patient's periostin level is again measured in an immunoassay employing one or more anti-periostin antibodies or antigen binding fragments thereof which recognize at least isoforms 1, 2, 3, 4, 7, and 8 of human periostin, and determining, or obtaining results indicating whether the patient's periostin level in the second sample is higher than, about the same as, or lower than the periostin level measured in the first sample; wherein the IL-13 antagonist therapeutic regimen is effective if the patient's periostin level in the second sample is lower than or about the same as the periostin level in the first sample.

In certain aspects, the immunoassay is performed on a sample obtained from the patient by the healthcare professional treating the patient, e.g., using an immunoassay as described herein, formulated as a "point of care" diagnostic kit. In some aspects, a sample is obtained from the patient and is submitted, e.g., to a clinical laboratory, for measurement of the periostin level in the sample, e.g., using an immunoassay as described herein. In certain aspects, the clinical laboratory performing the assay will advise the healthcare provide as to whether the patient can benefit from treatment with an IL-13 antagonist, or whether the IL-13 antagonist therapy appears to be effective, based on whether the patient's periostin level is above a predetermined threshold value or is elevated relative to one or more control samples.

In certain aspects described above, the patient having, or suspected of having, an IL-13-mediated disease or disorder has been diagnosed with a pulmonary disease or disorder or an inflammatory bowel disease or disorder which, in a subset of differential diagnoses, can be IL-13-mediated. In some embodiments, the patient has been diagnosed with a chronic inflammatory skin disease or disorder. The differential diagnosis can be facilitated, e.g., by measuring the patient's IgE levels, measuring the patient's eosinophil count, making a symptom analysis, determining the patient's Fraction of Exhaled Nitric Oxide (FENO), determining the patient's Eosinophil/Lymphocyte and Eosinophil/Neutrophil (ELEN) index, or a combination of two or more such measurements. See, e.g., U.S. Pat. Appl. Publication 2012-0328606, published Dec. 27, 2012, and incorporated herein by reference in its entirety. In certain aspects, the disease or disorder having or suspected of having IL-13-mediated pathology is asthma, idiopathic pulmonary fibrosis (IPF), chronic obstructive pulmonary disease (COPD), ulcerative colitis (UC), allergic rhinitis, or chronic rhinosinusitis. In some embodiments, the disease or disorder having or suspected of having IL-13-mediated pathology is atopic dermatitis.

In certain aspects, a patient is diagnosed with a pulmonary disease or disorder, and in the course of diagnosis a determination can be made as whether to treat the patient with an IL-13 antagonist. Accordingly, in certain aspects this disclosure provides a method of treating a patient diagnosed with a pulmonary disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, and 4 of human periostin. In other aspects, this disclosure provides a method of treating a patient diagnosed with a pulmonary disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, 4, 7, and 8 of human periostin. In certain aspects, the one or more anti-periostin antibodies are one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects this disclosure provides a method of treating a patient diagnosed with a chronic inflammatory skin disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, and 4 of human periostin. In other aspects, this disclosure provides a method of treating a patient diagnosed with a chronic inflammatory skin disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize at least isoforms 1, 2, 3, 4, 7, and 8 of human periostin. In certain aspects, the one or more anti-periostin antibodies are one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, the immunoassay is performed on a sample obtained from the patient, by the healthcare professional treating the patient, e.g., using an immunoassay as described herein, formulated as a "point of care" diagnostic kit. In some aspects, a sample is obtained from the patient and is submitted, e.g., to a clinical laboratory, for measurement of the periostin level in the sample, e.g., using an immunoassay as described herein. In certain aspects, the clinical laboratory performing the assay will advise the healthcare provide as to whether the patient can benefit from treatment with an IL-13 antagonist based on whether the patient's periostin level is above a predetermined threshold value or is elevated relative to one or more control samples.

In certain aspects, this disclosure provides a method of treating a patient diagnosed with a pulmonary disease or disorder comprising: submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, and 4 of human periostin; administering an IL-13 antagonist to a patient if the patient's periostin level in the first sample is above a predetermined threshold level, or is elevated relative to the periostin level in one or more control samples. In other aspects, this disclosure provides a method of treating a patient diagnosed with a pulmonary disease or disorder comprising: submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, 4, 7, and 8 of human periostin; administering an IL-13 antagonist to a patient if the patient's periostin level in the first sample is above a predetermined threshold level, or is elevated relative to the periostin level in one or more control samples. The periostin levels can be measured by a healthcare professional or by a clinical laboratory that obtains a patient sample from a healthcare professional, and is instructed to measure the periostin in the sample by the healthcare professional.

In certain aspects, this disclosure provides a method of treating a patient diagnosed with a chronic inflammatory skin disease or disorder comprising: submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, and 4 of human periostin; administering an IL-13 antagonist to a patient if the patient's periostin level in the first sample is above a predetermined threshold level, or is elevated relative to the periostin level in one or more control samples. In other aspects, this disclosure provides a method of treating a patient diagnosed with a chronic inflammatory skin disease or disorder comprising: submitting a first sample taken from the patient for measurement of a first periostin level in the sample, wherein the patient's periostin level is measured in an immunoassay employing one or more anti-periostin antibodies or antigen binding fragments thereof which recognize at least isoforms 1, 2, 3, 4, 7, and 8 of human periostin; administering an IL-13 antagonist to a patient if the patient's periostin level in the first sample is above a predetermined threshold level, or is elevated relative to the periostin level in one or more control samples. The periostin levels can be measured by a healthcare professional or by a clinical laboratory that obtains a patient sample from a healthcare professional, and is instructed to measure the periostin in the sample by the healthcare professional.

In certain aspects the method of treatment provided above can further comprise: submitting a second sample taken from the patient for measurement of a second periostin level in the sample, wherein the patient's periostin level is again measured in an immunoassay employing one or more antiperiostin antibodies or antigen binding fragments thereof which recognize at least isoforms 1, 2, 3, and 4 of human periostin; increasing or maintaining the amount or frequency of the IL-13 antagonist administered to the patient, or even discontinuing IL-13 antagonist therapy if the patient's periostin level in the second sample is higher than the periostin level in the first sample, or maintaining or reducing the amount or frequency of the IL13 antagonist administered to the patient if the patient's periostin level in the second sample is lower than or about the same as the periostin level in the first sample. In other aspects, the method of treatment provided above can further comprise: submitting a second sample taken from the patient for measurement of a second periostin level in the sample, wherein the patient's periostin level is again measured in an immunoassay employing one or more anti-periostin antibodies or antigen binding fragments thereof which recognize at least isoforms 1, 2, 3, 4, 7, and 8 of human periostin; increasing or maintaining the amount or frequency of the IL-13 antagonist administered to the patient, or even discontinuing IL-13 antagonist therapy if the patient's periostin level in the second sample is higher than the periostin level in the first sample, or maintaining or reducing the amount or frequency of the IL-13 antagonist administered to the patient if the patient's periostin level in the second sample is lower than or about the same as the periostin level in the first sample. It is important to note that the methods provided here are guidelines for a healthcare provider to administer treatment, and the ultimate treatment decision will be based on the healthcare provider's sound judgment.

In certain aspects, this disclosure provides a method of determining whether to treat a patient diagnosed with a pulmonary disease or disorder with an IL-13 antagonist therapeutic regimen comprising: measuring, or instructing a clinical laboratory to measure the periostin level in a first sample obtained from a patient diagnosed with a pulmonary disease or disorder, wherein the patient's periostin level is measured in an immunoassay employing one or more anti-periostin antibodies or antigen binding fragments thereof which recognize at least isoforms 1, 2, 3, and 4 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples. In other aspects, this disclosure provides a method of determining whether to treat a patient diagnosed with a pulmonary disease or disorder with an IL-13 antagonist therapeutic regimen comprising: measuring, or instructing a clinical laboratory to measure the periostin level in a first sample obtained from a patient diagnosed with a pulmonary disease or disorder, wherein the patient's periostin level is measured in an immunoassay employing one or more anti-periostin antibodies or antigen binding fragments thereof which recognize at least isoforms 1, 2, 3, 4, 7, and 8 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples.

In certain aspects, this disclosure provides a method of determining whether to treat a patient diagnosed with a chronic inflammatory skin disease or disorder with an IL-13 antagonist therapeutic regimen comprising: measuring, or instructing a clinical laboratory to measure the periostin level in a first sample obtained from a patient diagnosed with a chronic inflammatory skin disease or disorder, wherein the patient's periostin level is measured in an immunoassay employing one or more anti-periostin antibodies or antigen binding fragments thereof which recognize at least isoforms 1, 2, 3, and 4 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples. In other aspects, this disclosure provides a method of determining whether to treat a patient diagnosed with a chronic inflammatory skin disease or disorder with an IL-13 antagonist therapeutic regimen comprising: measuring, or instructing a clinical laboratory to measure the periostin level in a first sample obtained from a patient diagnosed with a chronic inflammatory skin disease or disorder, wherein the patient's periostin level is measured in an immunoassay employing one or more anti-periostin antibodies or antigen binding fragments thereof which recognize at least isoforms 1, 2, 3, 4, 7, and 8 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples.

In certain aspects, the results of the immunoassay can be submitted to a healthcare benefits provider to determine whether the patient's insurance will cover treatment with an IL-13 antagonist.

In certain aspects, the pulmonary disease or disorder to be treated is asthma, IPF, COPD, allergic rhinitis, or chronic rhinosinusitis, or the inflammatory bowel disease is ulcerative colitis (UC). In certain aspects, the chronic inflammatory skin disease or disorder to be treated is atopic dermatitis.

In certain aspects, the IL-13 antagonist comprises one or more of an anti-IL-13 antibody or antigen-binding fragment thereof e.g., tralokinumab (SEQ ID NOs 8-9), described herein, an IL-13 mutein, e.g., IL-13E13K (Kioi M, et al., Cell Immunol. 2004 229:41-51), an IL-4 mutein, e.g., Pitrakinra (AER-001, BAY-16-9996) (Antoniu S A., Curr Opin Investig Drugs. 2010 11:1286-94), an anti-IL-13Rα1 antibody or antigen-binding fragment thereof, or an anti-IL-4Rα antibody or antigen-binding fragment thereof.

In certain aspects, the patient has been treated with one or more additional medications, either before, during, or after administration of an IL-13 antagonist. Various other medications useful for treating, e.g., asthma, IPF, COPD, and UC are described elsewhere herein. In some embodiments, the various other medications useful for treating atopic dermatitis are described elsewhere herein. In certain aspects the patient has been treated, continues to be treated, or will be treated with one or more additional medications such as steroids, a bronchodilator, or a combination thereof. In certain aspects, the steroid is fluticasone or budesonide, and the bronchodilator is salbutamol. In certain aspects, the one or more additional medications are administered by inhalation, by oral administration, by injection, or a combination thereof.

In certain aspects, the IL-13 antagonist is an anti-IL13 antibody, or antigen-binding fragment thereof. In certain aspects, the anti IL-13 antibody or fragment thereof binds to the same IL-13 epitope as tralokinumab or competitively inhibits binding of tralokinumab to IL-13, or both. In certain aspects the antibody is tralokinumab or an antigen-binding fragment thereof (SEQ ID NOs 8-9).

In certain aspects, the amount of periostin measured in a sample from a subject can be at least about 5 ng periostin/ mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. The amount of periostin measured in a sample from a subject can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. The amount of periostin measured in a sample from a subject can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum.

In certain aspects, the amount of periostin measured in a sample from a subject can be at least about 5 pg periostin/mg total protein, at least about 10 pg periostin/mg total protein, at least about 15 pg periostin/mg total protein, at least about 16.44 pg periostin/mg total protein, at least about 20 pg periostin/mg total protein, at least about 25 pg periostin/mg total protein, at least about 30 pg periostin/mg total protein, at least about 35 pg periostin/mg total protein, at least about 40 pg periostin/mg total protein, at least about 45 pg periostin/mg total protein, at least about 50 pg periostin/mg total protein, at least about 55 pg periostin/mg total protein, at least about 60 pg periostin/mg total protein, at least about 65 pg periostin/mg total protein, at least about 70 pg periostin/mg total protein, at least about 75 pg periostin/mg total protein, at least about 80 pg periostin/mg total protein, at least about 85 pg periostin/mg total protein, at least about 90 pg periostin/mg total protein, at least about 95 pg periostin/mg total protein, at least about 100 pg periostin/mg total protein, at least about 105 pg periostin/mg total protein, at least about 110 pg periostin/mg total protein, at least about 115 pg periostin/mg total protein, at least about 120 pg periostin/mg total protein, at least about 125 pg periostin/mg total protein, at least about 130 pg periostin/mg total protein, at least about 135 pg periostin/mg total protein, at least about 140 pg periostin/mg total protein, at least about 145 pg periostin/mg total protein, or at least about 150 pg periostin/mg total protein. The amount of periostin measured in a sample from a subject can be less than about 150 pg periostin/mg total protein, less than about 145 pg periostin/mg total protein, less than about 140 pg periostin/mg total protein, less than about 135 pg periostin/mg total protein, less than about 130 pg periostin/mg total protein, less than about 125 pg periostin/mg total protein, less than about 120 pg periostin/mg total protein, less than about 115 pg periostin/mg total protein, less than about 110 pg periostin/mg total protein, less than about 105 pg periostin/mg total protein, less than about 100 pg periostin/mg total protein, less than about 95 pg periostin/mg total protein, less than about 90 pg periostin/mg total protein, less than about 85 pg periostin/mg total protein, less than about 80 pg periostin/mg total protein, less than about 75 pg periostin/mg total protein, less than about 70 pg periostin/mg total protein, less than about 65 pg periostin/mg total protein, less than about 60 pg periostin/mg total protein, less than about 55 pg periostin/mg total protein, less than about 50 pg periostin/mg total protein, less than about 45 pg periostin/mg total protein, less than about 40 pg periostin/mg total protein, less than about 35 pg periostin/mg total protein, less than about 30 pg periostin/mg total protein, less than about 25 pg periostin/mg total protein, less than about 20 pg periostin/mg total protein, less than about 16.44 pg periostin/mg total protein, less than about 15 pg periostin/mg total protein, less than about 10 pg periostin/mg total protein, or less than about 5 pg periostin/mg total protein. The amount of periostin measured in a sample from a subject can be about 4.5 to about 150 pg periostin/mg total protein, about 4.5 to about 125 pg periostin/mg total protein, about 4.5 to about 100 pg periostin/mg total protein, about 4.5 to about 75 pg periostin/mg total protein, about 4.5 to about 50 pg periostin/mg total protein, about 4.5 to about 25 pg periostin/mg total protein, about 5 to about 150 pg periostin/mg total protein, about 5 to about 125 pg periostin/mg total protein, about 5 to about 100 pg periostin/mg total protein, about 5.2 to about 73.3 pg periostin/mg total protein, about 5 to about 75 pg periostin/mg total protein, about 5 to about 50 pg periostin/ mg total protein, about 5 to about 25 pg periostin/mg total protein, about 25 to about 150 pg periostin/mg total protein, about 25 to about 125 pg periostin/mg total protein, about 25 to about 100 pg periostin/mg total protein, about 25 to about 75 pg periostin/mg total protein, about 25 to about 50 pg periostin/mg total protein, about 50 to about 150 pg periostin/mg total protein, about 50 to about 125 pg periostin/mg total protein, about 50 to about 100 pg periostin/mg total protein, about 50 to about 75 pg periostin/mg total protein, about 100 to about 150 pg periostin/mg total protein, about 100 to about 125 pg periostin/mg total protein, or about 125 to about 150 pg periostin/mg total protein.

Periostin Detection Assays and Kits

This disclosure also provides kits for use in the practice of the immunoassays as disclosed herein. Such kits can comprise containers, each with one or more of the various reagents (e.g., in concentrated form) utilized in the methods, including, for example, one or more anti-periostin antibodies. One or more anti-periostin antibodies, e.g., capture antibodies can be provided already attached to a solid support, and one or more antibodies, e.g., detection antibodies, can be provided already conjugated to a detectable label, e.g., biotin or a ruthenium chelate. The kit can also provide reagents for coupling a detectable label to an antibody (as well as the label itself), buffers, and/or reagents and instrumentation to support the practice of the assays provided herein. In certain aspects, a labeled secondary antibody is provided that binds to the detection antibody. A kit provided according to this disclosure can further comprise suitable containers, plates and any other reagents or materials necessary to practice the assays provided herein.

A kit for measuring periostin levels in a sample can comprise one or more of the anti-periostin antibodies or fragments thereof provided herein, e.g., one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, a kit as provided herein comprises two isolated antibodies or antigen-binding fragments thereof, a capture antibody and a detection antibody. In certain aspects, the capture antibody is 7B5.C4 or an antigen-binding fragment thereof and the detection antibody is 4B4.B11 or an antigen-binding fragment thereof. In certain aspects, the detection antibody is detectably labeled. In certain aspects, the detectable label is biotin and the detection reagents comprise a streptavidin-horse radish peroxidase (HRP) conjugate and a colorimetric substrate for HRP. In certain aspects the detectable label is a ruthenium chelate. Other antibodies, labels, and reagents as described elsewhere herein can also be used in kit as provided herein.

In certain aspects, this disclosure provides an immunoassay for detecting periostin levels in one or more samples, comprising the use of one or more anti-periostin antibodies or antigen-binding fragments thereof, wherein the one or more antibodies or fragments thereof recognize at least isoforms 1, 2, 3, and 4 of human periostin e.g., one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein. In other aspects, this disclosure provides an immunoassay for detecting periostin levels in one or more samples, comprising the use of one or more anti-periostin antibodies or antigen-binding fragments thereof, wherein the one or more antibodies or fragments thereof recognize at least isoforms 1, 2, 3, 4, 7, and 8 of human periostin e.g., one or more of murine monoclonal antibodies 4B4.B11, 7B5.C4, and 3C11.G5, as described herein, or antigen-binding fragments, variants or derivatives thereof, or related antibodies or antigen-binding fragments thereof, also as described herein.

In certain aspects, the immunoassay provided herein is a sandwich immunoassay, e.g., an ELISA assay or an ECL assay, comprising a first anti-periostin "capture" antibody or antigen-binding fragment thereof attached to a solid support, and a second anti-periostin "detection" antibody or antigen binding fragment thereof. The immunoassay is performed by methods provided herein or methods well known and understood by those of ordinary skill in the art. In one aspect the immunoassay comprises attaching a capture antibody or fragment thereof to a solid support; applying the test sample or a control sample, allowing periostin, if present in the sample, to bind to the capture antibody or fragment thereof; applying the detection antibody or fragment thereof, which can bind to periostin already bound to the capture antibody or fragment thereof; and measuring the amount of detection antibody or fragment thereof bound to periostin. In certain aspects, the assay can further include washing steps, blocking steps and incubation steps.

In certain aspects, the detection antibody or fragment thereof further comprises a detectable label, e.g., biotin or ruthenium chelate. In certain aspects the capture antibody is 3C11.G5 or 7B5.C4. In certain aspects the detection antibody is 4B4.B11 or 7B5.C4. In certain aspects the capture antibody is 7B5.C4 and the detection antibody is 4B4.B11.

In certain aspects, the amount of periostin measured in a sample can be at least about 5 ng periostin/mL serum, at least about 10 ng periostin/mL serum, at least about 15 ng periostin/mL serum, at least about 16.44 ng periostin/mL serum, at least about 20 ng periostin/mL serum, at least about 25 ng periostin/mL serum, at least about 30 ng periostin/mL serum, at least about 35 ng periostin/mL serum, at least about 40 ng periostin/mL serum, at least about 45 ng periostin/mL serum, at least about 50 ng periostin/mL serum, at least about 55 ng periostin/mL serum, at least about 60 ng periostin/mL serum, at least about 65 ng periostin/mL serum, at least about 70 ng periostin/mL serum, at least about 75 ng periostin/mL serum, at least about 80 ng periostin/mL serum, at least about 85 ng periostin/mL serum, at least about 90 ng periostin/mL serum, at least about 95 ng periostin/mL serum, at least about 100 ng periostin/mL serum, at least about 105 ng periostin/mL serum, at least about 110 ng periostin/mL serum, at least about 115 ng periostin/mL serum, at least about 120 ng periostin/mL serum, at least about 125 ng periostin/mL serum, at least about 130 ng periostin/mL serum, at least about 135 ng periostin/mL serum, at least about 140 ng periostin/mL serum, at least about 145 ng periostin/mL serum, or at least about 150 ng periostin/mL serum. The amount of periostin measured in a sample can be less than about 150 ng periostin/mL serum, less than about 145 ng periostin/mL serum, less than about 140 ng periostin/mL serum, less than about 135 ng periostin/mL serum, less than about 130 ng periostin/mL serum, less than about 125 ng periostin/mL serum, less than about 120 ng periostin/mL serum, less than about 115 ng periostin/mL serum, less than about 110 ng periostin/mL serum, less than about 105 ng periostin/mL serum, less than about 100 ng periostin/mL serum, less than about 95 ng periostin/mL serum, less than about 90 ng periostin/mL serum, less than about 85 ng periostin/mL serum, less than about 80 ng periostin/mL serum, less than about 75 ng periostin/mL serum, less than about 70 ng periostin/mL serum, less than about 65 ng periostin/mL serum, less than about 60 ng periostin/mL serum, less than about 55 ng periostin/mL serum, less than about 50 ng periostin/mL serum, less than about 45 ng periostin/mL serum, less than about 40 ng periostin/mL serum, less than about 35 ng periostin/mL serum, less than about 30 ng periostin/mL serum, less than about 25 ng periostin/mL serum, less than about 20 ng periostin/mL serum, less than about 16.44 ng periostin/mL serum, less than about 15 ng periostin/mL serum, less than about 10 ng periostin/mL serum, or less than about 5 ng periostin/mL serum. The amount of periostin measured in a sample can be about 4.5 to about 150 ng periostin/mL serum, about 4.5 to about 125 ng periostin/mL serum, about 4.5 to about 100 ng periostin/mL serum, about 4.5 to about 75 ng periostin/mL serum, about 4.5 to about 50 ng periostin/mL serum, about 4.5 to about 25 ng periostin/mL serum, about 5 to about 150 ng periostin/mL serum, about 5 to about 125 ng periostin/mL serum, about 5 to about 100 ng periostin/mL serum, about 5.2 to about 73.3 ng periostin/mL serum, about 5 to about 75 ng periostin/mL serum, about 5 to about 50 ng periostin/mL serum, about 5 to about 25 ng periostin/mL serum, about 25 to about 150 ng periostin/mL serum, about 25 to about 125 ng periostin/mL serum, about 25 to about 100 ng periostin/mL serum, about 25 to about 75 ng periostin/mL serum, about 25 to about 50 ng periostin/mL serum, about 50 to about 150 ng periostin/mL serum, about 50 to about 125 ng periostin/mL serum, about 50 to about 100 ng periostin/mL serum, about 50 to about 75 ng periostin/mL serum, about 100 to about 150 ng periostin/mL serum, about 100 to about 125 ng periostin/mL serum, or about 125 to about 150 ng periostin/mL serum.

In certain aspects, the amount of periostin measured in a sample can be at least about 5 pg periostin/mg total protein, at least about 10 pg periostin/mg total protein, at least about 15 pg periostin/mg total protein, at least about 16.44 pg periostin/mg total protein, at least about 20 pg periostin/mg total protein, at least about 25 pg periostin/mg total protein, at least about 30 pg periostin/mg total protein, at least about 35 pg periostin/mg total protein, at least about 40 pg periostin/mg total protein, at least about 45 pg periostin/mg total protein, at least about 50 pg periostin/mg total protein, at least about 55 pg periostin/mg total protein, at least about 60 pg periostin/mg total protein, at least about 65 pg periostin/mg total protein, at least about 70 pg periostin/mg total protein, at least about 75 pg periostin/mg total protein, at least about 80 pg periostin/mg total protein, at least about 85 pg periostin/mg total protein, at least about 90 pg periostin/mg total protein, at least about 95 pg periostin/mg total protein, at least about 100 pg periostin/mg total protein, at least about 105 pg periostin/mg total protein, at least about 110 pg periostin/mg total protein, at least about 115 pg periostin/mg total protein, at least about 120 pg periostin/mg total protein, at least about 125 pg periostin/mg total protein, at least about 130 pg periostin/mg total protein, at least about 135 pg periostin/mg total protein, at least about 140 pg periostin/mg total protein, at least about 145 pg periostin/mg total protein, or at least about 150 pg periostin/mg total protein. The amount of periostin measured in a sample can be less than about 150 pg periostin/mg total protein, less than about 145 pg periostin/mg total protein, less than about 140 pg periostin/mg total protein, less than about 135 pg periostin/mg total protein, less than about 130 pg periostin/mg total protein, less than about 125 pg periostin/mg total protein, less than about 120 pg periostin/mg total protein, less than about 115 pg periostin/mg total protein, less than about 110 pg periostin/mg total protein, less than about 105 pg periostin/mg total protein, less than about 100 pg periostin/mg total protein, less than about 95 pg periostin/mg total protein, less than about 90 pg periostin/mg total protein, less than about 85 pg periostin/mg total protein, less than about 80 pg periostin/mg total protein, less than about 75 pg periostin/mg total protein, less than about 70 pg periostin/mg total protein, less than about 65 pg periostin/mg total protein, less than about 60 pg periostin/mg total protein, less than about 55 pg periostin/mg total protein, less than about 50 pg periostin/mg total protein, less than about 45 pg periostin/mg total protein, less than about 40 pg periostin/mg total protein, less than about 35 pg periostin/mg total protein, less than about 30 pg periostin/mg total protein, less than about 25 pg periostin/mg total protein, less than about 20 pg periostin/mg total protein, less than about 16.44 pg periostin/mg total protein, less than about 15 pg periostin/mg total protein, less than about 10 pg periostin/mg total protein, or less than about 5 pg periostin/mg total protein. The amount of periostin measured in a sample can be about 4.5 to about 150 pg periostin/mg total protein, about 4.5 to about 125 pg periostin/mg total protein, about 4.5 to about 100 pg periostin/mg total protein, about 4.5 to about 75 pg periostin/mg total protein, about 4.5 to about 50 pg periostin/mg total protein, about 4.5 to about 25 pg periostin/mg total protein, about 5 to about 150 pg periostin/mg total protein, about 5 to about 125 pg periostin/mg total protein, about 5 to about 100 pg periostin/mg total protein, about 5.2 to about 73.3 pg periostin/mg total protein, about 5 to about 75 pg periostin/mg total protein, about 5 to about 50 pg periostin/mg total protein, about 5 to about 25 pg periostin/mg total protein, about 25 to about 150 pg periostin/mg total protein, about 25 to about 125 pg periostin/mg total protein, about 25 to about 100 pg periostin/mg total protein, about 25 to about 75 pg periostin/mg total protein, about 25 to about 50 pg periostin/mg total protein, about 50 to about 150 pg periostin/mg total protein, about 50 to about 125 pg periostin/mg total protein, about 50 to about 100 pg periostin/mg total protein, about 50 to about 75 pg periostin/mg total protein, about 100 to about 150 pg periostin/mg total protein, about 100 to about 125 pg periostin/mg total protein, or about 125 to about 150 pg periostin/mg total protein.

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

Materials and Methods

A. Periostin Sandwich ELISA Protocol with Biotin/Streptavidin-HRP Detection system.

Biotin/streptavidin-HRP-based sandwich ELISA assays were performed as follows. Specific details such as anti-periostin capture antibodies, samples to be tested, and anti-periostin detection antibodies are noted for specific experiments in the various examples Variations to standard ELISA protocols are well known to those of ordinary skill in the art, and can be used according to this disclosure.

High binding ELISA plates were coated with an anti-periostin capture mAb, e.g., 4B4.B11 (2 µg/mL in PBS; 100 µL/well), and were incubated overnight at 4° C. The plates were washed three times with 200 µL/well wash buffer (PBS/0.1% TWEEN-20®). Following washing, 200 µL/well block buffer (e.g., PBS/50× dilution of reagent diluent concentrate (available from R & D Systems)/0.05% TWEEN-20® or PBS/3% nonfat dry milk/0.1% TWEEN-20®) was added to each well, and the plates were incubated for one hour at room temperature. The plates were then washed three times as noted above.

For the standard curve, periostin standards (e.g., standards available from R & D Systems Cat # 3548-F2) were serially diluted in block buffer, e.g., 2-fold dilutions from 50 ng/mL to 0.78 ng/mL. Samples to be tested for periostin levels were diluted in block buffer—for example, serum samples from subjects were diluted, e.g., 1:5 or 1:10, in block buffer, cell supernatant samples were diluted, e.g., 1:2 in block buffer, or lung extract samples were diluted, e.g., 1:5 in block buffer. One hundred microliters (100 µL) of each standard or diluted sample was added in duplicate to the plates, and the plates were incubated for 1 hour at room temperature. Again, the plates were washed three times as noted above. Following washing, 100 µL of a biotinylated detection mAb (at 2 µg/mL or 5 µg/mL) was added to each well, and the plates were incubated for 1 hour at room temperature. Again, the plates were washed three times as noted above. Following washing, 100 µL of streptavidin-HRP conjugate (available from Invitrogen), diluted 1:10,000 in PBS was added to each well, and the plates were incubated for one hour at room temperature. Again, the plates were washed three times as noted above. Following washing, 75 µL/well TMB substrate (available from Invitrogen), pre-warmed to room temperature was added, the plates were incubated at room temperature in the dark for 15 minutes, and 75 µL of TMB stop solution (available from Kirkegaard and Perry Laboratories) was added to each well. Finally the plates were read on a spectrophotometer at λ=450 nm.

B. Periostin Sandwich Immunoasay Protocol Using Electrochemiluminescence (ECL) detection.

ECL-based sandwich immunoassays were performed as follows. Specific details such as anti-periostin capture antibodies, samples to be tested, and anti-periostin detection antibodies are noted for specific experiments in the various examples Variations to standard immunoassay protocols are well known to those of ordinary skill in the art, and can be used according to this disclosure.

MSD standard plates (available from Meso Scale Discovery) were coated with an anti-periostin capture mAb, e.g., 7B5.C4 (2 µg/mL in PBS; 50 µL/well), and were incubated overnight at 4° C. The plates were washed three times with 200 µL/well wash buffer (PBS/0.05% TWEEN-20®). Following washing, 150 µL/well block buffer (e.g., PBS/0.05% TWEEN-20®/0.2% I-Block Buffer (available from Applied Biosystems) was added to each well, and the plates were incubated for approximately hour at room temperature. The plates were then washed three times as noted above.

For the standard curve periostin standards (e.g., standards available from R&D Systems Cat # 3548-F2), were serially diluted in block buffer, e.g., serial dilutions from about 200 ng/mL to about 0.05 ng/mL. Samples to be tested for periostin levels were diluted in block buffer—for example, serum samples from subjects were diluted, e.g., 1:5 or 1:10, in block buffer, cell supernatant samples were diluted, e.g., 1:10 in block buffer, or lung extract samples were diluted, e.g., 1:20 in block buffer. Thirty microliters (30 µL) of each standard or diluted sample was added to the plates, and the plates were incubated for 1 hour at room temperature with gentle shaking on a plate shaker. Again, the plates were washed three times as noted above. Following washing, 30 µL of a ruthinylated detection mAb at 2 µg/mL was added to each well, and the plates were incubated for 1 hour at room temperature with gentle shaking on a plate shaker. Again, the plates were washed three times as noted above. Following washing, 150 µL 1× MSD Read Buffer (available from Meso Scale Discovery) was added to each well. Finally the plates were read on a MSD plate reader (available from Meso Scale Discovery).

Example 1

Generation and Characterization of Murine Monoclonal Antibodies Specific for Human Periostin Murine monoclonal antibodies specific for human periostin were produced by the following method. Mice were immunized with full-length recombinant human periostin, and hybridomas were generated by standard methods. Hybridoma supernatants were screened for antibodies binding to human periostin, and five hybridoma-produced antibodies were selected for further investigation from which three antibodies, 3C11.G5, 4B4.B11, and 7B5.C4, were selected for further characterization. Hybridoma cell lines expressing these three monoclonal antibodies were deposited under the Budapest Treaty at the American Type Culture Collection (ATCC) under Deposit No. PTA-120210 (4B4.B11), Deposit No. PTA-120211 (7B5.C4), and Deposit No. PTA-120209 (3C11.G5) on Apr. 17, 2013.

Several isoforms of human periostin have been identified. Four exemplary isoforms, 1, 2, 3, and 4, (SEQ ID NOs 1, 2, 3, and 4) are shown in FIG. 1. Each of these comprises a 21-amino acid signal peptide and an identical 649-amino acid N-terminal region. A 649-amino acid peptide common to the mature N-terminal region common to all four of the periostin isoforms depicted in FIG. 1 was isolated, and is depicted as "N-term" in FIG. 1 (SEQ ID NO:5).

Binding of the three monoclonal antibodies 3C11.G5, 4B4.B11, and 7B5.C4 to the common N-terminal region of human periostin was determined by an ECL immunoassay as described above. MSD plates were coated with 1 µg/mL full-length periostin (available from R & D Systems) and the N-terminal fragment described above were used as standards. Unlabeled 3C11.G5, 4B4.B11, and 7B5.C4 were used as the detection antibodies, followed by Ru-labeled anti-species antibodies. The results are shown in FIG. 2A-C. These results show that antibodies 7B5.C4, 4B4.B11 and 3C11.G5 bind to both the full-length and the N-terminal fragment of periostin.

The relative binding of 3C11.G5, 4B4.B11, and 7B5.C4 to human periostin was determined as follows. An ECL-based immunoassay was used, in which full-length recombinant human periostin (R & D systems) was coated onto MSD plates. Following washing, blocking, and washing steps similar to those described above, increasing concentrations of unlabeled mAbs 3C11.G5, 4B4.B11, and 7B5.C4, and buffer alone were added to the plates, followed by a 1-hour incubation at room temperature. Following washing, 2 µg/mL of Ru-labeled 3C11.G5 was added to the wells and incubated for 1 hour at room temperature. Following washing, 150 l of MDS Read Buffer was added to each well and the assay was read on an MSD plate reader. Assay signal for each curve was plotted relative to the signal generated with buffer alone, in the absence of competing antibody. The results are shown in FIG. 3A-C. These results demonstrate that mAbs 7B5.C4 and 3C11.G5 are competitive inhibitors, where mAb 4B4.B11 binds to a separate epitope.

Example 2

Measurement of Periostin Levels MRC5 Cells

This example shows that the periostin detection assays provided in this disclosure can be used to measure the effect of IL-13 stimulation on periostin expression in cultured cells. Cultured human lung fibroblast MRC-5 cells (cultured as suggested by ATCC) were stimulated with (+IL13 at 100 ng/mL) or without (−IL13) for 24 hours. Serial dilutions of cell supernatants were tested in the biotin/streptavidin-HRP sandwich ELISA assay described above, using 3C11.G5 as the capture antibody and biotinylated 4B4.B11 as the detection antibody (panel A) or 4B4.B11 as the capture antibody and biotinylated 7B5.C4 as the detection antibody (panel B). The results are shown in FIG. 4A-B. The results demonstrate that the periostin assays provided in this disclosure can distinguish between the periostin expression levels in IL-13 stimulated and unstimulated cells.

Example 3

Detection of Periostin Levels in Serum and Lung Tissues from Asthmatic Patients and Normal Healthy Subjects This example demonstrates how the assays provided in this disclosure can be used to screen asthma patients for those patients most likely to benefit from treatment with an IL-13 antagonist, e.g., tralokinumab (SEQ ID NOs 8-9). Serum samples were obtained from a population of asthma patients (n=79) and normal healthy donors (n=24). These samples were obtained from commercial vendors. These vendors collect samples across multiple sites, both domestic and international. The samples were part of a frozen bank and were not prospectively collected for this analysis.

Periostin levels in the serum samples were tested in the biotin/streptavidin-HRP sandwich ELISA assay described above. In this assay, 4B4.B11 was used as the capture antibody and biotinylated 7B5.C4 was used as the detection antibody. The serum levels of periostin were calculated using a purified recombinant human periostin standard curve. The results are shown in FIG. 5. FIG. 5A shows the results with all of the asthma patients combined, FIG. 5B shows the same results with the asthma patients broken down by medication status: no medication (n=7), ADVAIR® only (n=18), Albuterol plus inhaled steroids (n=16), inhaled steroids only (n=21), or oral and inhaled steroids (n=17).

Based on the results of this or a similar assay, those asthma patients who would likely benefit from IL-13 antagonist treatment can be identified. For example, those patients whose serum periostin levels are above a predetermined threshold level, e.g., above about 15 to above about 25 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 15 ng/mL to about 25 ng/mL, e.g., about 15 ng/mL, about 17 ng/mL, about 19 ng/mL, about 21 ng/mL, or about 25 ng/mL.

The assay provided in this disclosure was further used to measure periostin levels in the EPIAIRWAY™ tissue model. EpiAirway tissue models were obtained from MatTek corporation. These tissues are a 3-D model of respiratory tract tissue obtained from either normal healthy individuals or from asthma patients. The model was used to evaluate 1 normal donor and 4 asthma donors. The 4 asthma donors each had received different treatments: Advair only; oral and inhaled steroids; no medication; or albuterol only. All tissue samples were cultured in appropriate cell culture media (provided from MatTek) for 24 hrs prior to stimulation. Samples receiving steroid were pre-treated for 6 hrs with 100 nM budesonide. Samples were either unstimulated or stimulated with 50 ng/mL IL-13±budesonide for 48 hours. Periostin data were generated using the sandwich ELISA (biotin) protocol utilized for evaluating asthma serum. The results are shown in FIG. 6.

Example 4

Detection of Periostin Levels in Serum and Lung Tissues from Idiopathic Pulmonary Fibrosis (IPF) Patients and Normal Healthy Subjects This example demonstrates how the assays provided in this disclosure can be used screen IPF patients for those patients most likely to benefit from treatment with an IL-13 antagonist, e.g., tralokinumab (SEQ ID NOs 8-9). Serum samples were obtained from a population of IPF patients (n=53) and normal healthy donors (n=47). IPF serum was collected from multiple sites or were purchased from vendors. Age Range 50-80; Males=28, Females=23. Treatments of the patients, if known, included prednisone, Imuran, Cytoxan, euphylline, and acetyl cysteine. Normal samples were collected from multiple sites or were purchased from vendors. Periostin levels in the serum samples were tested in the biotin/streptavidin-HRP sandwich ELISA assay described above. The results are shown in FIGS. 7A and 7B. In this assay, 3C11.G5 was used as the capture antibody and biotinylated 4B4.B11 was used as the detection antibody (panel A), or 4B4.B11 was used as the capture antibody and biotinylated 7B5.C4 was used as the detection antibody (panel B). The serum levels of periostin were calculated using a purified recombinant human periostin standard curve.

Based on the results of this or a similar assay, those IPF patients who would likely benefit from IL-13 antagonist treatment can be identified. For example, those patients whose serum periostin levels are above a predetermined threshold level, e.g., above about 40 ng/mL to above about 60 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the lower threshold level can be within the range of about 40 ng/mL to about 60 ng/mL, e.g., about 40 ng/mL, about 43 ng/mL, about 45 ng/mL, about 48 ng/mL, about 50 ng/mL, about 53 ng/mL, about 55 ng/mL, about 58 ng/mL, or about 60 ng/mL.

The biotin/streptavidin-HRP sandwich ELISA assay described above (3C11.G5 capture/4B4.B11 detection) to detect IPF patients likely to benefit from treatment with an IL-13 antagonist was compared to that of a commercially available test (Human Periostin/OSF-2 DuoSet, Catalog No. DY3548, available from R & D Systems). The results are shown in FIGS. 7C and 7D. Serum samples from a subset of IPF patients (severe IPF that underwent lung transplant, n=10) and normal healthy donors (n=10) were tested in each assay. Unlike the existing commercially available assay, the assay provided herein detected increased periostin levels in sera from IPF patients compared to normal healthy donors.

The assay provided in this disclosure was further used to measure periostin levels in lung tissue extracts from IPF patients (n=12) and normal donors (n=12). IPF lung tissue obtained from Temple University. Normal lung tissue from the National Disease Research Interchange (NDRI) n=10 and Temple University n=2. Lung tissue was homogenized on ice using hand held tissue homogenizer then centrifuged at 4° C. for 10 min at 14000 RCF. Supernatant frozen at −80° C. The homogenates were diluted 1:5 and assayed for periostin using the biotin/streptavidin-HRP sandwich ELISA assay described above. The results (in pg of periostin per mg total protein) are shown in FIG. 8.

Based on the results of this or a similar assay, those IPF patients who would likely benefit from IL-13 antagonist treatment can be identified. For example, those patients whose lung tissue periostin levels are above a predetermined threshold level, e.g., above about 5 pg/mg to above about 15 pg/mg or to above about 25 pg/mg total protein are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 5 pg/mg total protein to about 10 pg/mg total protein or about 15 pg/mg total protein to about 25 pg/mg total protein, e.g., about 5 pg/mg, about 7 pg/mg, about 10 pg/mg, about 12 pg/mg, about 15 pg/mg, about 17 pg/mg, about 19 pg/mg, about 21 pg/mg, or about 25 pg/mg of total protein.

Example 5

Determination of Assay Specificity

This Example demonstrates the specificity of the MSD assay to detect periostin in a variety of serum samples from normal healthy individuals (n=16), asthma patients (n=16), IPF patients (n=14), or ulcerative colitis (UC) patients (n=16). For this assay, 7B5.C4 was used as the capture antibody, and Ru-labeled4B4.B11 was used as the detection antibody. In order to show specificity, duplicate serum samples were incubated with 3C11.G5 prior to the assay. The results are shown in FIG. 9. Periostin levels in all 62 individuals from normal and diseased sera were detectible at baseline. Moreover, 3C11.G5 completely blocked the detection, confirming the specificity of the 7B5.C4/4B4.B11 mAb pair for periostin detection.

Based on the results of this or a similar assay, UC patients who would likely benefit from IL-13 antagonist treatment can be identified. For example, those UC patients whose serum periostin levels are above a predetermined threshold level, e.g., above about 20 ng/mL to above about 40 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the lower threshold level can be within the range of about 20 ng/mL to about 40 ng/mL, e.g., about 20 ng/mL, about 23 ng/mL, about 25 ng/mL, about 28 ng/mL, about 30 ng/mL, about 33 ng/mL, about 35 ng/mL, about 38 ng/mL, or about 40 ng/mL.

Example 6

A Phase 2b, Randomized, Double-blind Study to Evaluate the Efficacy and Safety of SC Tralokinumab in Adults with Uncontrolled, Severe Asthma

TABLE 2

| List of Abbreviations. | |
| --- | --- |
| ACQ-6 | Asthma Control Questionnaire (6-item version) |
| AER | asthma exacerbation rate |
| AHR | airway hyperresponsiveness |
| AQLQ(S) | Standardized Asthma Quality of Life Questionnaire |
| AQLQ(s) + 12 | Standardized Asthma Quality of Life Questionnaire for 12 years and older |
| BASE | baseline $FEV_1$ |
| CI | confidence interval |
| CPAP | continuous positive airway pressure |
| DPI | dry powder inhaler |
| ePRO | electronic patient reported outcome |
| $FEV_1$ | forced expiratory volume in one second |
| HRQoL | health-related quality of life |
| $IC_{50}$ | half-maximal inhibitory concentration |
| ICS | inhaled corticosteroids |
| IgE | immunoglobulin E |
| IL-13 | interleukin-13 |
| LABA | long-acting β2 agonist |
| MCID | minimal clinical important change |
| MDI | metered dose inhaler |
| MRD | minimum required dilution |
| OCS | oral corticosteroid(s) |
| PEF | peak expiratory flow |
| PEFR | peak expiratory flow rate |
| Q2W | every 2 weeks |
| Q2/4W | every 2 weeks for 12 weeks followed by every 4 weeks |
| Q4W | every 4 weeks |
| SABA | short-acting β2 agonist |
| SC | Subcutaneous |
| SD | standard deviation |
| $t_{1/2}$ | half-life |
| TEAE | treatment-emergent adverse event |
| TESAE | treatment-emergent serious adverse event |
| Th2 | T helper type 2 |

Study Objectives & Design

Study CD-RI-CAT-354-1049 was a Phase 2b, randomized, double-blind, placebo-controlled, parallel-arm, multi-center study to evaluate the efficacy and safety of two SC treatment regimens of tralokinumab in adults with uncontrolled, severe asthma requiring high dose ICS and LABA with or without additional controller medications (high-dose ICS defined as a total daily dose >500 μg fluticasone DPI or >440 μg metered dose inhaler (MDI; Global Strategy for Asthma Management and Prevention, Global Initiative for Asthma (GINA) 2012. Available from www.ginasthma.org; National Heart, Lung, and Blood Institute National Asthma Education and Prevention Program Expert Panel Report 3: Guidelines for the Diagnosis and Management of Asthma Full Report 2007. ). A 5-week screening/run-in period (Week-5 to -1 [Day-1]) preceded randomisation. Starting at Week-4 (Day-28), patients received a fixed-dose combination product of fluticasone/salmeterol, either as an MDI (230 μg/21 μg) at a dose of 2 inhalations twice per day or as a DPI (500 μg/50 μg) at a dose of one inhalation twice per day. If the patient was also taking additional asthma controller medications (including leukotriene modifiers, theophylline, cromones, a secondary ICS, or oral prednisolone ≤20 mg/day or equivalent OCS), then these medications were to be continued at a stable dose during the screening/run-in and treatment period.

Key Inclusion Criteria:
(i) Documented physician-diagnosed asthma for at least 12 months prior to the screening/run-in period and either:
  (a) Proof of post-bronchodilator reversibility of FEV1≥12% and ≥200 mL to a SABA documented within 36 months prior to Visit 1; OR
  (b) Proof of a positive response to a methacholine (20% fall in FEV1 [PC20]≤8 mg/mL), histamine or mannitol challenge documented within 36 months prior to Visit 1; OR
  (c) A post-bronchodilator increase in FEV1≥12% and ≥200 mL at Visit 1 or 2. (A maximum of 400 μg salbutamol administered for the reversibility assessment.)
(ii) An asthma controller regimen consistent with that described at Step 4 or 5 of the GINA guidelines (GINA, 2009) for at least 6 of the 12 months prior to the screening/run-in period and must have used physician prescribed high-dose ICS in combination with LABA for at least 30 days prior to the screening/run-in period
(iii) A history of at least 2 but no more than 6 documented asthma exacerbation events within the 12 months prior to the screening/run-in period
(iv) At least one of the following; a morning prebronchodilator FEV1 value of between 40% and 80% predicted or an ACQ-6 score for the preceding week of ≥1.5 at both screening and randomisation visits.

Patients were randomised in a 1:1 ratio to one of 2 cohorts (Cohort 1 or Cohort 2). Within each cohort, patients were randomised in a 2:1 ratio to receive tralokinumab (300 mg) or placebo as follows:
Cohort 1: Tralokinumab 300 mg or Placebo as 2 SC injections Q2W for 50 weeks for a total of 26 doses.
Cohort 2: Tralokinumab 300 mg or Placebo as 2 SC injections Q2W for 12 weeks followed by Q4W for 38 weeks for a total of 16 doses.

Patients were stratified at screening by the number of asthma exacerbations in the past 12 months (2 versus>2 but≤6 exacerbations) and by chronic OCS use (presence versus absence).

The primary objective of this study was to evaluate the effect of two SC treatment regimens of tralokinumab (300 mg Q2W and 300 mg Q2/4W) on AER over 52 weeks. Secondary objectives were to evaluate the safety and tolerability of tralokinumab, the effect of tralokinumab on pulmonary function, patient reported outcomes (including ACQ-6 score and HRQoL using AQLQ[S], and asthma symptoms using the asthma daily diary).

Asthma exacerbation was defined as a progressive increase of asthma symptoms (cough, wheeze, chest tightness, and/or shortness of breath) that did not resolve after the initiation of rescue medications and remained troublesome for the patient resulting in either:
1. Use of systemic corticosteroids (tablets, suspension, or injection) or increase of a stable systemic maintenance dose for a duration of at least 3 consecutive days OR
2. Patient initiation of systemic corticosteroids for a duration of at least 3 consecutive days.

The trial was powered to detect a 40% reduction in annual AER for each tralokinumab treatment group compared to combined placebo from Cohorts 1 and 2 assuming an annual exacerbation rate in placebo group of 1.2 with 80% power and a significance level of 0.15. The sample size was adequate for prespecified subanalysis to explore the relationship between the clinical response to tralokinumab and the presence of peripheral blood biomarkers associated with upregulation of IL-13 in the asthmatic lung including serum periostin.

A total of 452 patients were randomised from 15 countries (Argentina, Canada, Chile, Czech Republic, France, Germany, Japan, Mexico, Philippines, Poland, Russia, South Korea, Spain, UK and US). All the efficacy and safety data collected through Week 53 have been analysed and summarized in U.S. Provisional App. No. 61/931,878, filed Jan. 27, 2014, herein incorporated by reference in its entirety for all purposes.

Subgroup Analysis: Baseline Serum Periostin Level

To explore the relationship between the clinical response to tralokinumab and peripheral blood biomarkers associated with upregulation of IL-13, subgroups defined by baseline serum periostin (≥median vs<median) were analyzed. The median periostin level used in the study to define high periostin was a baseline serum periostin of ≥23 ng/mL (i.e., high periostin) as measured using an immunoassay. TABLE 3.

TABLE 3

Summary of Mean and Media Periostin Levels.

| Parameter | Measure | Placebo (n = 151) | 300 mg Tralokinumab Q2W (n = 150) | 300 mg Tralokinumab Q2/4W (n = 151) |
|---|---|---|---|---|
| Periostin | N | 147 | 150 | 149 |
| | Mean (SD) | 23.959 (9.137) | 25.531 (10.656) | 25.480 (10.037) |
| | Median | 22.040 | 23.600 | 23.250 |

Subgroup analysis at Week 53 by serum periostin level at baseline showed that reductions in the annual AER were observed in the tralokinumab 300 mg Q2W cohort compared with placebo in the high periostin group (≥median serum periostin level at baseline; 25% [95% CI: −19, 53%]). No reduction in AER was observed in the low periostin group (<median serum periostin level at baseline).

Post hoc analysis explored the hypothesis that patients with FEV1 reversibility≥12% and serum periostin≥median at baseline had an enhanced treatment response to tralokinumab 300 mg Q2W. In this subset of patients the reduction in AER was 54% (95% CI: −65, 87%) and the percentage increase from baseline in pre-bronchodilator FEV1 compared to placebo 13.85% (95% CI: −0.18, 27.87), was numerically greater than in those subjects with FEV1 reversibility 12% and serum periostin<median (reduction in AER 4% [95% CI: −140, 61%] and increase in FEV1 7.62% [95% CI: −7.60, 22.84]).

Periostin levels were measured in baseline serum samples, i.e., prior to tralokinumab treatment that were collected from patients randomised in the Phase 2b study. Key study endpoints including AER reduction, FEV1, and ACQ-6 stratified by the median serum periostin level to determine if patients with baseline serum periostin levels at or above the median derive greater benefit from tralokinumab compared with those below the median. An increase in FEV, (6.75% for patients with baseline serum periostin at or above median vs 8.65% for patients regardless of serum periostin level) and greater AER reduction (25% for patients with serum periostin at or above median vs 7% for patients regardless of serum periostin level) with tralokinumab 300 mg Q2W were observed at Week 53. FIGS. 11A-B; TABLE 4. The median periostin level used in the study to define high periostin was a baseline serum periostin of about ≥23 ng/mL (i.e., high periostin) as measured using an immunoassay. For a continuous representation of AER reduction by periostin level and percent change from baseline in pre-bronchodilator FEV, by serum periostin level, see FIG. 10.

In post-hoc analysis, reversible patients (post-bronchodilator reversibility of FEV,≥12%) with baseline serum periostin levels≥median had a greater increase in FEV, (13.85% for reversible patients with serum periostin at or above median vs 11.07% for reversible patients regardless of serum periostin level) and greater AER reduction (54% for reversible patients with serum periostin at or above median vs 34% for reversible patients regardless of serum periostin level).

Serum periostin levels were substantially reduced by tralokinumab soon after the first dose and remained low for the duration of the study. Greater reduction in serum periostin levels was observed in those patients whose serum periostin levels at baseline were above the median compared to those below the median. These results provided further support that serum periostin is a surrogate marker for the IL-13 pathway.

TABLE 4

Summary of Primary and secondary efficacy endpoints for tralokinumab 300 mg Q2W ITT and periostin subgroups.

|  | ITT (N = 150) | Periostin ≥ Median (N = 80) | Periostin < Median (N = 80) |
| --- | --- | --- | --- |
| Asthma exacerbation rate reduction<sup>a</sup> (95% CI) | 7% (−30%, 33%) P = 0.669 | 25% (−19%, 53%) P = 0.219 | −8% (−73%, 32%) P = 0.742 |
| Percent change from baseline in FEV$_1$ (95% CI) | 7.1 (2.35, 11.84) P = 0.003 | 6.8 (−0.31, 13.82) P = 0.061 | 7.06 (0.51, 13.60) P = 0.035 |
| Change from baseline in ACQ-6 (95% CI) | −0.18 (−0.43, 0.06) P = 0.137 | −0.23 (−0.56, 0.09) P = 0.163 | −0.02 (−0.38, 0.34) P = 0.919 |
| Change from baseline in AQLQ (95% CI) | 0.21 (−0.05, 0.46) P = 0.114 | 0.22 (−0.15, 0.59) P = 0.245 | 0.21 (−0.16, 0.58) P = 0.272 |

In conclusion, in the Phase 2b Study the following observations were made:
1. The AER appeared higher in placebo patients with baseline serum periostin levels the median (~23 ng/mL as measured by immunoassay) suggesting that it may be associated with severity of disease.
2. High periostin on entry (~23 ng/mL as measured by immunoassay) appeared to be associated with a greater response to treatment with Tralokinumab which was further enhanced in a post-hoc subgroup analysis of both high periostin and FEV1 reversibility≥12% on entry.

Based on the results of this study, those asthma patients who would likely benefit from IL-13 antagonist treatment can be identified. For example, those asthma patients whose serum periostin levels are above a predetermined threshold level, e.g., above about 23 ng/mL to above about 25 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 23 ng/mL to about 25 ng/mL, e.g., about 23 ng/mL, about 24 ng/mL, or about 25 ng/mL.

These findings are consistent with previous studies with lebrikizumab, an antibody that also targets IL-13. In a subgroup analysis of a Phase 2 study of patients with uncontrolled asthma, larger increases in FEV1 and greater AER reduction were reported in patients treated with lebrikizumab with above-median baseline serum periostin levels compared with those with baseline serum periostin levels below the median. See Corren et al. N Engl J Med. 365(12): 1088-98 (2011), herein incorporated by reference in its entirety for all purposes. Based on the results of this study, those asthma patients who would likely benefit from IL-13 antagonist treatment can be identified. For example, those asthma patients whose serum periostin levels are above a predetermined threshold level, e.g., periostin levels above the median level for serum periostin in asthma patients; with the use of the median value for all patients defining the cutoff point between a high-periostin subgroup (median value or higher) and a low-periostin subgroup (less than the median value).

Similarly, our results are also consistent with Jia et al, J Allergy Clin Immunol. 130(3):647-654 (2012) (herein incorporated by reference in its entirety for all purposes) reporting a median serum periostin level in asthma patients of about 25 ng/mL. Accordingly, based on the results of this study, those asthma patients who would likely benefit from IL-13 antagonist treatment can be identified. For example, those patients whose serum periostin levels are above a predetermined threshold level, e.g., above about 25 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 19 ng/mL to about 30 ng/mL, e.g., about 19 ng/mL, about 21 ng/mL, about 23 ng/mL, about 25 ng/mL, about 27 ng/mL, or about 30 ng/mL.

These findings are also consistent with PCT/US2011/065410 (WO 2012/083132; herein incorporated by reference in its entirety for all purposes) reporting that high serum periostin levels in moderate to severe asthmatic patients range from about 20 ng/mL, to about 25 ng/mL, or to about 50 ng/mL. Accordingly, based on the results of these studies, those asthma patients who would likely benefit from IL-13 antagonist treatment can be identified. For example, those patients whose serum periostin levels are above a predetermined threshold level, e.g., above about 20 to above about 25 ng/mL and/or to above about 50 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 20 ng/mL to about 25 ng/mL or about 25 ng/mL to about 50 ng/mL, e.g., about 20 ng/mL, about 22 ng/mL, about 24 ng/mL, about 25 ng/mL, about 27 ng/mL, about 29 ng/mL, about 31 ng/mL, about 33 ng/mL, about 35 ng/mL, about 37 ng/mL, about 39 ng/mL, about 41 ng/mL, about 43 ng/mL, about 45 ng/mL, about 47 ng/mL, about 49 ng/mL or about 50 ng/mL.

These findings are also consistent with PCT/US2009/039033 (WO 2009/124090; herein incorporated by reference in its entirety for all purposes) reporting a median serum periostin levels in asthma patients of about 52 ng/mL (for all patients), about 54 ng/mL (patients not taking inhaled corticosteroids) or about 48 ng/mL (patients taking inhaled corticosteroids). Accordingly, based on these results, those asthma patients who would likely benefit from IL-13 antagonist treatment can be identified. For example, those patients whose serum periostin levels are above a predetermined threshold level, e.g., above about 48 to above about 54 ng/mL are identified as likely to benefit from IL-13 antagonist treatment either alone, or in combination with an existing therapy. In certain aspects, the predetermined threshold level can vary, depending upon other variables in the patient's condition, to be determined, e.g., by a healthcare professional. For example the threshold level can be within the range of about 48 ng/mL to about 54 ng/mL, e.g., about 48 ng/mL, about 49 ng/mL, about 50 ng/mL, about 51 ng/mL, about 52 ng/mL, about 53 ng/mL, or about 54 ng/mL.

Example 7

Testing of Antibody Binding to Periostin Isoforms

Serum periostin has been proposed as a systemic surrogate biomarker of IL-13 pathway activation in the lung. To enable its use as a potential clinical diagnostic, an automated investigational use only (IUO) immunoassay was developed to detect serum periostin on the ARCHITECT® immunoassay iSystem. As such, antibodies were tested for their ability to detect the five periostin isoforms 2, 3, 4, 7, and 8 (SEQ ID NOs: 2-4 and 16-17) found in lung tissue.

Expression constructs. The DNA sequence for periostin isoform 1 was obtained from NCBI reference sequence NM_006475.2 (last modified: Apr. 20, 2014; SEQ ID NO: 10). The DNA sequences for isoforms 2, 3, 4, 7, and 8 (SEQ ID NOs: 11-15) were then determined from the literature (Hoersch et al. BMC Evolutionary Biology 2010, 10, 30), and are shown as an exon map in FIG. 12. The sequences were submitted to GenScript USA, Inc. (Piscataway, N.J.) where they were subjected to GenScript's algorithm for optimizing codon usage for maximum expression in human cells. The DNA was synthesized and inserted into the expression vector pcDNA3.1+ (Life Technologies, Grand Island, N.Y.). The constructs were sequenced, the sequences were translated using Vector NTI software (v11, Life Technologies), and the sequences were aligned with the original protein sequences to verify that the codon optimized sequences coded for identical amino acid sequences derived from the NCBI reference sequence.

Cell Culture and Transient Transfection. Human embryonic kidney cells (HEK-293-6E, National Research Council Canada) were propagated in suspension culture using FreeStyle 293 media (Life Technologies). Flasks were seeded with $0.5 \times 10^6$ cells/mL in 100 mL media and incubated for 2 days at 37° C. in 8% $CO_2$. The cells were then transfected with plasmid DNA using polyethylenimine (PEI, Polysciences, Inc., Warrington, Pa.) at a DNA:PEI ratio of 1:2.5 using 0.75 pg DNA per cell. At 4 hours post-transfection, the cultures were fed with Tryptone N1 (10% solution, weight/volume, in culture media, Organotechnie, La Courneuve, France) at 5 mL/100 mL culture media. At 6 days post-transfection, the cultures were harvested and the media clarified by centrifugation. A flask of cells that were not transfected was incubated for 6 days, harvested, and clarified to use as a media control. A transfection control was also included in the testing by transfecting plasmid DNA coding a protein unrelated to periostin using the same conditions and harvesting the media at 6 days post-transfection. All five isoforms were expressed and secreted into the media.

Western Blotting. The binding of anti-periostin antibodies 4B4.B11 and 7B5.C4 to periostin isoforms was analyzed and confirmed by Western blotting. The expressed periostin isoforms were separated by SDS-PAGE under non-denaturing conditions. 20 μL clarified media and 5 μL sample buffer per lane were applied to 4-12% Criterion XT gels (Bio-Rad) using MOPS running buffer and XT sample buffer (no reductant). The periostin isoforms 1, 2, 3, 4, 7, and 8 were loaded in the well in an amount of 23.5, 133.1, 154.4, 194.4, 106.8, and 73.0 ng per well, respectively. The separated proteins were stained using Oriole fluorescent stain as shown in FIG. 13.

The separated proteins on duplicate gels were transfer to nitrocellulose using the iBlot system. Western blot analysis using anti-periostin antibody 4B4.B11 was performed using the Snap ID detection system (EMD Millipore). Western blot analysis using the anti-periostin antibody 7B5.C4 was performed using a standard protocol with 3.5 h incubation. As shown in FIG. 14A, antibody 4B4.B11 detected all 6 isoforms in the Western blot run under non-reducing conditions. As shown in FIG. 14B, antibody 7B5.C4 reacted poorly in the Western blot, but did detect all 5 isoforms (isoforms 2, 3, 4, 7, and 8) found in lung tissue.

ARCHTIECT® Periostin Assay. The anti-periostin antibodies were used in the ARCHITECT® system. The ARCHITECT® sandwich immunoassay principle is shown in FIG. 15. Briefly, an antibody coated on a microparticle captured the analyte of interest, then a second antibody conjugated to acridinium bound to a second epitope on the analyte, then a separation of the particles from the label and subsequent read was performed to determine the relative light units (RLU) from the chemiluminescence reaction. The ARCHITECT® periostin assay is a two-step immunoassay for the quantitative determination of periostin in human serum using Chemiluminescent Magnetic Immunoassay (CMIA) technology. More specifically, periostin present in the patient sample was captured by microparticles coated with a monoclonal antibody against recombinant periostin. After incubation and washing, a second newly developed anti-periostin monoclonal conjugated with acridinium was added, and chemiluminesence was triggered and measured as relative light units (RLUs). A direct relationship existed between the amount of periostin in the sample and the RLUs detected by the ARCHITECT® /System optics. The assay was completed in less than 20 min. The analytical performance of the ARCHITECT® periostin assay was assessed by precision, sensitivity, linearity, endogenous and drug interfering substances, specimen handling/preanalytics, and periostin isoform reactivity studies.

The ARCHITECT Periostin assay was performed on 1:60 or 1:100 diluted harvested media from the periostin transfections and the controls (undiluted). The anti-periostin antibody 4B4.B11 was used as the capture antibody at a concentration of 0.2 mg/mL and paired with the anti-periostin antibody 7B5.C4 as the detection antibody at a concentration of 1 nM final assay concentration. Microparticles were coated with capture antibody at a concentration of 0.2 mg/mL. The microparticle solution was approximately 0.12% solids. In the capture step after periostin isoform and detection antibody addition, the capture reaction was 0.06% solids. A preliminary phase 3 stratification cut-off of 16.44 ng/mL was used to determine reactivity to the expressed isoforms. Five-day precision results were <6.4% CV across 3 controls and 3 serum based panels. Limit of quantitation was </=4 ng/mL. Specimen dilution analysis yielded linear results across the dynamic range of the assay (4-100 ng/mL). No endogenous sample and drug interferences were observed. Periostin in serum left on clot and in serum separator tubes (SST) was stable at room temperature, and refrigerated for up to 24 hours, and for up to 2 freeze/ thaw cycles. For specimens that were not tested within 24 hours of collection, freezing (−10° C. or colder) for long term storage was recommended.

The results, corrected for dilution, are shown in Table 5. The Media Control and Transfection Control were tested undiluted and did not react in the assay. All 5 isoforms that are found in lung tissue (isoforms 2, 3, 4, 7, and 8) were detected by the antibodies used in the ARCHITECT Periostin assay. Using this newly developed IUO assay, serum periostin in over 1000 serum samples from patients with moderate to severe asthma was measured. The range was 5.2-73.3 ng/mL and the median periostin level was 16.44 ng/mL. The IUO ARCHITECT® periostin immunoassay was determined to be a reliable and robust test to measure serum periostin levels.

TABLE 5

ARCHITECT ® Periostin assay results.

| Sample Tested (dilution) | AVG ng/mL (corrected for dilution) |
|---|---|
| Media Control | −0.132 |
| Transfection Control | −0.066 |
| Isoform 2 (1:100) | 6655.5 |
| Isoform 3 (1:100) | 7719.50 |
| Isoform 4 (1:100) | 9720.50 |
| Isoform 7 (1:60) | 5337.53 |
| Isoform 8 (1:60) | 3651.05 |

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of treating a patient having an IL-13-mediated disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, and 4 of human periostin.

Clause 2. A method of treating a patient having an IL-13-mediated disease or disorder, comprising administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, and 4 of human periostin.

Clause 3. The method of clause 1 or clause 2, wherein a sample is obtained from the patient and is submitted for measurement of the periostin level in the sample.

Clause 4. A method of treating a patient having an IL-13-mediated disease or disorder comprising submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, and 4 of human periostin; administering an IL-13 antagonist to the patient if the patient's periostin level in the first sample is above a predetermined threshold level, or is elevated relative to the periostin level in one or more control samples.

Clause 5. A method of treating a patient having an IL-13-mediated disease or disorder comprising submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, and 4 of human periostin; and administering an IL-13 antagonist to the patient identified as a candidate for treatment by having a periostin level in the first sample above a predetermined threshold level, or by having an elevated periostin level relative to a periostin level in one or more control samples.

Clause 6. The method of clause 4 or clause 5, further comprising submitting a second sample taken from the patient for measurement of a second periostin level in the sample, wherein the patient's second periostin level is measured in an immunoassay employing one or more anti-periostin antibodies or antigen binding fragments thereof which recognize isoforms 1, 2, 3, and 4 of human periostin; and increasing or maintaining the amount or frequency of the IL-13 antagonist administered to the patient if the patient's periostin level in the second sample is higher than the periostin level in the first sample, or maintaining or reducing the amount or frequency of the IL-13 antagonist administered to the patient if the patient's periostin level in the second sample is lower than or about the same as the periostin level in the first sample.

Clause 7. A method of treating a patient having an IL-13-mediated disease or disorder comprising measuring the periostin level in a first sample obtained from a patient having an IL-13-mediated disease or disorder, wherein the patient's periostin level in the first sample is measured in an immunoassay employing one or more anti-periostin antibodies or antigen binding fragments thereof which recognize isoforms 1, 2, 3, and 4 of human periostin; determining whether the patient's periostin level in the first sample is above a predetermined threshold level, or is elevated relative to the periostin level in one or more control samples; and advising a healthcare provider to administer an IL-13 antagonist to the patient if the patient's periostin level is above a predetermined threshold level, or is elevated relative to the periostin level in one or more control samples.

Clause 8. The method of clause 7, further comprising measuring the periostin level in a second sample obtained from the patient, wherein the patient's periostin level in the second sample is measured in an immunoassay employing one or more anti-periostin antibodies or antigen binding fragments thereof which recognize isoforms 1, 2, 3, and 4 of human periostin; determining whether the patient's periostin level in the second sample is higher than, about the same as, or lower than the periostin level measured in the first sample; and advising a healthcare provider to increase or maintain the amount or frequency of the IL-13 antagonist administered to the patient if the patient's periostin level in the second sample is higher than the periostin level in the first sample, or to maintain or reduce the amount or frequency of the IL-13 antagonist administered to the patient if the patient's periostin level in the second sample is lower than or about the same as the periostin level in the first sample.

Clause 9. A method of monitoring the therapeutic efficacy of an IL-13 antagonist therapeutic regimen in a patient having an IL-13-mediated disease or disorder comprising measuring, or instructing a clinical laboratory to measure the periostin level in a first sample obtained from a patient having an IL-13-mediated disease or disorder, wherein the patient's periostin level is measured in an immunoassay employing one or more anti-periostin antibodies or antigen binding fragments thereof which recognize isoforms 1, 2, 3, and 4 of human periostin; administering, or advising a healthcare professional to administer an IL-13 antagonist to a patient if the patient's periostin level in the first sample is above a predetermined threshold level, or is elevated relative to the periostin level in one or more control samples; measuring the periostin level in a second sample obtained from the patient, wherein the patient's periostin level in the second sample is measured in an immunoassay employing one or more anti-periostin antibodies or antigen binding fragments thereof which recognize isoforms 1, 2, 3, and 4 of human periostin; and determining, or obtaining results indicating whether the patient's periostin level in the second sample is higher than, about the same as, or lower than the periostin level measured in the first sample; wherein the IL-13 antagonist therapeutic regimen is effective if the patient's periostin level in the second sample is lower than or about the same as the periostin level in the first sample.

Clause 10. The method of any one of clauses 1 to 7, wherein the patient has been diagnosed with a pulmonary disease or disorder or an inflammatory bowel disease or disorder, following a differential diagnosis, and wherein the differential diagnosis includes testing for IL-13-mediated diseases or disorders.

Clause 11. The method of clause 10, wherein the differential diagnosis comprises one or more of: measuring the patient's IgE levels, measuring the patient's eosinophil count, making a symptom analysis, determining the patient's Fraction of Exhaled Nitric Oxide (FENO), and determining the patient's Eosinophil/Lymphocyte and Eosinophil/Neutrophil (ELEN) index.

Clause 12. The method of clause 10 or clause 11, wherein the pulmonary disease or disorder is asthma, idiopathic pulmonary fibrosis (IPF), chronic obstructive pulmonary disease (COPD), allergic rhinitis, chronic rhinosinusitis, or a combination of two or more thereof, or wherein the inflammatory bowel disease is ulcerative colitis (UC).

Clause 13. A method of treating a patient diagnosed with a pulmonary disease or disorder comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, and 4 of human periostin.

Clause 14. A method of treating a patient diagnosed with a pulmonary disease or disorder comprising administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, and 4 of human periostin.

Clause 15. A method of treating a patient diagnosed with a pulmonary disease or disorder comprising submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, and 4 of human periostin; administering an IL-13 antagonist to a patient if the patient's periostin level in the first sample is above a predetermined threshold level, or is elevated relative to the periostin level in one or more control samples.

Clause 16. A method of treating a patient diagnosed with a pulmonary disease or disorder comprising submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, and 4 of human periostin; and administering an IL-13 antagonist to a patient identified as a candidate for treatment by having a periostin level in the first sample above a predetermined threshold level, or by having an elevated periostin level relative to a periostin level in one or more control samples.

Clause 17. The method of clause 15 or clause 16, further comprising submitting a second sample taken from the patient for measurement of a second periostin level in the sample, wherein the patient's second periostin level is measured in an immunoassay employing one or more anti-periostin antibodies or antigen binding fragments thereof which recognize isoforms 1, 2, 3, and 4 of human periostin; and increasing or maintaining the amount or frequency of the IL-13 antagonist administered to the patient if the patient's periostin level in the second sample is higher than or about the same as the periostin level in the first sample, or maintaining or reducing the amount or frequency of the IL-13 antagonist administered to the patient if the patient's periostin level in the second sample is lower than the periostin level in the first sample.

Clause 18. A method of determining whether to treat a patient diagnosed with a pulmonary disease or disorder with an IL-13 antagonist therapeutic regimen comprising measuring, or instructing a clinical laboratory to measure the periostin level in a first sample obtained from a patient diagnosed with a pulmonary disease or disorder, wherein the patient's periostin level is measured in an immunoassay employing one or more anti-periostin antibodies or antigen binding fragments thereof which recognize isoforms 1, 2, 3, and 4 of human periostin; and treating, or instructing a healthcare provider to treat the patient with an IL-13 antagonist therapeutic regimen if the patient's periostin level in the first sample is above a predetermined threshold level, or is elevated relative to the periostin level in one or more control samples.

Clause 19. The method of any one of clauses 13 to 18, wherein the pulmonary disease or disorder is asthma, IPF, COPD, allergic rhinitis, or chronic rhinosinusitis.

Clause 20. The method of any one of clauses 1 to 19, wherein the IL-13 antagonist comprises one or more of an anti-IL-13 antibody or antigen-binding fragment thereof, an IL-13 mutein, an IL-4 mutein, an anti-IL-13Rα1 antibody or antigen-binding fragment thereof, or an anti-IL-4Rα antibody or antigen-binding fragment thereof.

Clause 21. The method of any one of clauses 13 to 20, wherein the patient has been treated with one or more additional medications, either before, during, or after administration of an IL-13 antagonist.

Clause 22. The method of clause 21, wherein the one or more additional medications comprise steroids, a bronchodilator, or a combination thereof.

Clause 23. The method of clause 22, wherein the steroid is fluticasone or budesonide, and the bronchodilator is salbutamol.

Clause 24. The method of any one of clauses 21 to 23, wherein the one or more additional medications are administered by inhalation, by oral administration, by injection, or by a combination thereof.

Clause 25. The method of clause 20, wherein the IL-13 antagonist is an anti-IL13 antibody, or antigen-binding fragment thereof.

Clause 26. The method of clause 25, wherein the antibody or fragment thereof binds to the same IL-13 epitope as tralokinumab or competitively inhibits binding of tralokinumab to IL-13, or both.

Clause 27. The method of clause 25 or clause 26, wherein the antibody or fragment thereof is tralokinumab or an antigen-binding fragment thereof.

Clause 28. A method of measuring periostin levels in a sample obtained from a subject comprising assaying the sample in an immunoassay employing one or more anti-periostin antibodies or antigen binding fragments thereof, wherein the anti-periostin antibodies recognize isoforms 1, 2, 3, and 4 of human periostin.

Clause 29. The method of any one of clauses 1 to 28, wherein each of the one or more anti-periostin antibodies comprise an isolated antibody or antigen-binding fragment or derivative thereof which binds to the same periostin epitope as monoclonal antibody 4B4.B11 produced from a hybridoma deposited at the American Type Culture Collection (ATCC) under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 30. The method of any one of clauses 1 to 29, wherein each of the one or more anti-periostin antibodies comprise an isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 31. The method of clause 29 or clause 30, wherein each of the one or more anti-periostin antibodies is an isolated antibody or antigen-binding fragment or derivative thereof comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 32. The method of clause 29 or clause 30, wherein each of the one or more anti-periostin antibodies is an isolated antibody or antigen-binding fragment or derivative thereof comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 33. The method of any one of clauses 29 to 32, wherein the antibody or fragment thereof further comprises a heterologous polypeptide fused thereto.

Clause 34. The method of clause 33, wherein the heterologous polypeptide is a stabilizing polypeptide, a tag, a label, or a combination thereof.

Clause 35. The method of any one of clauses 29 to 34, wherein the antibody or fragment thereof is conjugated to a heterologous moiety.

Clause 36. The method of clause 35, wherein the heterologous moiety comprises one or more of: a peptide, a protein, an enzyme, a lipid, a heterologous antibody or fragment thereof, a detectable label, or polyethylene glycol (PEG).

Clause 37. The method of clause 35, wherein the heterologous moiety comprises biotin or a ruthenium chelate.

Clause 38. The method of any one of clauses 1 to 37, wherein the sample taken from the patient comprises one or more of whole blood, serum, plasma, saliva, sputum, bronchoalveolar lavage fluid, lung epithelial cells, or nasal polyps.

Clause 39. The method of clause 38, wherein the one or more control samples are obtained from normal healthy individuals; patients with a non-IL-13-mediated subset of asthma, COPD, IPF, or UC; a pre-determined standard amount of isolated periostin; or a combination thereof.

Clause 40. The method of clause 39, wherein the one or more samples obtained from normal healthy individuals or patients with a non-IL-13-mediated subset of asthma, COPD, IPF, or UC comprise one or more of whole blood, serum, plasma, saliva, sputum, bronchoalveolar lavage fluid, lung epithelial cells, or a combination thereof, wherein the control sample is matched to the sample taken from the patient.

Clause 41. The method of any one of clauses 1 to 40, wherein the immunoassay comprises a sandwich immunoassay comprising a first anti-periostin "capture" antibody or antigen-binding fragment thereof attached to a solid support, and a second anti-periostin "detection" antibody or antigen binding fragment thereof.

Clause 42. The method of clause 41, wherein the immunoassay comprises attaching a capture antibody or antigen-binding fragment thereof to a solid support; applying the patient sample or control sample under conditions sufficient to allow periostin, if present in the sample, to bind to the capture antibody or antigen-binding fragment thereof;

applying the detection antibody or antigen-binding fragment thereof under conditions sufficient to allow binding to periostin already bound to the capture antibody or antigen-binding fragment thereof; and measuring the amount of detection antibody or antigen-binding fragment thereof bound to periostin.

Clause 43. The method of clause 42, wherein the detection antibody or fragment thereof further comprises a detectable label.

Clause 44. The method of clause 43, wherein the detectable label is biotin.

Clause 45. The method of clause 43, wherein the detectable label is ruthenium chelate.

Clause 46. The method of any one of clauses 37 to 41, wherein the capture antibody is 3C11.G5 or 7B5.C4.

Clause 47. The method of any one of clauses 41 to 46, wherein the detection antibody is 4B4.B11 or 7B5.C4.

Clause 48. The method of clause 46 or clause 47, wherein the capture antibody is 7B5.C4 and the detection antibody is 4B4.B11.

Clause 49. An isolated antibody or antigen-binding fragment or derivative thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 50. An isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 51. The isolated antibody or fragment or derivative thereof of clause 49 or clause 50, comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 52. The isolated antibody, or fragment or derivative thereof of clause 49 or clause 51, comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 53. The isolated antibody or fragment or derivative thereof of any one of clauses 49 to 52, wherein the antibody fragment is a Fab fragment, a Fab' fragment, a F(ab')2 fragment, a Fv fragment, or a single chain antibody molecule.

Clause 54. A hybridoma selected from the group consisting of the hybridoma deposited at the ATCC under Deposit No. PTA-120210, the hybridoma deposited at the ATCC under Deposit No. PTA-120211, the hybridoma deposited at the ATCC under Deposit No. PTA-120209, and a combination thereof.

Clause 55. An antibody-producing cell culture comprising: a hybridoma selected from the group consisting of the hybridoma deposited at the ATCC under Deposit No. PTA-120210, the hybridoma deposited at the ATCC under Deposit No. PTA-120211, the hybridoma deposited at the ATCC under Deposit No. PTA-120209, and a combination thereof.

Clause 56. The antibody or fragment thereof of any one of clauses 49 to 53, or the antibody produced by the hybridoma of clause 54 or the cell culture of clause 55, wherein the antibody or fragment thereof further comprises a heterologous polypeptide fused thereto.

Clause 57. The antibody or fragment thereof of clause 56, wherein the heterologous polypeptide is a stabilizing polypeptide, a tag, a label, or a combination thereof.

Clause 58. The antibody or fragment thereof of any one of clauses 49 to 53, 56, or 57, or the antibody produced by hybridoma of clause 54 or the cell culture of clause 55, wherein the antibody or fragment thereof is conjugated to a heterologous moiety.

Clause 59. The antibody or fragment thereof of clause 58, wherein the heterologous moiety comprises one or more of: a peptide, a protein, an enzyme, a lipid, a heterologous antibody or fragment thereof, a detectable label, or polyethylene glycol (PEG).

Clause 60. The antibody or fragment thereof of clause 59, wherein the heterologous moiety comprises biotin or a ruthenium chelate.

Clause 61. A composition comprising an antibody or fragment thereof of any one of clauses 49 to 53, or 56 to 60, or the antibody produced by the hybridoma of clause 54 or the cell culture of clause 55.

Clause 62. A composition comprising a combination of two or more antibodies or fragments thereof of any one of clauses 49 to 53, or 56 to 60, or the antibody produced by the hybridoma of clause 54 or the cell culture of clause 55.

Clause 63. A kit for measuring periostin levels in a sample, comprising one or more of the antibodies or fragments thereof of any one of clauses 49 to 53, or 56 to 60, or the antibody produced by the hybridoma of clause 54 or the cell culture of clause 55.

Clause 64. The kit of clause 63, further comprising a solid support and detection reagents.

Clause 65. The kit of clause 63 or clause 64, comprising a capture antibody or fragment thereof and a detection antibody or fragment thereof.

Clause 66. The kit of any one of clauses 63 to 65, wherein the capture antibody is 7B5.C4 or an antigen-binding fragment thereof and the detection antibody is 4B4.B11 or an antigen-binding fragment thereof.

Clause 67. The kit of clause 63 or clause 67, wherein the detection antibody comprises a detectable label.

Clause 68. The kit of clause 67, wherein the detectable label is biotin and the detection reagents comprise a streptavidin-horse radish peroxidase (HRP) conjugate and a colorimetric substrate for HRP.

Clause 69. The kit of clause 67, wherein the detectable label is a ruthenium chelate.

Clause 70. An immunoassay for detecting periostin levels in one or more samples, comprising the use of one or more anti-periostin antibodies or antigen-binding fragments thereof, wherein the one or more antibodies or antigen-binding fragments thereof recognize isoforms 1, 2, 3, and 4 of human periostin.

Clause 71. The immunoassay of clause 70, wherein the one or more anti-periostin antibodies or antigen-binding fragments thereof bind to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 72. The immunoassay of clause 70, wherein the one or more anti-periostin antibodies or antigen-binding fragments thereof competitively inhibit binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 73. The immunoassay of clause 71 or clause 72, wherein the one or more anti-periostin antibodies or antigen-binding fragments thereof comprise a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or antigen-binding fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 74. The immunoassay of any one of clauses 71 to 73, wherein the one or more anti-periostin antibodies or antigen-binding fragments thereof comprise a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 75. The immunoassay of clause 74, wherein the assay is a sandwich immunoassay comprising a first anti-periostin "capture" antibody or antigen-binding fragment thereof attached to a solid support, and a second anti-periostin "detection" antibody or antigen-binding fragment thereof.

Clause 76. The immunoassay of clause 75, comprising attaching a capture antibody or antigen-binding fragment thereof to a solid support; applying the test sample or a control sample under conditions sufficient to allow periostin, if present in the sample, to bind to the capture antibody or antigen-binding fragment thereof; applying the detection antibody or antigen-binding fragment thereof under conditions sufficient to allow binding to periostin already bound to the capture antibody or antigen-binding fragment thereof; and measuring the amount of detection antibody or antigen-binding fragment thereof bound to periostin.

Clause 77. The immunoassay of clause 76, wherein the detection antibody or antigen-binding fragment thereof further comprises a detectable label.

Clause 78. The immunoassay of clause 77, wherein the detectable label is biotin.

Clause 79. The immunoassay of clause 77, wherein the detectable label is ruthenium chelate.

Clause 80. The immunoassay of any one of clauses 75 to 79, wherein the capture antibody is 3C11.G5 or 7B5.C4.

Clause 81. The immunoassay of any one of clauses 75 to 80, wherein the detection antibody is 4B4.B11 or 7B5.C4.

Clause 82. The immunoassay of any one of clauses 75 to 81, wherein the capture antibody is 7B5.C4 and the detection antibody is 4B4.B11, or the capture antibody is 4B4.B11 and the detection antibody is 7B5.C4.

Clause 83. The method of any one of clauses 1 to 48, wherein the patient is an asthma patient, wherein the sample taken from the patient comprises serum, and wherein the predetermined threshold periostin level is at least about 15 ng/mL.

Clause 84. The method of clause 83, wherein the predetermined threshold periostin level is in the range of about 15 ng/mL to about 25 ng/mL.

Clause 85. The method of clause 83, wherein the predetermined threshold periostin level is at least about 25 ng/mL.

Clause 86. The method of any one of clauses 1 to 48, wherein the patient is an IPF patient, wherein the sample taken from the patient comprises serum, and wherein the predetermined threshold periostin level is at least about 40 ng/mL.

Clause 87. The method of clause 86, wherein the predetermined threshold periostin level is in the range of about 40 ng/mL to about 60 ng/mL.

Clause 88. The method of clause 86, wherein the predetermined threshold periostin level is at least about 60 ng/mL.

Clause 89. The method of any one of clauses 1 to 48, wherein the patient is an IPF patient, wherein the sample taken from the patient comprises a lung tissue extract, and wherein the predetermined threshold periostin level is at least about 5 pg/mg total protein.

Clause 90. The method of clause 89, wherein the predetermined threshold periostin level is in the range of about 5 pg/mg total protein to about 25 mg/pg total protein.

Clause 91. The method of clause 89, wherein the predetermined threshold periostin level is at least about 15 pg/mg total protein or at least about 25 pg/mg total protein.

Clause 92. The method of any one of clauses 1 to 48, wherein the patient is a UC patient, wherein the sample taken from the patient comprises serum, and wherein the predetermined threshold periostin level is at least about 20 ng/mL.

Clause 93. The method of clause 92, wherein the predetermined threshold periostin level is in the range of about 20 ng/mL to about 40 ng/mL.

Clause 94. The method of clause 92, wherein the predetermined threshold periostin level is at least about 40 ng/mL.

Clause 95. A method of treating a patient having an IL-13-mediated disease or disorder, comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, 4, 7, and 8 of human periostin.

Clause 96. A method of treating a patient having an IL-13-mediated disease or disorder, comprising administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, 4, 7, and 8 of human periostin.

Clause 97. The method of clause 95 or clause 96, wherein a sample is obtained from the patient and is submitted for measurement of the periostin level in the sample.

Clause 98. A method of treating a patient having an IL-13-mediated disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; (b) administering an IL-13 antagonist to the patient if the patient's periostin level in the first sample is above a predetermined threshold level, or is elevated relative to the periostin level in one or more control samples.

Clause 99. A method of treating a patient having an IL-13-mediated disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; and (b) administering an IL-13 antagonist to the patient identified as a candidate for treatment by having a periostin level in the first sample above a predetermined threshold level, or by having an elevated periostin level relative to a periostin level in one or more control samples.

Clause 100. The method of clause 98 or clause 99, further comprising: (c) submitting a second sample taken from the patient for measurement of a second periostin level in the sample, wherein the patient's second periostin level is measured in an immunoassay employing one or more anti-periostin antibodies or antigen binding fragments thereof which recognize isoforms 1, 2, 3, 4, 7, and 8 of human periostin; and (d) increasing or maintaining the amount or frequency of the IL-13 antagonist administered to the patient if the patient's periostin level in the second sample is higher than the periostin level in the first sample, or maintaining or reducing the amount or frequency of the IL-13 antagonist administered to the patient if the patient's periostin level in the second sample is lower than or about the same as the periostin level in the first sample.

Clause 101. A method of treating a patient having an IL-13-mediated disease or disorder comprising: (a) measuring the periostin level in a first sample obtained from a patient having an IL-13-mediated disease or disorder, wherein the patient's periostin level in the first sample is measured in an immunoassay employing one or more anti-periostin antibodies or antigen binding fragments thereof which recognize isoforms 1, 2, 3, 4, 7, and 8 of human periostin; (b) determining whether the patient's periostin level in the first sample is above a predetermined threshold level, or is elevated relative to the periostin level in one or more control samples; and (c) advising a healthcare provider to administer an IL-13 antagonist to the patient if the patient's periostin level is above a predetermined threshold level, or is elevated relative to the periostin level in one or more control samples.

Clause 102. The method of clause 101, further comprising: (d) measuring the periostin level in a second sample obtained from the patient, wherein the patient's periostin level in the second sample is measured in an immunoassay employing one or more anti-periostin antibodies or antigen binding fragments thereof which recognize isoforms 1, 2, 3, 4, 7, and 8 of human periostin; (e) determining whether the patient's periostin level in the second sample is higher than, about the same as, or lower than the periostin level measured in the first sample; and (f) advising a healthcare provider to increase or maintain the amount or frequency of the IL-13 antagonist administered to the patient if the patient's periostin level in the second sample is higher than the periostin level in the first sample, or to maintain or reduce the amount or frequency of the IL-13 antagonist administered to the patient if the patient's periostin level in the second sample is lower than or about the same as the periostin level in the first sample.

Clause 103. A method of monitoring the therapeutic efficacy of an IL-13 antagonist therapeutic regimen in a patient having an IL-13-mediated disease or disorder comprising: (a) measuring, or instructing a clinical laboratory to measure the periostin level in a first sample obtained from a patient having an IL-13-mediated disease or disorder, wherein the patient's periostin level is measured in an immunoassay employing one or more anti-periostin antibodies or antigen binding fragments thereof which recognize isoforms 1, 2, 3, 4, 7, and 8 of human periostin; (b) administering, or advising a healthcare professional to administer an IL-13 antagonist to a patient if the patient's periostin level in the first sample is above a predetermined threshold level, or is elevated relative to the periostin level in one or more control samples; (c) measuring the periostin level in a second sample obtained from the patient, wherein the patient's periostin level in the second sample is measured in an immunoassay employing one or more anti-periostin antibodies or antigen binding fragments thereof which recognize isoforms 1, 2, 3, 4, 7, and 8 of human periostin; and (d) determining, or obtaining results indicating whether the patient's periostin level in the second sample is higher than, about the same as, or lower than the periostin level measured in the first sample; wherein the IL-13 antagonist therapeutic regimen is effective if the patient's periostin level in the second sample is lower than or about the same as the periostin level in the first sample.

Clause 104. The method of any one of clauses 95 to 101, wherein the patient has been diagnosed with a pulmonary disease or disorder, an inflammatory bowel disease or disorder, or a chronic inflammatory skin disease, following a differential diagnosis, and wherein the differential diagnosis includes testing for IL-13-mediated diseases or disorders.

Clause 105. The method of clause 104, wherein the differential diagnosis comprises one or more of: measuring the patient's IgE levels, measuring the patient's eosinophil count, making a symptom analysis, determining the patient's Fraction of Exhaled Nitric Oxide ($FE_{NO}$), and determining the patient's Eosinophil/Lymphocyte and Eosinophil/Neutrophil (ELEN) index.

Clause 106. The method of clause 104 or clause 105, wherein the pulmonary disease or disorder is asthma, idiopathic pulmonary fibrosis (IPF), chronic obstructive pulmonary disease (COPD), allergic rhinitis, chronic rhinosinusitis, or a combination of two or more thereof, or wherein the inflammatory bowel disease is ulcerative colitis (UC).

Clause 107. A method of treating a patient diagnosed with a pulmonary disease or disorder comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, 4, 7, and 8 of human periostin.

Clause 108. A method of treating a patient diagnosed with a pulmonary disease or disorder comprising administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, 4, 7, and 8 of human periostin.

Clause 109. A method of treating a patient diagnosed with a pulmonary disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; (b) administering an IL-13 antagonist to a patient if the patient's periostin level in the first sample is above a predetermined threshold level, or is elevated relative to the periostin level in one or more control samples.

Clause 110. A method of treating a patient diagnosed with a pulmonary disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; and (b) administering an IL-13 antagonist to a patient identified as a candidate for treatment by having a periostin level in the first sample above a predetermined threshold level, or by having an elevated periostin level relative to a periostin level in one or more control samples.

Clause 111. A method of treating a patient diagnosed with a chronic inflammatory skin disease or disorder comprising administering an IL-13 antagonist to the patient if the periostin level in a sample taken from the patient is above a predetermined threshold level, or is elevated relative to the periostin level in one or more control samples; wherein the patient's periostin level is measured in an immunoassay employing one or more anti-periostin antibodies or antigen binding fragments thereof which recognize isoforms 1, 2, 3, 4, 7, and 8 of human periostin.

Clause 112. A method of treating a patient diagnosed with a chronic inflammatory skin disease or disorder comprising administering an IL-13 antagonist to the patient; wherein the patient is identified as a candidate for treatment by having a periostin level in a sample taken from the patient above a predetermined threshold level, or by having an elevated periostin level relative to a periostin level in one or more control samples; and wherein the patient's periostin level is measured in an immunoassay employing one or more anti-periostin antibodies or antigen binding fragments thereof which recognize isoforms 1, 2, 3, 4, 7, and 8 of human periostin.

Clause 113. A method of treating a patient diagnosed with a chronic inflammatory skin disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; (b) administering an IL-13 antagonist to a patient if the patient's periostin level in the first sample is above a predetermined threshold level, or is elevated relative to the periostin level in one or more control samples.

Clause 114. A method of treating a patient diagnosed with a chronic inflammatory skin disease or disorder comprising: (a) submitting a first sample taken from the patient for measurement of a first periostin level in the sample, wherein the patient's periostin level is measured in an immunoassay employing one or more anti-periostin antibodies or antigen binding fragments thereof which recognize isoforms 1, 2, 3, 4, 7, and 8 of human periostin; and (b) administering an IL-13 antagonist to a patient identified as a candidate for treatment by having a periostin level in the first sample above a predetermined threshold level, or by having an elevated periostin level relative to a periostin level in one or more control samples.

Clause 115. The method of clause 109, 110, 113, or 114, further comprising: (c) submitting a second sample taken from the patient for measurement of a second periostin level in the sample, wherein the patient's second periostin level is measured in an immunoassay employing one or more anti-periostin antibodies or antigen binding fragments thereof which recognize isoforms 1, 2, 3, 4, 7, and 8 of human periostin; and (d) increasing or maintaining the amount or frequency of the IL-13 antagonist administered to the patient if the patient's periostin level in the second sample is higher than or about the same as the periostin level in the first sample, or maintaining or reducing the amount or frequency of the IL-13 antagonist administered to the patient if the patient's periostin level in the second sample is lower than the periostin level in the first sample.

Clause 116. A method of determining whether to treat a patient diagnosed with a pulmonary disease or disorder with an IL-13 antagonist therapeutic regimen comprising: (a) measuring, or instructing a clinical laboratory to measure the periostin level in a first sample obtained from a patient diagnosed with a pulmonary disease or disorder, wherein the patient's periostin level is measured in an immunoassay employing one or more anti-periostin antibodies or antigen binding fragments thereof which recognize isoforms 1, 2, 3, 4, 7, and 8 of human periostin; and (b) treating, or instructing a healthcare provider to treat the patient with an IL-13 antagonist therapeutic regimen if the patient's periostin level in the first sample is above a predetermined threshold level, or is elevated relative to the periostin level in one or more control samples.

Clause 117. The method of any one of clauses 107 to 110, 112, 115, or 116, wherein the pulmonary disease or disorder is asthma, IPF, COPD, allergic rhinitis, or chronic rhinosinusitis.

Clause 118. A method of determining whether to treat a patient diagnosed with a chronic inflammatory skin disease or disorder with an IL-13 antagonist therapeutic regimen comprising: (a) measuring, or instructing a clinical laboratory to measure the periostin level in a first sample obtained from a patient diagnosed with a chronic inflammatory skin disease or disorder, wherein the patient's periostin level is measured in an immunoassay employing one or more anti-periostin antibodies or antigen binding fragments thereof which recognize isoforms 1, 2, 3, 4, 7, and 8 of human periostin; and (b) treating, or instructing a healthcare provider to treat the patient with an IL-13 antagonist therapeutic regimen if the patient's periostin level in the first sample is above a predetermined threshold level, or is elevated relative to the periostin level in one or more control samples.

Clause 119. The method of any one of clauses 111-115, wherein the chronic inflammatory skin disease or disorder is atopic dermatitis.

Clause 120. The method of any one of clauses 95 to 119, wherein the IL-13 antagonist comprises one or more of an anti-IL-13 antibody or antigen-binding fragment thereof, an IL-13 mutein, an IL-4 mutein, an anti-IL-13Rα1 antibody or antigen-binding fragment thereof, or an anti-IL-4Rα antibody or antigen-binding fragment thereof.

Clause 121. The method of any one of clauses 107 to 120, wherein the patient has been treated with one or more additional medications, either before, during, or after administration of an IL-13 antagonist.

Clause 122. The method of clause 121, wherein the one or more additional medications comprise steroids, a bronchodilator, or a combination thereof.

Clause 123. The method of clause 122, wherein the steroid is fluticasone or budesonide, and the bronchodilator is salbutamol.

Clause 124. The method of any one of clauses 121 to 123, wherein the one or more additional medications are administered by inhalation, by oral administration, by injection, or by a combination thereof.

Clause 125. The method of clause 120, wherein the IL-13 antagonist is an anti-IL13 antibody, or antigen-binding fragment thereof.

Clause 126. The method of clause 125, wherein the antibody or fragment thereof binds to the same IL-13 epitope as tralokinumab or competitively inhibits binding of tralokinumab to IL-13, or both.

Clause 127. The method of clause 125 or clause 126, wherein the antibody or fragment thereof is tralokinumab or an antigen-binding fragment thereof.

Clause 128. A method of measuring periostin levels in a sample obtained from a subject comprising assaying the sample in an immunoassay employing one or more anti-periostin antibodies or antigen binding fragments thereof, wherein the anti-periostin antibodies recognize isoforms 1, 2, 3, 4, 7, and 8 of human periostin.

Clause 129. The method of any one of clauses 95 to 128, wherein each of the one or more anti-periostin antibodies comprise an isolated antibody or antigen-binding fragment or derivative thereof which binds to the same periostin epitope as monoclonal antibody 4B4.B11 produced from a hybridoma deposited at the American Type Culture Collection (ATCC) under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 130. The method of any one of clauses 95 to 129, wherein each of the one or more anti-periostin antibodies comprise an isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 131. The method of clause 129 or clause 130, wherein each of the one or more anti-periostin antibodies is an isolated antibody or antigen-binding fragment or derivative thereof comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 132. The method of clause 129 or clause 130, wherein each of the one or more anti-periostin antibodies is an isolated antibody or antigen-binding fragment or derivative thereof comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 133. The method of any one of clauses 129 to 132, wherein the antibody or fragment thereof further comprises a heterologous polypeptide fused thereto.

Clause 134. The method of clause 133, wherein the heterologous polypeptide is a stabilizing polypeptide, a tag, a label, or a combination thereof.

Clause 135. The method of any one of clauses 129 to 134, wherein the antibody or fragment thereof is conjugated to a heterologous moiety.

Clause 136. The method of clause 135, wherein the heterologous moiety comprises one or more of: a peptide, a protein, an enzyme, a lipid, a heterologous antibody or fragment thereof, a detectable label, or polyethylene glycol (PEG).

Clause 137. The method of clause 135, wherein the heterologous moiety comprises biotin, ruthenium chelate, or acridinium.

Clause 138. The method of any one of clauses 95 to 137, wherein the sample taken from the patient comprises one or more of whole blood, serum, plasma, saliva, sputum, bronchoalveolar lavage fluid, lung epithelial cells, or nasal polyps.

Clause 139. The method of clause 138, wherein the one or more control samples are obtained from normal healthy individuals; patients with a non-IL-13-mediated subset of asthma, COPD, IPF, atopic dermatitis, or UC; a pre-determined standard amount of isolated periostin; or a combination thereof.

Clause 140. The method of clause 139, wherein the one or more samples obtained from normal healthy individuals or patients with a non-IL-13-mediated subset of asthma, COPD, IPF, atopic dermatitis, or UC comprise one or more of whole blood, serum, plasma, saliva, sputum, bronchoalveolar lavage fluid, lung epithelial cells, or a combination thereof, wherein the control sample is matched to the sample taken from the patient.

Clause 141. The method of any one of clauses 95 to 140, wherein the immunoassay comprises a sandwich immunoassay comprising a first anti-periostin "capture" antibody or antigen-binding fragment thereof attached to a solid support, and a second anti-periostin "detection" antibody or antigen binding fragment thereof.

Clause 142. The method of clause 141, wherein the immunoassay comprises: (a) attaching a capture antibody or antigen-binding fragment thereof to a solid support; (b) applying the patient sample or control sample under conditions sufficient to allow periostin, if present in the sample, to bind to the capture antibody or antigen-binding fragment thereof; (c) applying the detection antibody or antigen-binding fragment thereof under conditions sufficient to allow binding to periostin already bound to the capture antibody or antigen-binding fragment thereof; and (d) measuring the amount of detection antibody or antigen-binding fragment thereof bound to periostin.

Clause 143. The method of clause 142, wherein the detection antibody or fragment thereof further comprises a detectable label.

Clause 144. The method of clause 143, wherein the detectable label is biotin.

Clause 145. The method of clause 143, wherein the detectable label is ruthenium chelate.

Clause 146. The method of clause 143, wherein the detectable label comprises acridinium.

Clause 147. The method of any one of clauses 141 to 146, wherein the capture antibody is 3C11.G5 or 7B5.C4.

Clause 148. The method of any one of clauses 141 to 147, wherein the detection antibody is 4B4.B11 or 7B5.C4.

Clause 149. The method of clause 147 or clause 148, wherein the capture antibody is 7B5.C4 and the detection antibody is 4B4.B11.

Clause 150. A kit for measuring periostin levels in a sample, comprising one or more of: (a) an isolated antibody or antigen-binding fragment or derivative thereof which binds to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209; (b) an isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin; (c) an isolated antibody or antigen-binding fragment or derivative thereof of as recited in (a) or (b), comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209; (d) an isolated antibody or antigen-binding fragment or derivative thereof as recited in (a) or (c) comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209; (e) an isolated antibody or antigen-binding fragment or derivative thereof produced by a hybridoma selected from the group consisting of the hybridoma deposited at the ATCC under Deposit No. PTA-120210, the hybridoma deposited at the ATCC under Deposit No. PTA-120211, the hybridoma deposited at the ATCC under Deposit No. PTA-120209; (f) an isolated antibody or antigen-binding fragment or derivative thereof as recited in (a)-(e) wherein the antibody fragment is a Fab fragment, a Fab' fragment, a F(ab')2 fragment, a Fv fragment, or a single chain antibody molecule; (g) an isolated antibody or antigen-binding fragment or derivative thereof of as recited in any one of (a)-(f) further comprising a heterologous polypeptide fused thereto comprising a stabilizing polypeptide, a tag, a label, or a combination thereof; and (h) an isolated antibody or antigen-binding fragment or derivative thereof of as recited in any one of (a)-(g) conjugated to a heterologous moiety comprising one or more of a peptide, a protein, an enzyme, a lipid, a heterologous antibody or fragment thereof, a detectable label, or polyethylene glycol (PEG).

Clause 151. The kit of clause 150, further comprising a solid support and detection reagents.

Clause 152. The kit of clause 150 or clause 151, comprising a capture antibody or fragment thereof and a detection antibody or fragment thereof.

Clause 153. The kit of any one of clauses 150 to 152, wherein the capture antibody is 7B5.C4 or an antigen-binding fragment thereof and the detection antibody is 4B4.B11 or an antigen-binding fragment thereof.

Clause 154. The kit of clause 152 or clause 153, wherein the detection antibody comprises a detectable label.

Clause 155. The kit of clause 154, wherein the detectable label comprises acridinium.

Clause 156. The kit of clause 154, wherein the detectable label is biotin and the detection reagents comprise a streptavidin-horse radish peroxidase (HRP) conjugate and a colorimetric substrate for HRP.

Clause 157. The kit of clause 154, wherein the detectable label is a ruthenium chelate.

Clause 158. An immunoassay for detecting periostin levels in one or more samples, comprising the use of one or more anti-periostin antibodies or antigen-binding fragments thereof, wherein the one or more antibodies or antigen-binding fragments thereof recognize isoforms 1, 2, 3, 4, 7, and 8 of human periostin.

Clause 159. The immunoassay of clause 158, wherein the one or more anti-periostin antibodies or antigen-binding fragments thereof bind to the same periostin epitope as monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 160. The immunoassay of clause 158, wherein the one or more anti-periostin antibodies or antigen-binding fragments thereof competitively inhibit binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 161. The immunoassay of clause 159 or clause 160, wherein the one or more anti-periostin antibodies or antigen-binding fragments thereof comprise a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or antigen-binding fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 162. The immunoassay of any one of clauses 159 to 161, wherein the one or more anti-periostin antibodies or antigen-binding fragments thereof comprise a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 163. The immunoassay of clause 162, wherein the assay is a sandwich immunoassay comprising a first anti-periostin "capture" antibody or antigen-binding fragment thereof attached to a solid support, and a second anti-periostin "detection" antibody or antigen-binding fragment thereof.

Clause 164. The immunoassay of clause 163, comprising: (a) attaching a capture antibody or antigen-binding fragment thereof to a solid support; (b) applying the test sample or a control sample under conditions sufficient to allow periostin, if present in the sample, to bind to the capture antibody or antigen-binding fragment thereof; (c) applying the detection antibody or antigen-binding fragment thereof under conditions sufficient to allow binding to periostin already bound to the capture antibody or antigen-binding fragment thereof; and (d) measuring the amount of detection antibody or antigen-binding fragment thereof bound to periostin.

Clause 165. The immunoassay of clause 164, wherein the detection antibody or antigen-binding fragment thereof further comprises a detectable label.

Clause 166. The immunoassay of clause 165, wherein the detectable label is biotin.

Clause 167. The immunoassay of clause 165, wherein the detectable label is ruthenium chelate or acridinium.

Clause 168. The immunoassay of any one of clauses 163 to 167, wherein the capture antibody is 3C11.G5 or 7B5.C4.

Clause 169. The immunoassay of any one of clauses 163 to 168, wherein the detection antibody is 4B4.B11 or 7B5.C4.

Clause 170. The immunoassay of any one of clauses 163 to 169, wherein the capture antibody is 7B5.C4 and the detection antibody is 4B4.B11, or the capture antibody is 4B4.B11 and the detection antibody is 7B5.C4.

Clause 171. The method of any one of clauses 95 to 149, wherein the patient is an asthma patient, wherein the sample taken from the patient comprises serum, and wherein the predetermined threshold periostin level is at least about 15 ng/mL.

Clause 172. The method of clause 171, wherein the predetermined threshold periostin level is in the range of about 15 ng/mL to about 25 ng/mL.

Clause 173. The method of clause 171, wherein the predetermined threshold periostin level is at least about 25 ng/mL.

Clause 174. The method of clause 171 or 172, wherein the predetermined threshold periostin level is at least about 16.44 ng/mL.

Clause 175. The method of any one of clauses 95 to 149, wherein the patient is an IPF patient, wherein the sample taken from the patient comprises serum, and wherein the predetermined threshold periostin level is at least about 40 ng/mL.

Clause 176. The method of clause 175, wherein the predetermined threshold periostin level is in the range of about 40 ng/mL to about 60 ng/mL.

Clause 177. The method of clause 175, wherein the predetermined threshold periostin level is at least about 60 ng/mL.

Clause 178. The method of any one of clauses 95 to 149, wherein the patient is an IPF patient, wherein the sample taken from the patient comprises a lung tissue extract, and wherein the predetermined threshold periostin level is at least about 5 pg/mg total protein.

Clause 179. The method of clause 178, wherein the predetermined threshold periostin level is in the range of about 5 pg/mg total protein to about 25 mg/pg total protein.

Clause 180. The method of clause 178, wherein the predetermined threshold periostin level is at least about 15 pg/mg total protein or at least about 25 pg/mg total protein.

Clause 181. The method of any one of clauses 95 to 149, wherein the patient is a UC patient, wherein the sample taken from the patient comprises serum, and wherein the predetermined threshold periostin level is at least about 20 ng/mL.

Clause 182. The method of clause 181, wherein the predetermined threshold periostin level is in the range of about 20 ng/mL to about 40 ng/mL.

Clause 183. The method of clause 181, wherein the predetermined threshold periostin level is at least about 40 ng/mL.

Clause 184. The method of any one of clauses 95 to 149, wherein the patient is an atopic dermatitis patient, and wherein the sample taken from the patient is serum.

Clause 185. A method for determining periostin levels in a test sample, the method comprising: (a) contacting the test sample with at least one capture antibody, wherein the capture antibody binds to an epitope on periostin or a fragment of periostin to form a capture antibody-periostin antigen complex; (b) contacting the capture antibody-periostin antigen complex with at least one detection antibody comprising a detectable label, wherein the detection antibody binds to an epitope on periostin that is not bound by the capture antibody and forms a capture antibody-periostin antigen-detection antibody complex; and (c) determining the periostin concentration in the test sample based on the signal generated by the detectable label in the capture antibody-periostin antigen-detection antibody complex formed in (b), wherein the at least one capture antibody comprises an isolated antibody or antigen-binding fragment or derivative thereof which recognizes isoforms 1, 2, 3, 4, 7, and 8 of human periostin, wherein the at least one detection antibody comprises an isolated antibody or antigen-binding fragment or derivative thereof which recognizes isoforms 1, 2, 3, 4, 7, and 8 of human periostin, and wherein the least one capture antibody is different from the at least one detection antibody.

Clause 186. The method of clause 185, wherein the isolated antibody or antigen-binding fragment or derivative thereof which recognizes isoforms 1, 2, 3, 4, 7, and 8 of human periostin comprises: a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209; a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209; or an antibody produced by a hybridoma selected from the group consisting of the hybridoma deposited at the ATCC under Deposit No. PTA-120210, the hybridoma deposited at the ATCC under Deposit No. PTA-120211, and the hybridoma deposited at the ATCC under Deposit No. PTA-120209.

Clause 187. The method of clause 185 or 186, further comprising comparing the signal generated by the detectable label as a direct or indirect indication of the periostin concentration in the test sample to a signal generated as a direct or indirect indication of the periostin concentration in a control or calibrator.

Clause 188. The method of clause 187, wherein the periostin concentration in the test sample is used to determine or assess whether a subject has or is at risk of developing an IL-13-mediated disease or disorder.

Clause 189. The method of clause 188, wherein an increased periostin concentration as compared to the periostin concentration in a control or calibrator indicates that the subject has IL-13-mediated disease or disorder.

Clause 190. The method of clause 189, wherein the IL-13-mediated disease or disorder is asthma, idiopathic pulmonary fibrosis (IPF), chronic obstructive pulmonary disease (COPD), ulcerative colitis (UC), allergic rhinitis, atopic dermatitis, or chronic rhinosinusitis.

Clause 191. An isolated antibody or antigen-binding fragment or derivative thereof which binds to the same periostin epitope as monoclonal antibody 4B4.B11 produced from a hybridoma deposited at the American Type Culture Collection (ATCC) under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 192. An isolated antibody or antigen-binding fragment or derivative thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

Clause 193. The isolated antibody or fragment or derivative thereof of clause 191 or clause 192, comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 194. The isolated antibody or fragment or derivative thereof of clause 191 or clause 193 comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

Clause 195. A hybridoma selected from the group consisting of a hybridoma deposited at the ATCC under Deposit No. PTA-120210, a hybridoma deposited at the ATCC under Deposit No. PTA-120211, a hybridoma deposited at the ATCC under Deposit No. PTA-120209, and a combination thereof.

Clause 196. An isolated antibody or fragment or derivative thereof produced by the hybridoma of clause 195.

Clause 197. An antibody-producing cell culture comprising: a hybridoma selected from the group consisting of a hybridoma deposited at the ATCC under Deposit No. PTA-120210, a hybridoma deposited at the ATCC under Deposit No. PTA-120211, a hybridoma deposited at the ATCC under Deposit No. PTA-120209, and a combination thereof.

Clause 198. An isolated antibody or fragment or derivative thereof produced by the antibody-producing cell culture of clause 197.

Clause 199. The isolated antibody or fragment or derivative thereof of any one of clauses 191-194, 196, or 198 wherein the isolated antibody or fragment or derivative thereof recognizes isoforms 1, 2, 3, 4, 7, and 8 of human periostin.

Clause 200. The isolated antibody or fragment or derivative thereof of any one of clauses 191-194 196, 198, or 199 wherein the antibody fragment is a Fab fragment, a Fab' fragment, a F(ab')2 fragment, a Fv fragment, or a single chain antibody molecule.

Clause 201. The isolated antibody or fragment or derivative thereof of any one of clauses 191-194, 196, or 198-200, wherein the antibody or fragment thereof further comprises a heterologous polypeptide fused thereto.

Clause 202. The isolated antibody or fragment or derivative thereof of clause 201, wherein the heterologous polypeptide is a stabilizing polypeptide, a tag, a label, or a combination thereof.

Clause 203. The isolated antibody or fragment or derivative thereof of any one of clauses 191-194, 196, or 198-202, wherein the antibody or fragment thereof is conjugated to a heterologous moiety.

Clause 204. The isolated antibody or fragment or derivative thereof of clause 203, wherein the heterologous moiety comprises one or more of: a peptide, a protein, an enzyme, a lipid, a heterologous antibody or fragment thereof, a detectable label, or polyethylene glycol (PEG).

Clause 205. The antibody or fragment thereof of clause 204, wherein the heterologous moiety comprises biotin or a ruthenium chelate or acridinium.

Clause 206. A composition comprising the isolated antibody or fragment or derivative thereof of any one of clauses 191-194, 196, or 198-205.

Clause 207. A composition comprising a combination of two or more isolated antibodies or fragments or derivatives thereof of any one of clauses 191-194, 196, or 198-206.

Clause 208. An antigen-binding moiety of the isolated antibody or fragment or derivative thereof of any one of clauses 191-194, 196, or 198-207.

Clause 209. An isolated nucleic acid encoding the isolated antibody or fragment or derivative thereof of any one of clauses 191-194, 196, or 198-208.

Clause 210. A vector comprising the isolated nucleic acid of clause 209.

Clause 211. A host cell comprising the vector of clause 210.

Clause 212. The host cell of clause 211, wherein the host cell is a prokaryotic cell.

Clause 213. The host cell of clause 212, wherein the host cell is *E. coli*.

Clause 214. The host cell of clause 211, wherein the host cell is a eukaryotic cell.

Clause 215. The host cell of clause 214, wherein the eukaryotic cell is selected from the group consisting of protist cells, animal cells, plants cells, and fungal cells.

Clause 216. The host cell of clause 215, wherein the animal cell is selected from the group consisting of a mammalian cell, an avian cell, and an insect cell.

Clause 217. The host cell of clause 214, wherein the eukaryotic cell is a CHO cell, a COS cell, a NSO cell, or a yeast cell.

Clause 218. A kit comprising the isolated antibody or fragment or derivative thereof of any one of clauses 191-194, 196, or 198-208, the isolated nucleic acid of clauses 209, the vector of clause 210, or the host cell of any one of clauses 211-217.

What is claimed is:

1. An isolated monoclonal antibody or antigen-binding fragment thereof which binds to the same periostin epitope as monoclonal antibody 4B4.B11 produced from a hybridoma deposited at the American Type Culture Collection (ATCC) under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

2. An isolated monoclonal antibody or antigen-binding fragment thereof which competitively inhibits binding of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209 to periostin.

3. The isolated monoclonal antibody or fragment thereof of claim 1, comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody or fragment thereof are identical to the CDRs of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

4. The isolated monoclonal antibody or fragment thereof of claim 1 comprising a VH and a VL identical to the VH and VL of monoclonal antibody 4B4.B11 produced from a hybridoma deposited at the ATCC under Deposit No. PTA-120210, monoclonal antibody 7B5.C4 produced from a hybridoma deposited at the ATCC under Deposit No. PTA-120211, or monoclonal antibody 3C11.G5 produced from a hybridoma deposited at the ATCC under Deposit No. PTA-120209.

5. A hybridoma selected from a hybridoma deposited at the ATCC under Deposit No. PTA-120210, a hybridoma deposited at the ATCC under Deposit No. PTA-120211, a hybridoma deposited at the ATCC under Deposit No. PTA-120209, and a combination thereof.

6. An isolated monoclonal antibody or fragment thereof produced by the hybridoma of claim 5.

7. An antibody-producing cell culture comprising a hybridoma selected from a hybridoma deposited at the ATCC under Deposit No. PTA-120210, a hybridoma deposited at the ATCC under Deposit No. PTA-120211, a hybridoma deposited at the ATCC under Deposit No. PTA-120209, and a combination thereof.

8. An isolated monoclonal antibody or antigen-binding fragment thereof produced by the antibody-producing cell culture of claim 7.

9. The isolated monoclonal antibody or fragment thereof of claim 1, wherein the isolated antibody or fragment or derivative thereof recognizes isoforms 1, 2, 3, 4, 7, and 8 of human periostin.

10. The isolated monoclonal antibody or fragment thereof of claim 1, wherein the antibody fragment is a Fab fragment, a Fab' fragment, a F(ab')2 fragment, a Fv fragment, or a single chain antibody molecule.

11. The isolated monoclonal antibody or fragment thereof of claim 1, wherein the antibody or fragment thereof further comprises a heterologous polypeptide fused thereto.

12. The isolated monoclonal antibody or fragment thereof of claim 11, wherein the heterologous polypeptide is a stabilizing polypeptide, a tag, a label, or a combination thereof.

13. The isolated monoclonal antibody or fragment thereof of claim 1, wherein the antibody or fragment thereof is conjugated to a heterologous moiety.

14. The isolated monoclonal antibody or fragment thereof of claim 13, wherein the heterologous moiety comprises one or more of: a peptide, a protein, an enzyme, a lipid, a heterologous antibody or fragment thereof, a detectable label, and/or polyethylene glycol (PEG).

15. The isolated monoclonal antibody or fragment thereof of claim 14, wherein the heterologous moiety comprises biotin, a ruthenium chelate, or acridinium.

16. A composition comprising the isolated monoclonal antibody or fragment thereof of claim 1.

17. An antigen-binding moiety of the isolated monoclonal antibody or fragment thereof of claim 1.

18. A kit comprising the isolated monoclonal antibody or fragment thereof of claim 1 and instructions for use.

* * * * *